(12) United States Patent
O'Shaughnessy et al.

(10) Patent No.: US 12,404,337 B2
(45) Date of Patent: Sep. 2, 2025

(54) COMPOSITIONS, DOSES, AND METHODS FOR TREATMENT OF THYROID EYE DISEASE

(71) Applicant: Viridian Therapeutics, Inc., Waltham, MA (US)

(72) Inventors: Denis O'Shaughnessy, Waltham, MA (US); Barrett Katz, Waltham, MA (US)

(73) Assignee: Viridian Therapeutics, Inc., Waltham, MA (US)

( * ) Notice: Subject to any disclaimer, the term of this patent is extended or adjusted under 35 U.S.C. 154(b) by 24 days.

(21) Appl. No.: 18/391,233

(22) Filed: Dec. 20, 2023

(65) Prior Publication Data

US 2024/0343812 A1    Oct. 17, 2024

Related U.S. Application Data

(63) Continuation of application No. 17/818,798, filed on Aug. 10, 2022, now abandoned.

(60) Provisional application No. 63/261,744, filed on Sep. 28, 2021, provisional application No. 63/260,133, filed on Aug. 10, 2021.

(51) Int. Cl.
| | |
|---|---|
| *C07K 16/28* | (2006.01) |
| *A61K 39/00* | (2006.01) |
| *A61P 5/14* | (2006.01) |
| *A61P 27/02* | (2006.01) |
| *A61P 37/00* | (2006.01) |

(52) U.S. Cl.
CPC ............ *C07K 16/2863* (2013.01); *A61P 5/14* (2018.01); *A61P 27/02* (2018.01); *A61P 37/00* (2018.01); *A61K 2039/505* (2013.01); *A61K 2039/54* (2013.01); *A61K 2039/545* (2013.01); *C07K 2317/21* (2013.01); *C07K 2317/24* (2013.01); *C07K 2317/565* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | Decant et al. | |
| 4,447,233 A | 5/1984 | Mayfield | |
| 4,487,603 A | 12/1984 | Harris | |
| 4,596,556 A | 6/1986 | Morrow et al. | |
| 4,790,824 A | 12/1988 | Morrow et al. | |
| 4,816,567 A | 3/1989 | Cabilly et al. | |
| 4,941,880 A | 7/1990 | Burns | |
| 4,949,778 A | 8/1990 | Saito et al. | |
| 5,064,413 A | 11/1991 | Mckinnon et al. | |
| 5,260,203 A | 11/1993 | Ladner et al. | |
| 5,312,335 A | 5/1994 | Mckinnon et al. | |
| 5,383,851 A | 1/1995 | Mckinnon et al. | |
| 5,399,163 A | 3/1995 | Peterson et al. | |
| 5,475,096 A | 12/1995 | Gold et al. | |
| 5,831,012 A | 11/1998 | Nilsson et al. | |
| 6,004,746 A | 12/1999 | Brent et al. | |
| 6,005,079 A | 12/1999 | Casterman et al. | |
| 6,096,002 A | 8/2000 | Landau | |
| 6,620,135 B1 | 9/2003 | Weston et al. | |
| 6,794,144 B1 | 9/2004 | Saksela et al. | |
| 6,818,418 B1 | 11/2004 | Lipovsek et al. | |
| 6,994,982 B1 | 2/2006 | Watt et al. | |
| 7,083,784 B2 | 8/2006 | Dall et al. | |
| 7,166,697 B1 | 1/2007 | Galanis et al. | |
| 7,186,524 B2 | 3/2007 | Kolmar et al. | |
| 7,250,297 B1 | 7/2007 | Beste et al. | |
| 7,417,130 B2 | 8/2008 | Stumpp et al. | |
| 7,572,897 B2 | 8/2009 | Graus et al. | |
| 7,670,600 B2 | 3/2010 | Dall et al. | |
| 7,803,907 B2 | 9/2010 | Stemmer et al. | |
| 7,838,629 B2 | 11/2010 | Fiedler et al. | |
| 7,998,681 B2 | 8/2011 | Smith et al. | |
| 8,137,933 B2 | 3/2012 | Saha | |
| 8,153,121 B2 | 4/2012 | Smith et al. | |
| 8,394,925 B2 | 3/2013 | Chamberlain et al. | |
| 8,951,790 B2 | 2/2015 | Saha | |
| 9,045,536 B2 | 6/2015 | Merchant et al. | |
| 9,982,036 B2 | 5/2018 | Bossenmaier et al. | |
| 10,093,741 B1 * | 10/2018 | Burak | A61P 35/00 |
| 10,519,245 B2 | 12/2019 | Gastwirt et al. | |
| 10,611,825 B2 | 4/2020 | Bossenmaier et al. | |
| 11,548,951 B1 | 1/2023 | Bedian et al. | |
| 2004/0023334 A1 | 2/2004 | Prior | |
| 2004/0132094 A1 | 7/2004 | Etzerodt et al. | |
| 2004/0146938 A1 | 7/2004 | Nguyen et al. | |
| 2004/0157209 A1 | 8/2004 | Yilmaz et al. | |
| 2004/0202651 A1 | 10/2004 | Cohen et al. | |

(Continued)

FOREIGN PATENT DOCUMENTS

| | | |
|---|---|---|
| CN | 101229371 A | 7/2008 |
| CN | 101292036 A | 10/2008 |

(Continued)

OTHER PUBLICATIONS

Smith et al., N Engl J Med. May 4, 2017; 376(18): 1748-1761.*
International Search Report for PCT/US2021/054907 dated Feb. 23, 2022 (5 pages).
International Search Report for PCT/US2021/054914 dated Feb. 23, 2022 (6 pages).

(Continued)

*Primary Examiner* — Marianne P Allen
(74) *Attorney, Agent, or Firm* — Proskauer Rose LLP

(57) ABSTRACT

Antibodies and compositions against IGF-1R and uses thereof are provided herein.

8 Claims, 27 Drawing Sheets
Specification includes a Sequence Listing.

(56) References Cited

U.S. PATENT DOCUMENTS

| | | |
|---|---|---|
| 2004/0209243 A1 | 10/2004 | Nixon et al. |
| 2004/0265307 A1 | 12/2004 | Singh et al. |
| 2005/0084906 A1 | 4/2005 | Goetsch et al. |
| 2005/0136063 A1 | 6/2005 | Wang et al. |
| 2006/0140960 A1 | 6/2006 | Wang et al. |
| 2006/0286103 A1 | 12/2006 | Kolhe et al. |
| 2007/0041972 A1 | 2/2007 | Rother et al. |
| 2007/0071675 A1 | 3/2007 | Wu et al. |
| 2008/0014203 A1 | 1/2008 | Hansen et al. |
| 2008/0112888 A1 | 5/2008 | Wang |
| 2008/0226635 A1 | 9/2008 | Koll et al. |
| 2009/0275126 A1 | 11/2009 | Graus et al. |
| 2009/0285824 A1 | 11/2009 | Calzone et al. |
| 2010/0047239 A1 | 2/2010 | Wu et al. |
| 2010/0074900 A1 | 3/2010 | Ghayur et al. |
| 2010/0104645 A1 | 4/2010 | Ali et al. |
| 2010/0119446 A1 | 5/2010 | Grabulovski et al. |
| 2010/0143340 A1 | 6/2010 | Kolhe et al. |
| 2010/0239633 A1 | 9/2010 | Strome et al. |
| 2010/0260668 A1 | 10/2010 | Ghayur et al. |
| 2011/0014117 A1 | 1/2011 | Wang et al. |
| 2011/0014207 A1 | 1/2011 | Gualberto et al. |
| 2011/0044980 A1 | 2/2011 | Ghayur et al. |
| 2011/0229933 A1 | 9/2011 | Krishnan et al. |
| 2011/0263827 A1 | 10/2011 | Ghayur et al. |
| 2012/0014957 A1 | 1/2012 | Ghayur et al. |
| 2012/0027757 A1 | 2/2012 | Sathyanarayanan et al. |
| 2012/0065380 A1 | 3/2012 | Yoo et al. |
| 2012/0076778 A1 | 3/2012 | Koll et al. |
| 2012/0100166 A1 | 4/2012 | Roschke et al. |
| 2012/0201746 A1 | 8/2012 | Liu et al. |
| 2012/0237507 A1 | 9/2012 | Bossenmaier et al. |
| 2012/0263722 A1 | 10/2012 | Ghayur et al. |
| 2013/0004416 A1 | 1/2013 | Wu et al. |
| 2013/0195871 A1 | 8/2013 | Ghayur et al. |
| 2013/0259868 A1 | 10/2013 | Roschke et al. |
| 2013/0330323 A1 | 12/2013 | Dunn et al. |
| 2014/0050729 A1 | 2/2014 | Yao |
| 2014/0079665 A1 | 3/2014 | Goetsch et al. |
| 2015/0017168 A1 | 1/2015 | Ghayur et al. |
| 2015/0056191 A1 | 2/2015 | Sathyanarayanan et al. |
| 2015/0168424 A1 | 6/2015 | Wang |
| 2015/0274829 A1 | 10/2015 | Calzone et al. |
| 2016/0060299 A1 | 3/2016 | Luesch |
| 2016/0096894 A1 | 4/2016 | Cohen et al. |
| 2016/0151487 A1 | 6/2016 | Hartmann et al. |
| 2016/0159894 A1 | 6/2016 | Hartmann et al. |
| 2016/0289341 A1 | 10/2016 | Wu |
| 2016/0289343 A1 | 10/2016 | Wu |
| 2017/0218091 A1 | 8/2017 | Ambrosi |
| 2018/0243432 A1 | 8/2018 | Poma et al. |
| 2018/0280527 A1 | 10/2018 | Silacci Melkko et al. |
| 2018/0312573 A1 | 11/2018 | Bossenmaier et al. |
| 2019/0083662 A1 | 3/2019 | Burak et al. |
| 2019/0153071 A1 | 5/2019 | Klein et al. |
| 2019/0153471 A1 | 5/2019 | Paul et al. |
| 2019/0194713 A1 | 6/2019 | Mandell et al. |
| 2019/0225696 A1 | 7/2019 | Madden et al. |
| 2019/0270820 A1 | 9/2019 | Madden et al. |
| 2019/0293656 A1 | 9/2019 | Chaudhary |
| 2020/0023076 A1 | 1/2020 | Fotin-Mleczek et al. |
| 2020/0115460 A1 | 4/2020 | Eguchi et al. |
| 2021/0253719 A1* | 8/2021 | Sherman ............ A61K 39/3955 |
| 2021/0284741 A1 | 9/2021 | Madden et al. |
| 2022/0088231 A1 | 3/2022 | Burak et al. |
| 2022/0235137 A1 | 7/2022 | Bedian et al. |
| 2022/0267450 A1 | 8/2022 | Bedian et al. |
| 2022/0267451 A1 | 8/2022 | Bedian et al. |
| 2022/0275096 A1 | 9/2022 | Bedian et al. |
| 2023/0002495 A1 | 1/2023 | Bedian et al. |
| 2023/0084477 A1 | 3/2023 | O'shaughnessy et al. |
| 2023/0279122 A1 | 9/2023 | Bedian et al. |
| 2024/0043546 A1 | 2/2024 | Bedian et al. |
| 2024/0343812 A1 | 10/2024 | O'shaughnessy et al. |
| 2024/0343814 A1 | 10/2024 | Bedian et al. |
| 2024/0352133 A1 | 10/2024 | Bedian et al. |
| 2024/0360227 A1 | 10/2024 | Bedian et al. |
| 2024/0368282 A1 | 11/2024 | Schlegel et al. |
| 2025/0059287 A1 | 2/2025 | Bedian et al. |
| 2025/0099583 A1 | 3/2025 | Huyghe et al. |

FOREIGN PATENT DOCUMENTS

| | | |
|---|---|---|
| CN | 113402602 A | 9/2021 |
| EP | 0404097 A2 | 12/1990 |
| EP | 1399483 B1 | 4/2010 |
| EP | 1689782 B1 | 4/2010 |
| EP | 2235059 A1 | 10/2010 |
| EP | 1959014 B1 | 3/2011 |
| EP | 2230254 B1 | 5/2013 |
| EP | 2681239 B1 | 7/2015 |
| EP | 2032989 B2 | 10/2015 |
| EP | 2681240 B1 | 8/2017 |
| EP | 2194067 B1 | 12/2017 |
| EP | 2863947 B1 | 3/2018 |
| EP | 2714733 B1 | 1/2019 |
| EP | 1469879 B1 | 3/2019 |
| EP | 2970433 B1 | 9/2019 |
| EP | 2814500 B1 | 1/2020 |
| EP | 2322550 B1 | 4/2020 |
| EP | 3458101 B1 | 12/2020 |
| TW | 202228775 A | 8/2022 |
| WO | 8801649 A1 | 3/1988 |
| WO | 9311161 A1 | 6/1993 |
| WO | 9404678 A1 | 3/1994 |
| WO | 9425591 A1 | 11/1994 |
| WO | 03100008 A2 | 12/2003 |
| WO | 03106621 A2 | 12/2003 |
| WO | 2006060419 A2 | 6/2006 |
| WO | 2007062037 A2 | 5/2007 |
| WO | 2008005469 A2 | 1/2008 |
| WO | 2008076278 A2 | 6/2008 |
| WO | 2008079849 A2 | 7/2008 |
| WO | 2011028811 A2 | 3/2011 |
| WO | 2011161119 A1 | 12/2011 |
| WO | 2014177459 A2 | 11/2014 |
| WO | 2016064716 A1 | 4/2016 |
| WO | 2017011773 A2 | 1/2017 |
| WO | 2019084026 A1 | 5/2019 |
| WO | 2019084030 A1 | 5/2019 |
| WO | 2019173352 A1 | 9/2019 |
| WO | 2019183523 A1 | 9/2019 |
| WO | 2020006486 A1 | 1/2020 |
| WO | 2020132091 A2 | 6/2020 |
| WO | 2021041773 A1 | 3/2021 |
| WO | WO 2021/041773 * | 3/2021 |
| WO | WO 2021/243014 * | 12/2021 |
| WO | 2022081799 A1 | 4/2022 |
| WO | 2022081804 A1 | 4/2022 |
| WO | 2022187510 A1 | 9/2022 |
| WO | 2023001917 A1 | 1/2023 |
| WO | 2023019171 A1 | 2/2023 |
| WO | 2023122714 A2 | 6/2023 |
| WO | 2023133485 A2 | 7/2023 |
| WO | 2023133486 A2 | 7/2023 |
| WO | 2023133561 A1 | 7/2023 |
| WO | 2025014774 A1 | 1/2025 |

OTHER PUBLICATIONS

International Search Report for PCT/US2022/074764 dated Nov. 4, 2022 (4 pages).
International Search Report for PCT/US2022/082214 dated Jul. 3, 2023 (6 pages).
International Search Report for PCT/US2023/060206 dated Jun. 21, 2023 (5 pages).
International Search Report for PCT/US2023/060207 dated Jun. 30, 2023 (5 pages).
International Search Report for PCT/US2024/036800 dated Dec. 12, 2024 (7 pages).
International Search Report for PCT/US2024/036803 dated Dec. 12, 2024 (8 pages).
International Search Report for PCT/US2024/045630 dated Jan. 27, 2025 (5 pages).

(56) References Cited

OTHER PUBLICATIONS

International Search Report for PCT/US2024/060579 dated Apr. 3, 2025 (6 pages).
International Search Report for PCT/US2025/010700 dated Apr. 24, 2025 (5 pages).
Partial Search Report for PCT/US2024/036800 dated Oct. 21, 2024 (13 pages).
Partial Search Report for PCT/US2024/036803 dated Oct. 21, 2024 (30 pages).
Partial Search Report for PCT/US2025/010706 dated May 13, 2025 (11 pages).
Partial Search Report for PCT/US2025/010718 dated May 12, 2025 (34 pages).
"A Randomized, Active Controlled, Safety and Tolerability Study of VRDN-001 in Participants With Thyroid Eye Disease (TED)", ClinicalTrials.gov, U.S. National Library of Medicine, May 23, 2024, NCT06384547 (8 pages).
"A Safety, Tolerability and Efficacy Study of Veligrotug (VRDN 001) in Healthy Volunteers and Participants with Thyroid Eye Disease (TED) (THRIVE)", ClinicalTrials.gov, U.S. National Library of Medicine, Dec. 3, 2021, NCT05176639 (12 pages).
"A Study Evaluating TEPEZZA® Treatment in Patients With Chronic (Inactive) Thyroid Eye Disease", ClinicalTrials.gov, U.S. National Library of Medicine, Oct. 12, 2020, NCT04583735, (9 pages).
"An Efficacy, Safety, and Tolerability Study of Veligrotug (VRDN-001), in Participants with Chronic Thyroid Eye Disease (TED)", ClinicalTrials.gov, U.S. National Library of Medicine, Nov. 14, 2023, NCT06021054 (9 pages).
"Anti-insulin-like Growth Factor-1 Receptor (IGF-1R) Antibodies in Graves' Disease and Graves' Orbitopahty (IGF1RAbsGO)", ClinicalTrials.gov, U.S. National Library of Medicine, Apr. 13, 2018, NCT03498417, (7 pages).
"Expanded Access Protocol of Teprotumumab (HZN-001) for Patients With Active Thyroid Eye Disease (EAP)", ClinicalTrials.gov, U.S. National Library of Medicine, Aug. 1, 2019, NCT04040894, (7 pages).
"International Nonproprietary Names for Pharmaceutical Substances (INN)", Who Drug Information, vol. 22, No. 4, Jan. 1, 2008 URL: https://cdn.who.int/media/docs/default-source/international-nonproprietary-names-(inn)/pl100.pdf?sfvrsn=acdb5b98_7 (57 pages).
"Teprotumumab (RV 001) Treatment in Patient with Active Thyroid Eye Disease", Clinicaltrials.gov, U.S. National Library of Medicine, Jun. 5, 2013, NCT01868997 (9 pages).
"Treatment of Graves' Orbitopathy (Thyroid Eye Disease) to Reduce Proptosis With Teprotumumab Infusions in a Randomized, Placebo-Controlled, Clinical Study (OPTIC)", ClinicalTrials.gov, U.S. National Library of Medicine, Oct. 2, 2017, NCT03298867, (11 pages).
"Treatment of Graves' Orbitopathy to Reduce Proptosis With Teprotumumab Infusions in an Open-Label Clinical Extension Study (OPTIC-X)", ClinicalTrials.gov, U.S. National Library of Medicine, Mar. 9, 2018, NCT03461211, (8 pages).
Allen, Richard C., et al., "A Perspective on the Current Role of Teprotumumab in Treatment of Thyroid Eye Disease", American Academy of Ophthalmology, vol. 128, No. 8, Aug. 2021, pp. 1125-1128, DOI: 10.1016/j.ophtha.2021.03.006, (4 pages).
Baert, Filip, et al., "Influence of Immunogenicity on the Long-Term Efficacy of Infliximab in Crohn's Disease", The New England Journal of Medicine, vol. 348, 2003, pp. 601-608, DOI: 10.1056/NEJMoa020888, (8 pages).
Beniaminovitz, Ainat, et al., "Prevention of Rejection in Cardiac Transplantation by Blockade of the Interleukin-2 Receptor with a Monoclonal Antibody", The New England Journal of Medicine, vol. 342, 2000, pp. 613-619, DOI: 10.1056/NEJM200003023420902 (7 pages).
Chen, Hong, et al., "Teprotumumab, an IGF-1R Blocking Monoclonal Antibody Inhibits TSH and IGF-1 Action in Fibrocytes", Journal of Clinical Endocrinology and Metabolism, vol. 99, No. 9, Sep. 1, 2014, pp. E1635-E1640, DOI: 10.1210/jc.2014-1580 (6 pages).
Chiou, Carolina A., et al., "Teprotumumab for the treatment of mild compressive optic neuropathy in thyroid eye disease: A report of two cases", American Journal of Ophthalmology Case Reports, vol. 22, Jun. 2021, 101075, DOI: 10.1016/j.ajoc.2021.101075, (4 pages).
Chothia, Cyrus, et al., "Canonical structures for the hypervariable regions of immunoglobulins", Journal of Molecular Biology, vol. 196, No. 4, Aug. 20, 1987, pp. 901-917, DOI: 10.1016/0022-2836(87)90412-8, (18 pages).
Chothia, Cyrus, et al., "Conformations of immunoglobulin hypervariable regions", Nature, vol. 342, Dec. 1989, pp. 877-883, DOI: 10.1038/342877a0, (7 pages).
Cui, Xuejiao, et al., "A review of TSHR- and IGF-1R-related pathogenesis and treatment of Graves; orbitopathy", Frontiers in Immunology, vol. 19, Jan. 19, 2023 (12 pages).
Dall'acqua, William F., et al., "Properties of human IgG1 s engineered for enhanced binding to the neonatal Fc receptor (FcRn)", Journal of Biological Chemistry, vol. 281, No. 33, Jun. 21, 2006 (pp. 23514-23524).
Diniz, Stefania B., et al., "Early Experience With the Clinical Use of Teprotumumab in a Heterogenous Thyroid Eye Disease Population", Ophthalmic Plastic and Reconstructive Surgery, vol. 37, No. 6, 2021, pp. 583-591, DOI: 10.1097/IOP.0000000000001959, (10 pages).
Dolgin, Elie, "IGF-1R drugs travel from cancer cradle to Graves", Nature Biotechnology, vol. 38, 2020, pp. 385-388, DOI: 10.1038/s41587-020-0481-8, (4 pages).
Dosiou, Chrysoula, et al., "Thyroid Eye Disease: Navigating the New Treatment Landscape", Journal of the Endocrine Society, vol. 5, No. 5, 2021, Author Manuscript (40 pages).
Douglas, Raymond S., et al., "Aberrant Expression of the Insulin-Like Growth Factor-1 Receptor by T Cells from Patients with Graves' Disease May Carry Functional Consequences for Disease Pathogenesis", The Journal of Immunology, vol. 178, No. 5, 2007, pp. 3281-3287, DOI: 10.4049/jimmunol.178.5.3281, (8 pages).
Douglas, Raymond S., et al., "B Cells from Patients with Graves' Disease Aberrantly Express the IGF-1 Receptor: Implications for Disease Pathogenesis", The Journal of Immunology, vol. 181, No. 8, 2008, pp. 5768-5774, DOI: 10.4049/jimmunol.181.8.5768 (8 pages).
Douglas, Raymond S., et al., "Teprotumumab for the Treatment of Active Thyroid Eye Disease", The New England Journal of Medicine, vol. 382, No. 4, 2020, pp. 341-352, DOI: 10.1056/NEJMoa1910434, (12 pages).
Douglas, Raymond S., "Teprotumumab, an insulin-like growth factor-1 receptor antagonist antibody, in the treatment of active thyroid eye disease: a focus on proptosis", Eye, vol. 33, 2019, pp. 183-190, DOI: 10.1038/s41433-018-0321-y, (8 pages).
Edmunds, Matthew Ross, "Investigation of Candidate Biomarkers in Graves' Disease and Thyroid-Associated Ophthalmopathy", University of Birmingham, 2016, (306 pages).
Foster, Kelly, et al., "6461 VRDN-003, A Full Antagonist Antibody To The IGF-1 Receptor For Thyroid Eye Disease (TED): Safety And Pharmacokinetic Results Of Subcutaneous Administration In Healthy Volunteers", Abstract, Journal of the Endocrine Society, vol. 8, Issue Supplement_1, https://pmc.ncbi.nlm.nih.gov/articles/PMC10554431/, Nov. 1, 2024 (2 pages).
Foster, Kelly, et al., "Thyroid FRI546 VRDN-001, A Full Antagonist Antibody To IGF-1 Receptor In Development For Thyroid Eye Disease (TED): Pharmacodynamic Responses In Healthy Volunteers And Patients With Active TED", Abstract, Journal of the Endocrine Society, vol. 7, Issue Supplement_1, https://pmc.ncbi.nlm.nih.gov/articles/PMC10554431/, Nov. 1, 2023 (2 pages).
Ghosh, Subrata, et al., "Natalizumab for Active Crohn's Disease", The New England Journal of Medicine, vol. 348, No. 1, Jan. 2, 2003, pp. 24-32, DOI: 10.1056/NEJMoa020732, (9 pages).
Gualberto A., et al., "Emerging role of insulin-like growth factor receptor inhibitors in oncology: early clinical trial results and future directions", Oncogene, vol. 28, No. 34, 2009, pp. 3009-3021, DOI:10.1038/onc.2009.172 (13 pages).
Herold, Kevan C., et al., "Anti-CD3 Monoclonal Antibody in New-Onset Type 1 Diabetes Mellitus", The New England Journal of Medicine, vol. 346, No. 22, May 30, 2002, pp. 1692-1698, DOI: 10.1056/NEJMoa012864, (7 pages).

(56) References Cited

OTHER PUBLICATIONS

Hoa, Neil, et al., "Nuclear Targeting of IGF-1 Receptor in Orbital Fibroblasts from Graves' Disease: Apparent Role of ADAM17", PLoS One, vol. 7, No. 4, Apr. 2012, e34173, DOI: 10.1371/journal.pone.0034173, (9 pages).

Holliger, Philipp, et al., ""Diabodies": small bivalent and bispecific antibody fragments", Proceedings of the National Academy of Sciences, vol. 90, No. 14, 1993, pp. 6444-6448, (5 pages).

Holliger, Philipp, et al., "Engineered antibody fragments and the rise of single domains", Nature Biotechnology, vol. 23, No. 9, 2005, pp. 1126-1136, DOI: 10.1038/nbt1142, (12 pages).

Jain, Amy Patel, "Teprotumumab reduces extraocular muscle and orbital fat volume in thyroid eye disease", British Journal of Ophthalmology, vol. 106, No. 2, 2020, pp. 1-7, DOI: 10.1136/bjophthalmol-2020-317806, (7 pages).

Janssen, Joseph A.M.J.L., et al., "Lessons Learned from Targeting IGF-I Receptor in Thyroid-Associated Ophthalmopathy", Cell, vol. 10, No. 2, 2021, 383, DOI: 10.3390/cells10020383, (17 pages).

Kabat, Elvin A., et al., "Unusual distributions of amino acids in complementarity determining (hypervariable) segments of heavy and light chains of immunoglobulins and their possible roles in specificity of antibody-combining sites", The Journal of Biological Chemistry, vol. 252, No. 19, 1977, pp. 6609-6616, (8 pages).

Kahaly, George J, "Management of Graves Thyroidal and Extrathyroidal Disease: An Update", The Journal of Clinical Endocrinology & Metabolism, vol. 105, No. 12, Dec. 2020, pp. 3704-3720, DOI: 10.1210/clinem/dgaa646, (17 pages).

Kamboj, et al., "Emerging Therapies in the Medical Management of Thyroid Eye Disease", Frontiers in Ophthalmology, vol. 3, 1295902, Dec. 12, 2023, DOI:10.3389/fopht.2023.1295902 (5 pages).

Keenan, Gregory F., et al., "A First-in-Human Phase 1 Randomized, Single-Ascending Dose Study of Lonigutamab, an Anit-IGF-1R Monoclonal Antibody, in Healthy Volunteers", Poster Presentation, 49th North American Neuro-Ophthalmology Society Annual Meeting, 2023, Poster # 293, (1 page).

Krieger, Christine C., et al., "Bidirectional TSH and IGF-1 Receptor Cross Talk Mediates Stimulation of Hyaluronan Secretion by Graves' Disease Immunoglobins", The Journal of Clinical Endocrinology & Metabolism, vol. 100, No. 3, Mar. 1, 2015, pp. 1071-1077, DOI: 10.1210/jc.2014-3566, (7 pages).

Krieger, Christine C., et al., "Is There Evidence for IGF1R-Stimulating Abs in Graves' Orbitopathy Pathogenesis?", International Journal of Molecular Sciences, vol. 21, No. 18, 2020, 6561, DOI: 10.3390/ijms21186561, (13 pages).

Krieger, Christine C., et al., "Thyrotropin/IGF-1 Receptor Cross Talk in Graves' Ophthalmopathy Pathogenesis", The Journal of Clinical Endocrinology & Metabolism, vol. 101, No. 6, Jun. 1, 2016, pp. 2340-2347, DOI: 10.1210/jc.2016-1315 (8 pages).

Kumar, Seema, et al., "A Stimulatory Thyrotropin Receptor Antibody Enhances Hyaluronic Acid Synthesis in Graves' Orbital Fibroblasts: Inhibition by an IGF-I Receptor Blocking Antibody", The Journal of Clinical Endocrinology & Metabolism, vol. 97, No. 5, May 1, 2012, pp. 1681-1687, DOI: 10.1210/jc.2011-2890, (7 pages).

Lanzolla, G., et al., "Putative protective role of autoantibodies against the insulin-like growth factor-1 receptor in Graves' Disease: results of a pilot study", Journal of Endocrinological Investigation, vol. 43, No. 12, 2020, pp. 1759-1768, DOI: 10.1007/s40618-020-01341-2, (10 pages).

Lathe, R., "Synthetic oligonucleotide probes deduced from amino acid sequence data: Theoretical and practical considerations", Journal of Molecular Biology, vol. 183, No. 1, May 5, 1985, pp. 1-12, DOI: 10.1016/0022-2836(85)90276-1.

Lipsky, Peter E., "Infliximab and Methotrexate in the Treatment of Rheumatoid Arthritis", The New England Journal of Medicine, vol. 343, No. 22, 2000, pp. 1594-1602, DOI: 10.1056/NEJM200011303432202, (9 pages).

Liu, Alvin Y., et al., "Chimeric mouse-human IgG1 antibody that can mediate lysis of cancer cells", Proceedings of the National Academy of Sciences, vol. 84, No. 10. May 15, 1987, pp. 3439-3443, DOI: 10.1073/pnas.84.10.3439, (5 pages).

Liu, Alvin Y., et al., "Production of a mouse-human chimeric monoclonal antibody to CD20 with potent Fc-dependent biologic activity", The Journal of Immunology, vol. 139, No. 10, Nov. 15, 1987, pp. 3521-3526, DOI: 10.4049/jimmunol.139.10.3521, (7 pages).

Liu, Clarence, et al., "Randomised, double blind, placebo controlled study of interferon ß-1a in relapsing-remitting multiple sclerosis analysed by area under disability/time curves", Journal of Neurology, Neurosurgery & Psychiatry, vol. 67, No. 4, 1999, pp. 451-456, DOI: 10.1136/jnnp.67.4.451, (6 pages).

Ludgate, Marian, "Fibrosis in dysthyroid eye disease", EYE, vol. 34, No. 2, Dec. 16, 2019 (pp. 279-284).

Marinó, M., et al., "Serum antibodies against the insulin-like growth factor-1 receptor (IGF-1R) in Graves' disease and Graves' orbitopathy", Journal of Endocrinological Investigation, vol. 42, 2019, pp. 471-480, DOI: 10.1007/s40618-018-0943-8, (10 pages).

Markham, Anthony, "Teprotumumab: First Approval", Drugs, vol. 80, No. 5, 2020, pp. 509-512, DOI: 10.1007/s40265-020-01287-y, (4 pages).

Marks, James D., et al., "By-passing Immunization: Human Antibodies from V-gene Libraries Displayed on Phage", Journal of Molecular Biology, vol. 222, 1991, pp. 581-597 (17 pages).

Milgrom, Henry, et al., "Treatment of Allergic Asthma with Monoclonal Anti-IgE Antibody", The New England Journal of Medicine, vol. 341, 1999, pp. 1966-1973, DOI: 10.1056/NEJM199912233412603, (8 pages).

Morgan, Sarah L., et al., "Thyrotropin and Insulin-Like Growth Factor 1 Receptor Crosstalk Upregulates Sodium-Iodide Symporter Expression in Primary Cultures of Human Thyrocytes", Thyroid, vol. 26, No. 12, 2016, DOI: 10.1089/thy.2016.0323, (10 pages).

Morrison, Sherie L., et al., "Chimeric human antibody molecules: Mouse antigen-binding domains with human constant region domains", Proceedings of the National Academy of Sciences USA, Immunology, vol. 81, Nov. 1984, pp. 6851-6855 (5 pages).

Mueller, John P., et al., "Humanized porcine VCAM-specific monoclonal antibodies with chimeric lgG2/G4 constant regions block human leukocyte binding to porcine endothelial cells", Molecular Immunology, vol. 34, No. 6, Apr. 1997, pp. 441-452, DOI: 10.1016/S0161-5890(97)00042-4, (12 pages).

Muyldermans, Serge, et al., "Recognition of antigens by single-domain antibody fragments: the superfluous luxury of paired domains", Trends in Biochemical Sciences, vol. 26, No. 4, Apr. 1, 2001, pp. 230-235, DOI: 10.1016/s0968-0004(01)01790-x, (6 pages).

Neumann, Susanne, et al., "Targeting TSH and IGF-1 Receptors to Treat Thyroid Eye Disease", European Thyroid Journal, vol. 9, No. 1,Nov. 2, 2020, pp. 59-65, DOI: 10.1159/000511538, (7 pages).

Osher, Eliot, et al., "Therapeutic Targeting of the IGF Axis", Cells, vol. 8, No. 8, 2019, 895, DOI: 10.3390/cells8080895, (25 pages).

Ozzello, Daniel J., et al., "Early experience with teprotumumab for chronic thyroid eye disease", American Journal of Ophthalmology Case Reports, vol. 19, 2020, 100744, DOI: 10.1016/j.ajoc.2020.100744, (3 pages).

Patel, Amy, et al., "A New Era in the Treatment of Thyroid Eye Disease", American Journal of Ophthalmology, vol. 208, Aug. 1, 2019 (pp. 281-288).

Place, Robert F., et al., "Inhibiting thyrotropin/insulin-like growth factor 1 receptor crosstalk to treat Graves' ophthalmopathy: studies in orbital fibroblasts in vitro", British Journal of Pharmacology, vol. 174, No. 4, 2017, pp. 328-340, DOI: 10.1111/bph. 13693, (13 pages).

Plückthun, A., "Antibodies from *Escherichia coli*", In: Rosenberg, M., Moore, G.P. (eds) The Pharmacology of Monoclonal Antibodies. Handbook of Experimental Pharmacology, vol. 13, 1994, Springer, Berlin, Heidelberg, (48 pages).

Portielje, Johanna E., et al., "IL-12: a promising adjuvant for cancer vaccination", Cancer Immunology, Immunotherapy, vol. 52, 2003, pp. 133-144, DOI: 10.1007/s00262-002-0356-5, (12 pages).

Presta, Leonard G., "Selection, design, and engineering of therapeutic antibodies", Journal of Allergy and Clinical Immunology, vol. 116, No. 4, Oct. 2005, pp. 731-736, DOI: 10.1016/j.jaci.2005.08.003, (6 pages).

(56) References Cited

OTHER PUBLICATIONS

Pritchard, Jane, et al., "Immunoglobulin Activation of T Cell Chemoattractant Expression in Fibroblasts from Patients with Graves' Disease Is Mediated Through the Insulin-Like Growth Factor I Receptor Pathway", The Journal of Immunology, vol. 170, No. 12, 2003, pp. 6348-6354, DOI: jimmunol. 170.12.6348, (8 pages).

Riechmann, Lutz, et al., "Reshaping human antibodies for therapy", Nature, vol. 332, 1988, pp. 323-327, DOI: 10.1038/332323a0 (5 pages).

Riechmann, Lutz, et al., "Single domain antibodies: comparison of camel VH and camelised human VH domains", Journal of Immunological Methods, vol. 231, No. 1-2, Dec. 10, 1999, pp. 25-38, DOI: 10.1016/S0022-1759(99)00138-6, (14 pages).

Robbie, Gabriel J., et al., "A Novel Investigational Fc-Modified Humanized Monoclonal Antibody, Motavizumab-YTE, Has an Extended Half-Life in Healthy Adults", Antimicrobial Agents and Chemotherapy, vol. 57, No. 12, Sep. 30, 2013 (pp. 6147-6153).

Safo, Myra B., et al., "A case of ulcerative colitis associated with teprotumumab treatment for thyroid eye disease", American Journal of Ophthalmology Case Reports, vol. 22, Jun. 2021, 101069, DOI: 10.1016/j.ajoc.2021.101069, (4 pages).

Salvi, M., et al., "Medical Treatment of Graves' Orbitopathy", Hormone and Metabolic Research, vol. 47, No. 10, 2015, pp. 779-788, DOI: 10.1055/s-0035-1554721, (10 pages).

Salvi, Mario, "Immunotherapy for Graves' ophthalmopathy", Current Opinion in Endocrinology & Diabetes and Obesity, vol. 21, No. 5, Oct. 2014, pp. 409-414, DOI: 10.1097/MED.0000000000000097, Abstract (1 page).

Slamon, Dennis J., et al., "Use of Chemotherapy plus a Monoclonal Antibody against HER2 for Metastatic Breast Cancer That Overexpresses HER2", The New England Journal of Medicine, vol. 344, No. 11, Mar. 15, 2001, pp. 783-792, DOI: 10.1056/NEJM200103153441101, (10 pages).

Slentz, Dane H., et al., "Teprotumumab: a novel therapeutic monoclonal antibody for thyroid-associated ophthalmopathy", Expert Opinion on Investigational Drugs, vol. 29, No. 7, pp. 645-649, DOI: 10.1080/13543784.2020.1772752, (20 pages).

Smith, Terry J., et al., "Immunoglobulins from Patients with Graves' Disease Induce Hyaluronan Synthesis in Their Orbital Fibroblasts through the Self-Antigen, Insulin-Like Growth Factor-I Receptor", The Journal of Clinical Endocrinology & Metabolism, vol. 89, No. 10, Oct. 1, 2004, pp. 5076-5080, DOI: 10.1210/jc.2004-0716, (5 pages).

Smith, Terry J., "Teprotumumab as a Novel Therapy for Thyroid-Associated Ophthalmopathy", Frontiers in Endocrinology, vol. 11, 2020, DOI: 10.3389/fendo.2020.610337, (10 pages).

Smith, Terry J., et al., "Teprotumumab for Thyroid-Associated Ophthalmopathy", The New England Journal of Medicine, vol. 376, N. 18, 2017, pp. 1748-1761, DOI: 10.1056/NEJMoa1614949, (14 pages).

Storz, Ulrich, "Intellectual property protection", mAbs, vol. 3, No. 3, 2011, pp. 310-317, DOI: 10.4161/mabs.3.3.15530, (9 pages).

Taylor, Peter N., et al., "New insights into the pathogenesis and nonsurgical management of Graves orbitopathy", Nature Reviews Endocrinology, vol. 16, No. 2, 2020, pp. 104-116, DOI: 10.1038/s41574-019-0305-4, (13 pages).

Tsui, Shanli, et al., "Evidence for an Association between Thyroid-Stimulating Hormone and Insulin-Like Growth Factor 1 Receptors: A Tale of Two Antigens Implicated in Graves' Disease", The Journal of Immunology, vol. 181, No. 6, Sep. 15, 2008, DOI: 10.4049/jimmunol.181.6.4397, (10 pages).

Tsurushita, Naoya, et al., "Humanization of a chicken anti-IL-12 monoclonal antibody", Journal of Immunological Methods, vol. 295, No. 1-2, Dec. 2004, pp. 9-19, DOI: 10.1016/j.jim.2004.08.018, (11 pages).

Ugradar, Shoaib, et al., "A Paradigm Shift in the Management of Thyroid Eye Disease How Teprotumumab Has Changed the Therapeutic Interface.", Journal of neuro-ophthalmology: the official journal of the North American Neuro-Ophthalmology Society, vol. 42, No. 1, Mar. 2022, pp. 26-34, (Abstract Only), DOI:10.1097/WNO.0000000000001515 (2 pages).

Ugradar, Shoaib, et al., "Improvement of asymmetric thyroid eye disease with teprotumumab", British Journal of Ophthalmology, 2021, DOI: 10.1136/bjophthalmol-2020-318314, (5 pages).

Ugradar, Shoaib, et al., "Teprotumumab for non-inflammatory thyroid eye disease (TED): evidence for increased IGF-1R expression", Eye, vol. 35, No. 9, 2021, pp. 2607-2612, DOI: 10.1038/s41433-020-01297-w, (6 pages).

Ugradar, Shoaib, et al., "Teprotumumab for the treatment of chronic thyroid eye disease", Eye (London, England), vol. 36, No. 8, Aug. 2022, pp. 1553-1559, DOI:10.1038/s41433-021-01593-z (7 pages).

Weightman, David R., et al., "Autoantibodies to Igf-1 Binding Sites in Thyroid Associated Ophthalmopathy", Autoimmunity, vol. 16, No. 4, 1993, pp. 251-257, DOI: 10.3109/08916939309014643, (7 pages).

Xin, Yan, et al., "Pharmacokinetics and Exposure-Response Relationship of Teprotumumab, an Insulin-Like Growth Factor-1 Receptor-Blocking Antibody, in Thyroid Eye Disease", Clinical Pharmacokinetics, vol. 60, 2021, pp. 1029-1040, DOI: 10.1007/s40262-021-01003-3, (12 pages).

Yang, James C., et al., "A Randomized Trial of Bevacizumab, an Anti-Vascular Endothelial Growth Factor Antibody, for Metastatic Renal Cancer", The New England Journal of Medicine, vol. 349, No. 5, Jul. 31, 2003, pp. 427-434, DOI: 10.1056/NEJMoa021491, (8 pages).

Yu, Run, "Thyroid function suppression after initiation of teprotumumab treatment", Endocrine, vol. 73, No. 3, 2021, pp. 561-562, DOI: 10.1007/s12020-021-02676-3, (2 pages).

* cited by examiner

IGF1R Cell-based binding

IGF1R Antagonism

IGF1R Cell-based binding

IGF1R Antagonism

Total Cell Surface Receptor Binding
A549 cells (1 hour, 4°C)

mAb concentration (nM)

Cell Surface Receptor Binding After Internalization
A549 cells (1 hour, 37°C)

mAb concentration (nM)

Mean proptosis change from baseline across anti-IGF-1R studies at week 6

Proptosis response rate at week 6

Median time to protosis response
(weeks)

Mean time to overall response
(weeks)

CAS 0 or 1 at week 6
(% CAS 0 or 1)

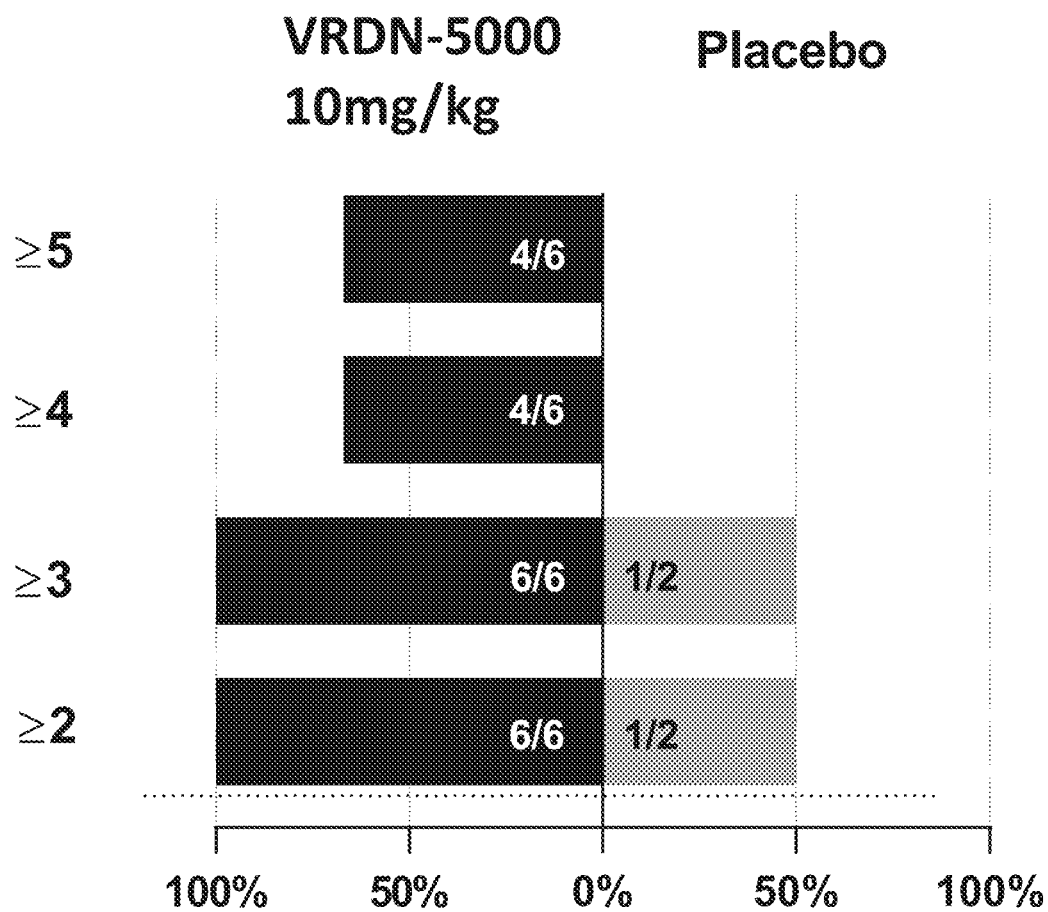

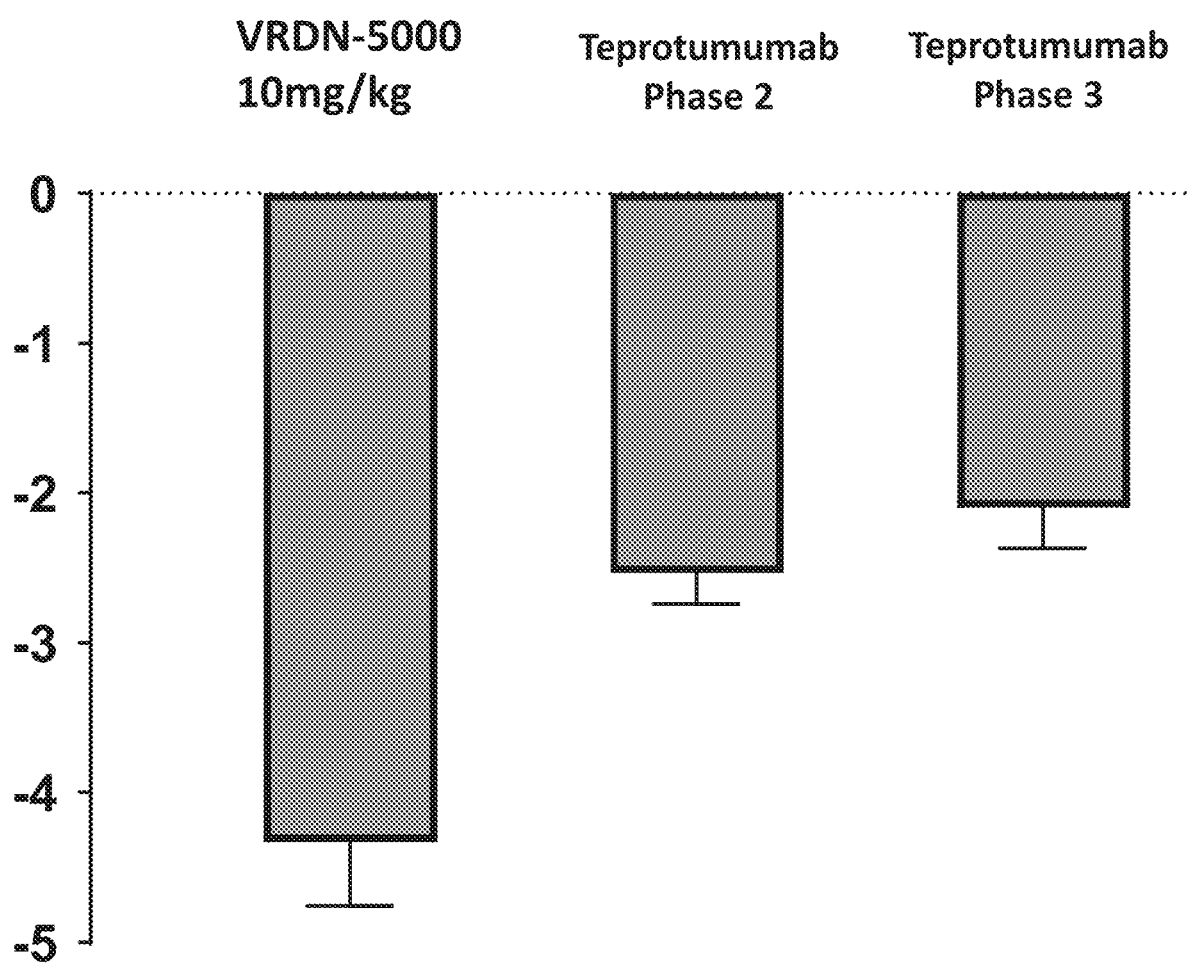

CAS of 0 or 1 at week 6

Diplopia resolution (Week 6)

```
                        SEQUENCE LISTING

Sequence total quantity: 13
SEQ ID NO: 1            moltype =   length =
SEQUENCE: 1
000

SEQ ID NO: 2            moltype = AA  length = 113
FEATURE                 Location/Qualifiers
source                  1..113
                        mol_type = protein
                        organism = synthetic construct
SEQUENCE: 2
DVVMTQTPLS LPVSLGDPAS ISCRSSQSIV HSNVNTYLEW YLQKPGQSPR LLIYKVSNRF   60
SGVPDRFSGS GAGTDFTLRI SRVEAEDLGI YYCFQGSHVP PTFGGGTKLE IKR         113

SEQ ID NO: 3            moltype = AA  length = 124
FEATURE                 Location/Qualifiers
source                  1..124
                        mol_type = protein
                        organism = synthetic construct
SEQUENCE: 3
QVQLVQSGAE VVKPGASVKL SCKASGYTFT SYWMHWVKQR PGQGLEWIGE INPSNGRTNY   60
NQKFQGKATL TVDKSSSTAY MQLSSLTSED SAVYYFARGR PDYYGSSKWY FDVWGQGTTV  120
TVSS                                                               124

SEQ ID NO: 4            moltype = AA  length = 16
FEATURE                 Location/Qualifiers
source                  1..16
                        mol_type = protein
                        organism = synthetic construct
SEQUENCE: 4
RSSQSIVHSN VNTYLE                                                   16

SEQ ID NO: 5            moltype = AA  length = 7
FEATURE                 Location/Qualifiers
source                  1..7
                        mol_type = protein
                        organism = synthetic construct
SEQUENCE: 5
KVSNRFS                                                              7

SEQ ID NO: 6            moltype = AA  length = 9
FEATURE                 Location/Qualifiers
source                  1..9
                        mol_type = protein
                        organism = synthetic construct
SEQUENCE: 6
FQGSHVPPT                                                            9

SEQ ID NO: 7            moltype = AA  length = 5
FEATURE                 Location/Qualifiers
source                  1..5
                        mol_type = protein
                        organism = synthetic construct
```

```
SEQUENCE: 7
SYWMH                                                                               5

SEQ ID NO: 8            moltype = AA  length = 18
FEATURE                 Location/Qualifiers
source                  1..18
                        mol_type = protein
                        organism = synthetic construct
SEQUENCE: 8
GEINPSNGRT NYNQKFQG                                                                18

SEQ ID NO: 9            moltype = AA  length = 15
FEATURE                 Location/Qualifiers
source                  1..15
                        mol_type = protein
                        organism = synthetic construct
SEQUENCE: 9
GRPDYYGSSK WYFDV                                                                   15

SEQ ID NO: 10           moltype = AA  length = 454
FEATURE                 Location/Qualifiers
source                  1..454
                        mol_type = protein
                        organism = synthetic construct
SEQUENCE: 10
QVQLVQSGAE VVKPGASVKL SCKASGYTFT SYWMHWVKQR PGQGLEWIGE INPSNGRTNY                   60
NQKFQGKATL TVDKSSSTAY MQLSSLTSED SAVYYFARGR PDYYGSSKWY FDVWGQGTTV                  120
TVSSASTKGP SVFPLAPSSK STSGGTAALG CLVKDYFPEP VTVSWNSGAL TSGVHTFPAV                  180
LQSSGLYSLS SVVTVPSSSL GTQTYICNVN HKPSNTKVDK KVEPKSCDKT HTCPPCPAPE                  240
LLGGPSVFLF PPKPKDTLMI SRTPEVTCVV VDVSHEDPEV KFNWYVDGVE VHNAKTKPRE                  300
EQYNSTYRVV SVLTVLHQDW LNGKEYKCKV SNKALPAPIE KTISKAKGQP REPQVYTLPP                  360
SRDELTKNQV SLTCLVKGFY PSDIAVEWES NGQPENNYKT TPPVLDSDGS FFLYSKLTVD                  420
KSRWQQGNVF SCSVMHEALH NHYTQKSLSL SPGK                                             454

SEQ ID NO: 11           moltype = AA  length = 219
FEATURE                 Location/Qualifiers
source                  1..219
                        mol_type = protein
                        organism = synthetic construct
SEQUENCE: 11
DVVMTQTPLS LPVSLGDPAS ISCRSSQSIV HSNVNTYLEW YLQKPGQSPR LLIYKVSNRF                   60
SGVPDRFSGS GAGTDFTLRI SRVEAEDLGI YYCFQGSHVP PTFGGGTKLE IKRTVAAPSV                  120
FIFPPSDEQL KSGTASVVCL LNNFYPREAK VQWKVDNALQ SGNSQESVTE QDSKDSTYSL                  180
SSTLTLSKAD YEKHKVYACE VTHQGLSSPV TKSFNRGEC                                        219

SEQ ID NO: 12           moltype = AA  length = 5
FEATURE                 Location/Qualifiers
source                  1..5
                        mol_type = protein
                        organism = synthetic construct
REPEAT                  1..5
SEQUENCE: 12
GGGGS                                                                               5

SEQ ID NO: 13           moltype = AA  length = 5
FEATURE                 Location/Qualifiers
source                  1..5
                        mol_type = protein
                        organism = synthetic construct
REPEAT                  1..5
SEQUENCE: 13
GGGGA                                                                               5
```

COMPOSITIONS, DOSES, AND METHODS FOR TREATMENT OF THYROID EYE DISEASE

CROSS REFERENCE TO RELATED APPLICATIONS

This application claims priority to U.S. Provisional Application No. 63/260,133, filed Aug. 10, 2021, and U.S. Provisional Application No. 63/261,744, filed Sep. 28, 2021, each of which is hereby incorporated by reference in its entirety.

REFERENCE TO SEQUENCE LISTING SUBMITTED ELECTRONICALLY

The instant application contains a Sequence Listing which has been submitted electronically in XML file format and is hereby incorporated by reference in its entirety. Said XML copy, created on Aug. 10, 2022, is named "257635_000401_ST26.xml" and is 12,855 bytes in size.

BACKGROUND

Thyroid-associated ophthalmopathy (TAO), also known as thyroid eye disease (TED), Graves' ophthalmopathy or orbitopathy (GO), thyrotoxic exophthalmos, dysthyroid ophthalmopathy, and several other terms, is orbitopathy associated with thyroid dysfunction. TAO is divided into two types. Active TAO, which typically lasts 1-3 years, is characterized by an ongoing autoimmune/inflammatory response in the soft tissues of the orbit. Active TAO is responsible for the expansion and remodeling of the ocular soft tissues. The autoimmune/inflammatory response of active TAO spontaneously resolves and the condition transitions into inactive TAO. Inactive TAO is the term used to describe the long-term/permanent sequelae of active TAO. The cause of TAO is unknown. TAO is typically associated with Graves' hyperthyroidism, but can also occur as part of other autoimmune conditions that affect the thyroid gland and produce pathology in orbital and periorbital tissue, and, rarely, the pretibial skin (pretibial myxedema) or digits (thyroid acropachy). TAO is an autoimmune orbitopathy in which the orbital and periocular soft tissues are primarily affected with secondary effects on the eye and vision. In TAO, as a result of inflammation and expansion of orbital soft tissues, primarily eye muscles and adipose, the eyes are forced forward (bulge) out of their sockets—a phenomenon termed proptosis or exophthalmos. Although most cases of TAO do not result in loss of vision, this condition can cause vision-threatening exposure keratopathy, troublesome diplopia (double vision), and compressive dysthyroid optic neuropathy. TAO may precede, coincide with, or follow the systemic complications of dysthyroidism. The ocular manifestations of TAO include upper eyelid retraction, lid lag, swelling, redness (erythema), conjunctivitis, and bulging eyes (exophthalmos or proptosis), chemosis, periorbital edema, and altered ocular motility with significant functional, social, and cosmetic consequences. Many of the signs and symptoms of TAO, including proptosis and ocular congestion, result from expansion of the orbital adipose tissue and periocular muscles. The adipose tissue volume increases owing in part to new fat cell development (adipogenesis) within the orbital fat. The accumulation of hydrophilic glycosaminoglycans, primarily hyaluronic acid, within the orbital adipose tissue and the perimysial connective tissue between the extraocular muscle fibers, further expands the fat compartments and enlarges the extraocular muscle bodies. Hyaluronic acid is produced by fibroblasts residing within the orbital fat and extraocular muscles, and its synthesis in vitro is stimulated by several cytokines and growth factors, including IL-1beta, interferon-gamma, platelet-derived growth factor, thyroid stimulating hormone (TSH) and insulin-like growth factor I (IGF-I).

Antibodies that activate the insulin-like growth factor I receptor (IGF-IR) have also been detected and implicated in active TAO. Without being bound to any theory, it is believed that TSHR and IGF-IR form a physical and functional complex in orbital fibroblasts, and that blocking IGF-IR appears to attenuate both IGF-1 and TSH-dependent signaling. It has been suggested that blocking IGF-IR using an antibody antagonist might reduce both TSHR- and IGF-I-dependent signaling and therefore interrupt the pathological activities of autoantibodies acting as agonists on either receptor.

IGF-IR is a widely expressed heterotetrameric protein involved in the regulation of proliferation and metabolic function of many cell types. It is a tyrosine kinase receptor comprising two subunits. IGF-IRalpha contains a ligand-binding domain while IGF-IRbeta is involved in signaling and contains tyrosine phosphorylation sites.

Current therapies for hyperthyroidism due to Graves' disease are imperfect because therapies targeting the specific underlying pathogenic autoimmune mechanisms of the disease are lacking. Even more complex is the treatment of moderate-to-severe active TAO. Although recent years have witnessed a better understanding of its pathogenesis, TAO remains a therapeutic challenge and dilemma. There are no approved drugs to treat active TAO. Intravenous glucocorticoids (ivGCs) and oral glucocorticoids are used to treat patients with moderate-to-severe active TAO, but results are seldom satisfactory. Partial responses are frequent and relapses (rebound) after drug withdrawal are not uncommon. Adverse events do occur and many patients eventually require rehabilitative surgery conducted when their condition has transitioned to inactive TAO. Accordingly, there is still a need to provide alternative therapies for TAO and its related symptoms.

SUMMARY

The disclosure relates generally to IGF-1R antibodies, and antigen binding fragments thereof and uses thereof. Certain IGF-1R antibodies and antigen-binding fragments inhibit IGF-1R function or block the biological functions of IGF-I mediated IGF-1R signaling. Additionally, the invention generally relates to methods for treating thyroid-associated ophthalmopathy (TAO), also known as thyroid eye disease (TED), Graves' ophthalmopathy or orbitopathy (GO), thyrotoxic exophthalmos, dysthyroid ophthalmopathy, and other thyroid eye disorders associated with IGF-1R signaling.

In some embodiments, the disclosure provides a method of treatment comprising treating thyroid associated ophthalmopathy in a subject in need thereof, comprising: intravenously or subcutaneously administering a first dose, wherein the first dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg, of an antibody to the subject, and intravenously or subcutaneously administering one or more subsequent doses, wherein each subsequent dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg of the antibody to the subject, wherein the antibody is as provided for herein.

In some embodiments, the present disclosure provides a method of treating thyroid associated ophthalmopathy in a subject in need thereof comprising: intravenously or subcutaneously administering a first dose, wherein the first dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg, of an antibody to the subject, and intravenously or subcutaneously administering one or more subsequent doses, wherein each subsequent dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg of the antibody to the subject, wherein the antibody is as provided for herein wherein the one or more subsequent doses is administered when the subject does not have an adequate response to one or more prior doses, as determined by measurement of clinical activity score and/or proptosis.

In some embodiments, the present disclosure provides a first dose of about 2 mg/kg, about 3 mg/kg, about 2.5 mg/kg, about 5 mg/kg, about 7.5 mg/kg, about 10 mg/kg, about 15 mg/kg, or about 20 mg/kg.

In some embodiments, at least one subsequent dose of the one or more subsequent doses is about 2 mg/kg, about 3 mg/kg, about 5 mg/kg, about 7.5 mg/kg, about 10 mg/kg, about 15 mg/kg, or about 20 mg/kg.

In some embodiments, the first dose is about 10 mg/kg. In some embodiments, the one ore more subsequent doses are about 10 mg/kg.

In some embodiments, the present disclosure provides methods comprising further administering one or more loading doses of the antibody to the subject before administering the first dose.

In some embodiments, the present disclosure provides methods comprising further administering a first loading dose of the antibody to the subject, before administering the first dose, wherein the first loading dose is selected from the group consisting of about 5 mg/kg to about 7.5 mg/kg, about 7.5 mg/kg to about 10 mg/kg, about 10 mg/kg to about 12.5 mg/kg, or about 12.5 mg/kg to about 15 mg/kg.

In some embodiments, the first loading dose is about 5 mg/kg, 7.5 mg/kg, 10 mg/kg, 12.5 mg/kg, 15 mg/kg, or 20 mg/kg.

In some embodiments, the second loading dose is about 5 mg/kg, 7.5 mg/kg, 10 mg/kg, 12.5 mg/kg, 15 mg/kg, or 20 mg/kg.

In some embodiments, the present disclosure provides a method of improving a treatment of thyroid associated ophthalmopathy in a subject previously administered one or more treatments comprising: intravenously or subcutaneously administering at least one dose consisting of about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg, of an antibody to the subject, wherein the antibody is an antibody as provided for herein, such as, wherein the antibody comprises a heavy chain and a light chain, wherein the heavy chain comprises a HCDR1 of SEQ ID NO: 7, a HCDR2 of SEQ ID NO: 8, and a HCDR3 of SEQ ID NO: 9 and the light chain comprises a LCDR1 of SEQ ID NO: 4, a LCDR2 of SEQ ID NO: 5 and a LCDR3 of SEQ ID NO: 6; or wherein the antibody comprises a light chain comprising a variable region having the amino acid sequence of SEQ ID NO: 2 and a heavy chain comprises a variable region sequence having the amino acid sequence of SEQ ID NO: 3; or wherein the antibody comprises a light chain comprising an amino acid sequence of SEQ ID NO: 11 and a heavy chain comprising an amino acid sequence of SEQ ID NO: 10, wherein the at least one dose results in an improvement on one or more measurements relative to one or more measurements prior to the at least one dose.

In some such embodiments, the one or more measurements is selected from proptosis, CAS, level of deterioration in the other eye, Score on GO-QoL, and combinations thereof.

In some embodiments, if the subject does not have a satisfactory response after the at least one dose, the subject is administered one or more subsequent doses each selected from the group consisting of about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg of the antibody to the subject.

In some embodiments, the one or more subsequent doses improves one or of proptosis, CAS, level of deterioration in the other eye, Score on GO-QoL, and combinations thereof, as compared to prior to the one or more subsequent doses.

The present disclosure provides a method of treating thyroid associated ophthalmopathy in a subject in need thereof, comprising: intravenously or subcutaneously administering a first dose, wherein the first dose is selected from the group consisting of: about 250 mg, about 300 mg, about 350 mg, or about 400 mg of an antibody to the subject, and intravenously or subcutaneously administering one or more subsequent doses, wherein each subsequent dose is selected from the group consisting of: about 250 mg, about 300 mg, about 350 mg, or about 400 mg of the antibody to the subject, wherein the antibody is as provided for herein.

As used herein, an antibody is provided for herein, can be comprise a heavy chain and light chain. In some embodiments, the antibody comprises a light chain comprising an amino acid sequence of SEQ ID NO: 11 and a heavy chain comprising an amino acid sequence of SEQ ID NO: 10. In some embodiments, the heavy chain can comprise a Fc mutation, such as M252Y, S254T, and T256E mutation in the Fc domain. In some embodiments, the heavy chain comprises a VH having an amino acid sequence of SEQ ID NO: 3. In some embodiments, the light chain comprises a VL comprising an amino acid sequence of SEQ ID NO: 2. Accordingly, in some embodiments, the antibody comprises a VL of SEQ ID NO: 2 and a VH of SEQ ID NO: 3. In some embodiments, the antibody comprises a heavy variable region (VH) comprising a HCDR1 of SEQ ID NO: 7, a HCDR2 of SEQ ID NO: 8, and a HCDR3 of SEQ ID NO: 9 and a light variable region (VL) comprising a LCDR1 of SEQ ID NO: 4, a LCDR2 of SEQ ID NO: 5 and a LCDR3 of SEQ ID NO: 6.

In some embodiments, the first dose is about 250 mg, 300 mg, 350 mg, or 400 mg.

In some embodiments, the one or more subsequent doses is about 250 mg, 300 mg, 350 mg, or 400 mg.

In some embodiments, the present disclosure provides methods comprising further administering one or more loading doses of the antibody to the subject before administering the first dose.

In some embodiments, the present disclosure provides methods comprising further administering a first loading dose of the antibody to the subject, before administering the first dose, wherein the first loading dose is selected from the group consisting of about 250 mg, 300 mg, 350 mg, or 400 mg.

In some embodiments, the first loading dose is about 250 mg, 300 mg, 350 mg, or 400 mg.

In some embodiments, the second loading dose is about 250 mg, 300 mg, 350 mg, or 400 mg.

In some embodiments, the one or more subsequent doses is the same as the first dose amount.

In some embodiments, the one or more subsequent dose amounts is different from the first dose amount.

In some embodiments, at least one subsequent dose of the one or more subsequent doses is administered one, two, three, four, five, six, or eight weeks after the first dose.

In some embodiments, only one, two, three, four, five, six or seven subsequent doses are administered to the subject.

In some embodiments, a total of two, three, four, five, six, seven or eight doses is administered to the subject.

In some embodiments, after two or three doses of the antibody, the clinical activity score of the subject is reduced.

In some embodiments, each subsequent dose is administered one, two, three, four, five, six, seven, or eight weeks after a previous dose.

In some embodiments, at least one dose is administered by intravenous infusion over 45 minutes to about 90 minutes, or over 60 minutes to about 90 minutes.

In some embodiments, at least one dose by subcutaneous administration. In some such embodiments, the subcutaneous administration is self-administered.

In some embodiments, a second loading dose of the antibody is administered to the subject after the first loading dose, and wherein the first and second loading doses are administered before the first dose.

In some embodiments, the first loading dose and the second loading doses are the same dose amount.

In some embodiments, the first loading dose and the second loading dose are different dose amounts.

In some embodiments, the first loading dose is administered to the subject one, two, three, or four weeks before the first dose is administered.

In some embodiments, the antibody is administered as part of a pharmaceutically acceptable composition comprising the antibody and at least one pharmaceutically acceptable excipient, wherein the antibody has at least about 150 mg/ml solubility in the pharmaceutically acceptable composition.

In some embodiments, the subject has had an unsatisfactory response to a prior therapeutic for the thyroid associated ophthalmopathy. In some such embodiments, the unsatisfactory response is one or more of: failure to reduce proptosis by 2 mm or more; failure to reduce CAS on one or more components or by 2 or more points; deterioration of 2 mm or more in the other eye; failure to reduce diplopia; failure to continue to improve diplopia for a period of time; failure to improve a score on Graves' Ophthalmopathy Quality of Life (GO-QoL) assessment by 8 or more points; and combinations thereof.

In some embodiments, the first loading dose and the second loading dose are administered between about one, about two, or about three weeks apart.

In some embodiments, the second loading dose is administered about one, about two, or about three weeks before the first dose.

In some embodiments, methods of treating thyroid associated ophthalmopathy in a subject in need thereof are provided, the method comprising intravenously administering a first dose of 10 mg/kg of an antibody to the subject, wherein the antibody comprises a heavy chain and a light chain, wherein the heavy chain comprises a HCDR1 of SEQ ID NO: 7, a HCDR2 of SEQ ID NO: 8, and a HCDR3 of SEQ ID NO: 9 and the light chain comprises a LCDR1 of SEQ ID NO: 4, a LCDR2 of SEQ ID NO: 5 and a LCDR3 of SEQ ID NO: 6.

In some embodiments, the method further comprises administering a subsequent dose of about 10 mg/kg. In some embodiments, the subsequent dose is administered about 3 weeks after the first dose. In some embodiments, the method further comprises administering a subsequent dose of about 10 mg/kg every 3 weeks after the first dose. In some embodiments, the subsequent dose is administered every 3 weeks for a total of 4 subsequent doses. In some embodiments, the subsequent dose is administered every 3 weeks for a total of 7 subsequent doses. In some embodiments, the subject has a reduction in proptosis and an improvement in CAS score within 3 weeks or within 6 weeks of the first dose.

BRIEF DESCRIPTION OF THE DRAWING

FIG. 12A-C illustrate various embodiments as provided for herein.

FIG. 13A-B illustrate various embodiments as provided for herein.

DETAILED DESCRIPTION

Figure 1A:
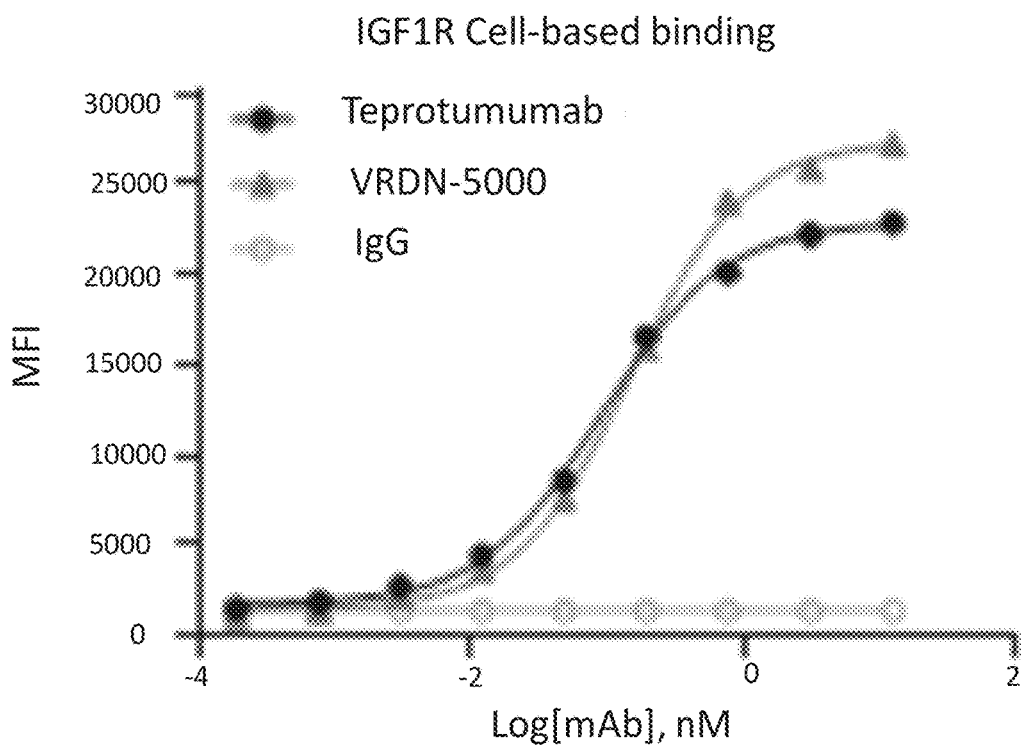
FIG. 1A-D illustrates various embodiments as provided for herein.

Provided herein are antibodies that bind and modulate the activity of IGF-1R. The antibodies can be used, for example, to treat thyroid eye disease.

As used herein, "Thyroid-associated Ophthalmopathy" (TAO), "Thyroid Eye Disease" (TED), "Graves' Ophthalmopathy" or "Graves' Orbitopathy" (GO) refer to the same disorder or condition and are used interchangeably. They all refer to the inflammatory orbital pathology associated with some autoimmune thyroid disorders, most commonly with "Graves' Disease" (GD), but sometimes with other diseases, e.g. Hashimoto's thyroiditis.

The terms "proptosis" and "exophthalmos" (also known as exophthalmus, exophthalmia, or exorbitism) refer to the forward projection, displacement, bulging, or protrusion of an organ. As used herein, the terms refer to the forward projection, displacement, bulging, or protrusion of the eye anteriorly out of the orbit. Proptosis and exophthalmos are considered by some of skill in the art to have the same meaning and are often used interchangeably, while others attribute subtle differences to their meanings. Exophthalmos is used by some to refer to severe proptosis; or to refer to endocrine-related proptosis. Yet others use the term exophthalmos when describing proptosis associated with the eye, in, for example, subjects with TAO (TED or GO).

As used herein, the terms "proptosis" and "exophthalmos" are used interchangeably and refer to the forward projection, displacement, bulging, or protrusion of the eye anteriorly out of the orbit. Owing to the rigid bony structure of the orbit with only anterior opening for expansion, any increase in orbital soft tissue contents taking place from the side or from behind will displace the eyeball forward. Proptosis or exophthalmos can be the result of a several disease processes including infections, inflammations, tumors, trauma, metastases, endocrine lesions, vascular diseases & extra orbital lesions. TAO (TED or GO) is currently recognized as the most common cause of proptosis in adults. Exophthalmos can be either bilateral, as is often seen in TAO (TED or GO), or unilateral (as is often seen in an orbital tumor).

Measurement of the degree of exophthalmos can be performed using, for example, an exophthalmometer, an instrument used for measuring the degree of forward displacement of the eye. The device allows measurement of the forward distance of the lateral orbital rim to the front of the cornea. Computed tomography (CT) scanning and Magnetic resonance imaging (MRI) may also be used in evaluating the degree of exophthalmos or proptosis. CT scanning is an excellent imaging modality for the diagnosis of TAO. In addition to allowing visualization of the enlarged extraocular muscles, CT scans provide the surgeon or clinician with depictions of the bony anatomy of the orbit when an orbital decompression is required. MRI, with its multi-planar and inherent contrast capabilities, provides excellent imaging of the orbital contents without the radiation exposure associated with CT scan studies. MRI provides better imaging of the optic nerve, orbital fat, and extraocular muscle, but CT scans provide better views of the bony architecture of the orbit. Orbital ultrasonography can also be a used for the diagnosis and evaluation of TAO, because it can be performed quickly and with a high degree of confidence. High reflectivity and enlargement of the extraocular muscles are assessed easily, and serial ultrasonographic examinations can also be used to assess progression or stability of the ophthalmopathy. Based on the technologies currently available, or that will become available in the future, one of skill in the art would be capable of determining the best modality for diagnosing and evaluating the extent of proptosis or exophthalmos.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

In some embodiments, the antibodies, or antigen fragments herein, comprise a Fc region. In some embodiments, the Fc region comprises a mutation that extends the half-life of the antibody when linked to the Fc region. In some embodiments, the Fc region comprises a S228P, L235E, M252Y, S254T, T256E, M428L, N434S, L234F, P331S mutation, or any combination thereof. In some embodiments, the Fc region comprises a M252Y, S254T, and T256E mutations. In some embodiments, the Fc region comprises a S228P and a L235E mutation. In some embodiments, the antibody comprises a L234F, L235E, and P331S mutation. In some embodiments, the Fc region comprises M252Y, S254T, T256E, S228P and L235E mutations. In some embodiments, the Fc region comprises S228P, L235E, M428L, and N434S mutations. In some embodiments, the Fc region comprises the M428L and N434S mutations. In some embodiments, the Fc region comprises the L234F, L235E, P331S, M252Y, S254T, and T256E mutations. Mutations in the Fc region are also described in US2007041972A1, EP2235059B1, U.S. Pat. No. 8,394,925, and Mueller et al, Mol Immunol 1997 April; 34 (6): 441-52, each of which is incorporated by reference in its entirety. The numbering referenced herein refers to the Kabat numbering system for the Fc region.

A "Fab' fragment" contains one light chain and a portion or fragment of one heavy chain that contains the VH domain and the CHI domain and also the region between the CHI and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90:6444-6448. For a review of engineered antibody variants generally see Holliger and Hudson (2005) *Nat. Biotechnol.* 23:1126-1136.

Typically, a variant antibody or antigen binding fragment of the antibodies provided herein retain at least 10% of its IGF-1R binding activity (when compared to a parental antibody that is modified) when that activity is expressed on a molar basis. In some embodiments, a variant antibody (or antigen fragment thereof), or antigen binding fragment of an antibody provided herein, retains at least 20%, 50%, 70%, 80%, 90%, 95% or 100% or more of the IGF-1R binding affinity as the parental antibody. As described herein, it is also intended that an antibody or antigen binding fragment of the invention can include conservative or non-conservative amino acid substitutions, which can also be referred to as "conservative variants" or "function conserved variants" of the antibody, that do not substantially alter its biologic activity.

"Isolated antibody" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example. See also Presta (2005) *J. Allergy Clin. Immunol.* 116:731.

As used herein, a "chimeric antibody" is an antibody having the variable domain from a first antibody and constant domain from a second antibody, where the first and second antibodies are from different species. (U.S. Pat. No. 4,816,567; and Morrison et al., (1984) *Proc. Natl. Acad. Sci. USA* 81:6851-6855). Typically the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g. rodent) antibody.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) *J. Mol. Biol.* 196:901-917. As used herein, the term "framework" or "FR" residues refers to those variable domain residues other than the hypervariable region residues defined herein as CDR residues. CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived.

Additionally, in some embodiments, the antibodies can take the form of a full length antibody, single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; a Microbody; a peptide aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; Affimers, a DuoBody, a Fv, a Fab, a Fab', a F(ab')2, a peptide mimetic molecule, or a synthetic molecule, as described in US Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of each of which are hereby incorporated by reference in their entireties. See also, Storz MAbs. 2011 May-June; 3(3): 310-317, which is hereby incorporated by reference.

The term "antigen" as used herein means any molecule that has the ability to generate antibodies either directly or indirectly or that binds to antibody. Included within the definition of "antigen" is a protein-encoding nucleic acid. An "antigen" can also refer to the binding partner of an antibody. In some embodiments, the antigen is the IGF-1R protein expressed on the surface of a cell. In some embodiments, the cell is an intact cell. An intact cell is a cell that has not been lysed or broken open with the use of detergents or other reagents. A cell that has been treated with detergents or other reagents that breaks up the cellular membrane or punches holes in a cellular membrane is not an intact cell. For example, methods are provided herein for generating an antibody that binds to a IGF-1R protein, the method comprising culturing a cell comprising a nucleic acid molecule encoding the IGF-1R antibody.

As used herein, "specific binding" or "immunospecific binding" or "binds immunospecifically" refer to antibody binding to a predetermined antigen (e.g. IGF-1R) or epitope present on the antigen. In some embodiments, the antibody binds with a dissociation constant ($K_D$)) of $10^{-7}$ M or less, and binds to the predetermined antigen with a $K_D$ that is at least two-fold less than its $K_D$ for binding to a non-specific antigen (e.g., BSA, casein, or another non-specific polypeptide) other than the predetermined antigen. The phrases "an antibody recognizing IGF-1R" and "an antibody specific for IGF-1R" are used interchangeably herein with the term "an antibody which binds immunospecifically to IGF-1R." Reference in the present disclosure may be made to IGF-1R. The degree of specificity necessary for an anti-IGF-1R antibody may depend on the intended use of the antibody, and at any rate is defined by its suitability for use for an intended purpose. In some embodiments, the antibody, or binding compound derived from the antigen-binding site of an antibody, of the contemplated method binds to its antigen (IGF-1R), with an affinity that is at least two fold greater, at least ten times greater, at least 20-times greater, or at least 100-times greater than the affinity with any other antigen.

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

The term "homolog" means protein sequences having between 40% and 100% sequence homology or identity to a reference sequence. Percent identity between two peptide chains can be determined by pair wise alignment using the default settings of the AlignX module of Vector NTI v.9.0.0 (Invitrogen Corp., Carslbad, Calif.). In some embodiments, the antibody, or antigenic binding fragment thereof has, at least 50, 60, 70, 80, 90, 91, 92, 93, 94, 95, 96, 97, 98, or 99% homology or identity to a sequence described herein. In some embodiments, the antibody has conservative substitutions as compared to a sequence described herein. Exemplary conservative substitutions are illustrated in Table 1 and are encompassed within the scope of the disclosed subject matter. The conservative substitution may reside in the framework regions, or in antigen-binding sites, as long they do not adversely affect the properties of the antibody. Substitutions may be made to improve antibody properties, for example stability or affinity. Conservative substitutions will produce molecules having functional and chemical characteristics similar to those molecules into which such modifications are made. Exemplary amino acid substitutions are shown in the table below.

TABLE

Exemplary Conservative Substitutions:

| Original Residue | Exemplary Conservative Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

In some embodiments, variants of the proteins and peptides provided herein are provided. In some embodiments, a variant comprises a substitution, deletions, or insertion. In some embodiments, the variant comprises 1, 2, 3, 4, 5, 6, 7, 8, 9, or 10 (e.g., 1-10) substitutions. As described herein, the substitutions can be conservative substitutions. In some embodiments, the substitution is non-conservative. In some embodiments, the variant comprises 1, 2, 3, 4, 5, 6, 7, 8, 9, or 10 (e.g., 1-10) deletions. In some embodiments, the variant comprises 1, 2, 3, 4, 5, 6, 7, 8, 9, or 10 (e.g., 1-10) insertions. In some embodiments, the substitutions, deletions, or insertions are present in the CDRs provided for herein. In some embodiments, the substitutions, deletions, or insertions are not present in the CDRs provided for herein.

The term "in combination with" as used herein means that the described agents can be administered to an animal or subject together in a mixture, concurrently as single agents or sequentially as single agents in any order.

The techniques to raise antibodies to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art. Antibodies can also be produced in human, a mouse, sheep, a rat, a rabbit, a shark, a llama, or a chicken. In some embodiments, the antibody is produced in a chicken. The antibodies can also be produced in or other small animals.

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three dimensional structural characteristics as well as specific charge characteristics. Example of epitopes include, but are not limited to, the residues described herein that form IGF-1R epitopes. In some embodiments, the epitope is only present in a non-denatured protein. In some embodiments, the epitope is only present in a denatured protein.

In some embodiments, the source for the DNA encoding a non-human antibody include cell lines which produce antibody, such as hybrid cell lines commonly known as hybridomas.

The hybrid cells are formed by the fusion of a non-human antibody-producing cell, typically a spleen cell of an animal immunized against either natural or recombinant antigen, or a peptide fragment of the antigen protein sequence. Alternatively, the non-human antibody-producing cell can be a B lymphocyte obtained from the blood, spleen, lymph nodes or other tissue of an animal immunized with the antigen.

The second fusion partner, which provides the immortalizing function, can be a lymphoblastoid cell or a plasmacytoma or myeloma cell, which is not itself an antibody producing cell, but is malignant. Fusion partner cells include, but are not limited to, the hybridoma SP2/0-Ag14, abbreviated as SP2/0 (ATCC CRL1581) and the myeloma P3X63Ag8 (ATCC TIB9), or its derivatives. Sec, e.g, Ausubel infra, Harlow infra, and Colligan infra, the contents of which references are incorporated entirely herein by reference.

The antibodies can be generated according the examples provided herein. Once the sequences are known, the antibodies can also be generated according to known methods. The antibodies can also be converted to different types, such as being converted to Human IgGs and the like. By converting the antibodies to a human antibody, a human subject should not identify the antibodies as foreign. The conversion of a non-human IgG antibody to a human IgG antibody is well known and can routinely be done once the native sequence is known. As discussed herein, the antibodies can be modified according to known methods. Such methods are described in, for example, Riechmann L, Clark M, Waldmann H, Winter G (1988). Reshaping human antibodies for therapy". Nature 332 (6162): 332-323; Tsurushita N, Park M, Pakabunto K, Ong K, Avdalovic A, Fu H, Jia A, Vásquez M, Kumar S. (2004). The antibody-producing cell contributing the nucleotide sequences encoding the antigen-binding region of the chimeric antibody can also be produced by transformation of a non-human, such as a primate, or a human cell. For example, a B lymphocyte which produces the antibody can be infected and transformed with a virus such as Epstein-Barr virus to yield an immortal antibody producing cell (Kozbor et al., Immunol. Today 4:72 79 (1983)). Alternatively, the B lymphocyte can be transformed by providing a transforming gene or transforming gene product, as is well-known in the art. Sec, e.g, Ausubel infra, Harlow infra, and Colligan infra, the contents of which references are incorporated entirely herein by reference. The cell fusions are accomplished by standard procedures well known to those skilled in the field of immunology. Fusion partner cell lines and methods for fusing and selecting hybridomas and screening for mAbs are well known in the art. Sec, e.g, Ausubel infra, Harlow infra, and Colligan infra, the contents of which references are incorporated entirely herein by reference.

In some embodiments, the antibody is a MAb which binds to IGF-1R. In some embodiments, the antibody binds to amino acids of an epitope of the IGF-1R.

In some embodiments, the antibody comprises a sequence as provided for herein.

The sequences of the antibodies can be modified to yield human IgG antibodies. The conversion of the sequences provided herein can be modified to yield other types of antibodies. The CDRs can also be linked to other antibodies, proteins, or molecules to create antibody fragments that bind to IGF-1R. This can be in the form of an antibody drug conjugate ("ADC"), a multi-specific molecule, or a chimeric antigen receptor. The CDRs and antibody sequences provided herein also be humanized or made fully human according to known methods. The sequences can also be made into chimeric antibodies as described herein.

In some embodiments, the antibody comprises an amino acid sequence comprising a sequence provided for herein or a fragment thereof. In some embodiments, the antibody comprises one or more amino acid sequences as provided herein, an antigen binding fragments, thereof, or a human IgG variant thereof. "A human IgG variant thereof" refers to an antibody that has been modified to be a human IgG when the starting antibody is not a human IgG antibody.

As described herein the production of antibodies with a known sequence is routine and can be done by any method. Accordingly, in some embodiments, a nucleic acid encoding an antibody or fragment thereof is provided. In some embodiments, the nucleic acid encodes a sequence provided for herein. The antibodies can also be modified to be chimeric antibodies or human antibodies. The antibodies can also be used in injectable pharmaceutical compositions. As also described herein, the antibodies can be isolated antibodies or engineered antibodies.

In some embodiments, "derivatives" of the antibodies, fragments, regions or derivatives thereof, which term includes those proteins encoded by truncated or modified genes to yield molecular species functionally resembling the immunoglobulin fragments are provided.

The modifications include, but are not limited to, addition of genetic sequences coding for cytotoxic proteins such as plant and bacterial toxins. The modification can also include a reporter protein, such as a fluorescent or chemiluminescent tag. The fragments and derivatives can be produced in any manner.

The identification of these antigen binding region and/or epitopes recognized by Abs described herein provide the information necessary to generate additional monoclonal antibodies with similar binding characteristics and therapeutic or diagnostic utility that parallel the embodiments of this application.

The nucleic acid sequence encoding an antibody described herein can be genomic DNA or cDNA, or RNA (e.g. mRNA) which encodes at least one of the variable regions described herein. A convenient alternative to the use of chromosomal gene fragments as the source of DNA encoding the V region antigen-binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a V region antigen-binding segment able to detect, bind, to or neutralize a IGF-1R antigen can be provided using known methods based on the use of the amino acid sequences provided herein. Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an antibody or fragment. Such "codon usage rules" are disclosed by Lathe, et al., J. Molec. Biol. 183:1 12 (1985). Using the "codon usage rules" of Lathe, a single oligonucleotide, or a set of oligonucleotides, that contains a theoretical "most probable" nucleotide sequence capable of encoding an antibody variable or constant region sequences is identified.

The variable regions described herein can be combined with any type of constant region including a human constant region or murine constant region. Human genes which encode the constant (C) regions of the antibodies, fragments and regions can be derived from a human fetal liver library, by known methods. Human C regions genes can be derived from any human cell including those which express and produce human immunoglobulins. The human CH region can be derived from any of the known classes or isotypes of human H chains, including gamma, u, «, 8 or E, and subtypes thereof, such as G1, G2, G3 and G4. Since the H chain isotype is responsible for the various effector functions of an antibody, the choice of CH region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or μ (IgM). The human $C_L$ region can be derived from either human L chain isotype, kappa or lambda. In some embodiments, the antibody comprises a Fc domain. In some embodiments, the Fc domain comprises a mutation to extend the half-life of the antibody. In some embodiments, the Fc domain comprises a mutation such as those described in U.S. Pat. No. 7,670,600, which is hereby incorporated by reference in its entirety. In some embodiment, the constant region comprises a mutation at position at amino acid residue 428 relative to a wild-type human IgG constant domain, numbered according to the EU numbering index of Kabat. Without being bound to any particular theory, an antibody comprising a mutation that corresponds to residue 428 can have an increased half-life compared to the half-life of an IgG having the wild-type human IgG constant domain. In some embodiments, the mutation is a substitution of the native residue with a threonine, leucine, phenylalanine or serine. In some embodiments, the antibody further comprises one or more amino acid substitutions relative to the corresponding wild-type human IgG constant domain at one or more of amino acid residues 251-256, 285-290, 308-314, 385-389, and 429-436, numbered according to the Kabat EU numbering index. The specific mutations or substitutions at these positions are described in U.S. Pat. No. 7,670,600, which is hereby incorporated by reference in its entirety.

Genes encoding human immunoglobulin C regions can be obtained from human cells by standard cloning techniques (Sambrook, et al. (Molecular Cloning: A Laboratory Manual, 2nd Edition, Cold Spring Harbor Press, Cold Spring Harbor, N.Y. (1989) and Ausubel et al., eds. Current Protocols in Molecular Biology (1987 1993)). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the CHI domain and hinge region of the H chain, followed by a translational stop codon to yield the truncated molecule.

In some embodiments, the antibodies, murine, human, humanized, or chimeric antibodies, fragments and regions of the antibodies described herein are produced by cloning DNA segments encoding the H and L chain antigen-binding regions of a IGF-1R antigen specific antibody, and joining these DNA segments to DNA segments encoding $C_H$ and $C_L$ regions, respectively, to produce murine, human or chimeric immunoglobulin-encoding genes.

Thus, in some embodiments, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions, the method of producing the antibody according to some of the embodiments described herein involve several steps, as exemplified below: 1. isolation of messenger RNA (mRNA) from the cell line producing an anti-IGF-1R antigen antibody and from optional additional antibodies supplying heavy and light constant regions; cloning and cDNA production therefrom; 2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody; 3. Construction of complete H or L chain coding sequences by linkage of the cloned specific V region gene segments to cloned C region gene, as described above; 4. Expression and production of L and H chains in selected hosts, including prokaryotic and eukaryotic cells to provide murine-murine, human-murine, human-human or human murine antibodies.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

As used herein and unless otherwise indicated, the term "about" is intended to mean±5% of the value it modifies. Thus, about 100 means 95 to 105.

In some embodiments, the antibodies described herein are used to detect the presence of the antigen. The present antibody can be used in any device or method to detect the presence of the antigen.

The term "purified" with referenced to an antibody refers to an antibody that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure. In some embodiments, the antibody is purified.

As an alternative to preparing monoclonal antibody-secreting hybridomas, a monoclonal antibody to a polypeptide may be identified and isolated by screening a recombinant combinatorial immunoglobulin library (e.g., an antibody phage display library) with a polypeptide described herein to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature. Thus, the epitopes described herein can be used to screen for other antibodies that can be used therapeutically, diagnostically, or as research tools.

Antibody Conjugates

The antibodies provided for herein may also be conjugated to a chemical moiety. The chemical moiety may be, inter alia, a polymer, a radionuclide or a cytotoxic factor. In some embodiments, this can be referred to as an antibody drug conjugate. In some embodiments, the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)). Examples of chemical moieties include, but are not limited to, anti-mitotics, such as calicheamicins (e.g. ozogamicin), monomethyl auristatin E, mertansine, and the like. Other examples include, but are not limited to, biologically active anti-microtubule agents, alkylating agents and DNA minor groove binding agents. Other examples of are provided herein and below. The chemical moiety can be linked to the antibody through a linking group (maleimide), a cleavable linker, such as a cathepsin cleavable linkers (valine-citrulline), and in some embodiments, one or more spacers (e.g. para-aminobenzyl-carbamate). Without being bound to any particular theory, once the antibody conjugate binds IGF-1R it can be internalized and the chemical moiety can kill the cell or otherwise inhibit its growth. In some embodiments, the cell is a thyroid cell.

The antibodies and antibody fragments of the invention may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fc, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

The antibodies and antibody fragments may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, 152Eu, dansyl, umbelliferone, luciferin, luminal label, isoluminal label, an aromatic acridinium ester label, an imidazole label, an acridimium salt label, an oxalate ester label, an acquorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

Chimeric Antigen Receptors

The antibodies provided herein can also be incorporated into a chimeric antigen receptor ("CAR") that can be used, for example, in a CAR-T cell. In some embodiments, the extracellular domain of the CAR can be an antibody as provided for herein. In some embodiments, the antibody is in a scFv format. CAR-T cells are a type of treatment in which a patient's T cells are modified so they will attack the cells that are expressing IGF-1R. T cells are taken from a patient's blood. Then the gene for a special receptor that binds to a certain protein on the patient's cells is added in the laboratory. In some embodiments, the receptor binds to IGF-1R using the binding regions of the antibodies provided for herein. The CAR-T cells comprising the IGF-1R antibody can then be used to treat a condition, such as those provided for herein.

In some embodiments, antibodies (e.g. an anti-IGF-1R antibody) are provided herein. In some embodiments, the antibody is a recombinant antibody that binds to a IGF-1R protein. In some embodiments, the IGF-1R protein is a human IGF-1R protein. In some embodiments, the IGF-1R protein that is recognized by the antibodies is in its native conformation (non-denatured) conformation. In some embodiments, the antibody does not specifically bind to a denatured IGF-1R protein. As used herein, the term "recombinant antibody" refers to an antibody that is not naturally occurring. In some embodiments, the term "recombinant antibody" refers to an antibody that is not isolated from a human subject.

In some embodiments, the antibody comprises one or more peptides having the following sequences, or a variant thereof:

| AB ID NO. | AB Sequence | VL Sequence | VH Sequence |
|---|---|---|---|
| VRDN-5000 | DVVMTQTPLS LPVSLGDPAS ISCRSSQSIV HSNVNTYLEW YLQKPGQSPR LLIYKVSNRF SGVPDRFSGS GAGTDFTLRI SRVEAEDLGI | DVVMTQTPLS LPVSLGDPAS ISCRSSQSIV HSNVNTYLEW YLQKPGQSPR LLIYKVSNRF SGVPDRFSGS GAGTDFTLRI SRVEAEDLGI | QVQLVQSGAE VVKPGASVKL SCKASGYTFT SYWMHWVKQR PGQGLEWIGE INPSNGRTNY NQKFQGKATL TVDKSSSTAY MQLSSLTSED |
| | YYCFQGSHVP PTFGGGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC (SEQ ID NO: 11) | YYCFQGSHVP PTFGGGTKLE IKR (SEQ ID NO: 2) | SAVYYFARGR PDYYGSSKWY FDVWGQGTTV TVSS (SEQ ID NO: 3) |
| | QVQLVQSGAE VVKPGASVKL SCKASGYTFT SYWMHWVKQR PGQGLEWIGE INPSNGRTNY NQKFQGKATL TVDKSSSTAY MQLSSLTSED SAVYYFARGR PDYYGSSKWY FDVWGQGTTV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK KVEPKSCDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK (SEQ ID NO: 10) | | |

The VH and the VL sequences can be in any format, including, but not limited to a scFv format where the VH and VL regions are linked with a peptide linker. Examples of peptide linkers that can be used to link various peptides provided for herein include, but are not limited to: (GGGGS)$_n$ (SEQ ID NO: 12); (GGGGA)$_n$ (SEQ ID NO: 13), or any combination thereof, wherein each n is independently 1-5. In some embodiments, the variable regions are not linked with a peptide linker. In some embodiments, the antibody comprises or consists of a polypeptide set forth in SEQ ID NOS: 10 and 11. In some embodiments, the antibody comprises a polypeptide comprising SEQ ID NOS: 3, 4, 5, 6, 7, 8, and 9.

In some embodiments, an antibody, or antigen binding fragment thereof is provided, wherein the antibody or antibody fragment comprises a peptide selected from the following table.

| Ab ID No | LCDR1 | LCDR2 | LCDR3 | HCDR1 | HCDR2 | HCDR3 |
|---|---|---|---|---|---|---|
| VRDN-5000 | RSSQSI VHSNVN TYLE (SEQ ID NO: 4) | KVSNRFS (SEQ ID NO: 5) | FQGSH VPPT (SEQ ID NO: 6) | SYWMH (SEQ ID NO: 7) | GEIN PSNG RTNY NQK FQG (SEQ ID NO: 8) | GRPD YYGS SKWY FDV (SEQ ID NO: 9) |

In some embodiments, the antibody comprises one or more peptides having the following sequences, or a variant thereof comprising one or more variable domain (italicized) CDRs (italics and bold) and a human IgG1/Kappa constant domain (underlined):

| | |
|---|---|
| VRDN-5000_HC (SEQ ID NO: 10) | QVQLVQSGAEVVKPGASVKLSCKASGYTFT SYWMH WVKQRPGQGLEWIG EINPSNGRT NYNQKFQG KATLTVDKSSSTAYMQLSSLTSEDSAV YYFAR GRPDYYGSSKWYFDVWGQGTTVTVSS ASTKGPSVFPLAPSSKSTSGGTAALG CLVKDYFPEPVTVSWNSGALTSGVHTFPAV LQSSGLYSLSSVVTVPSSSLGTQTYICNVN HKPSNTKVDKKVEPKSCDKTHTCPPCPAPE LLGGPSVFLFPPKPKDTLMISRTPEVTCVV VDVSHEDPEVKFNWYVDGVEVHNAKTKPRE EQYNSTYRVVSVLTVLHQDWLNGKEYKCKV SNKALPAPIEKTISKAKGQPREPQVYTLPP SRDELTKNQVSLTCLVKGFYPSDIAVEWES NGQPENNYKTTPPVLDSDGSFFLYSKLTVD KSRWQQGNVFSCSVMHEALHNHYTQKSLSL SPGK |
| VRDN-5000_LC (SEQ ID NO: 11) | DVVMTQTPLSLPVSLGDPASISC RSSQSIVHSNVNTYLEWYLQKPG QSPRLLIKVSNRFSGVPDRFSG SGAGTDFTLRISRVEAEDLGIYYC FQGSHVPPTFGGGTKLEIKRTVAAPSV FIFPPSDEQLKSGTASVVCLLNNFYPREAK VQWKVDNALQSGNSQESVTEQDSKDSTYSL SSTLTLSKADYEKHKVYACEVTHQGLSSPV TKSFNRGEC |

In some embodiments, an antibody, or antibody binding fragment thereof, comprises a heavy or light chain having a sequence of SEQ ID NOs: 10 and 11. In some embodiments, an antibody, or an antibody binding fragment thereof, comprises a heavy chain having a sequence of SEQ ID NO: 10. In some embodiments, an antibody, or an antibody binding fragment thereof, comprises a heavy chain having a sequence that is 95%, 96%, 97%, 98%, 99%, 99.5%, 99.9% or substantially 100% identical to that of SEQ ID NO: 10. In some embodiments, the sequence that is 95%, 96%, 97%, 98%, 99%, 99.5%, 99.9% or substantially 100% identical to that of SEQ ID NO: 10 comprises the CDRs of SEQ ID NO: 7, 8, and/or 9 as set forth above.

In some embodiments, an antibody, or an antibody binding fragment thereof, comprises a light chain having a sequence of SEQ ID NO: 11. In some embodiments, an antibody, or antibody binding fragment thereof, comprises a light chain having a sequence that is 95%, 96%, 97%, 98%, 99%, 99.5%, 99.9% or substantially 100% identical to that of SEQ ID NO: 11 In some embodiments, the sequence that is 95%, 96%, 97%, 98%, 99%, 99.5%, 99.9% or substantially 100% identical to that of SEQ ID NO: 11 comprises the CDRs of SEQ ID NO: 4, 5, and/or 6 as set forth above.

In some embodiments, an antibody, or antibody binding fragment thereof, comprises a light chain CDR having a sequence of SEQ ID NO: 4, 5, or 6. In some embodiments, an antibody, or antibody binding fragment thereof comprises a heavy chain CDR having a sequence of SEQ ID NO: 7, 8, or 9.

In some embodiments, an antibody, or antibody binding fragment thereof, comprises a light chain having a LCDR1, a LCDR2, and a LCDR3, wherein the LCDR1 has a sequence of SEQ ID NO: 4 the LCDR2 has a sequence of SEQ ID NO: 5 and the LCDR3 has a sequence of SEQ ID NO: 6.

In some embodiments, an antibody, or antibody binding fragment thereof, comprises a heavy chain having a HCDR1, a HCDR2, and a HCDR3, wherein the HCDR1 has a sequence of SEQ ID NO: 7 the HCDR2 has a sequence of SEQ ID NO: 8 and the HCDR3 has a sequence of SEQ ID NO: 9.

The different CDR motifs can be combined in any combination including those not depicted in the table above. For example, the following embodiments are provided as non-limiting examples of such combinations.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 4; the light chain CDR2 has the amino acid sequence of SEQ ID NO: 5; and the light chain CDR3 sequence has the amino acid sequence of SEQ ID NO: 6; and (ii) a heavy chain variable region comprising heavy chain CDR1, CDR2, and CDR3 sequences, wherein the heavy chain CDR1 sequence has the amino acid sequence of SEQ ID NO: 7; the heavy chain CDR2 sequence has the amino acid sequence of SEQ ID NO: 8; and the heavy chain CDR3 sequence has the amino acid sequence of SEQ ID NO: 9; or variants of any of the foregoing.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence that is 95%, 96%, 97%, 98%, 99%, 99.5%, 99.9% or substantially 100% identical to that of SEQ ID NO: 4; the light chain CDR2 has the amino acid sequence that is 95%, 96%, 97%, 98%, 99%, 99.5%, 99.9% or substantially 100% identical to that of SEQ ID NO: 5; and the light chain CDR3 sequence has the amino acid sequence that is 95%, 96%, 97%, 98%, 99%, 99.5%, 99.9% or substantially 100% identical to that of SEQ ID NO: 6; and (ii) a heavy chain variable region comprising heavy chain CDR1, CDR2, and CDR3 sequences, wherein the heavy chain CDR1 sequence has the amino acid sequence that is 95%, 96%, 97%, 98%, 99%, 99.5%, 99.9% or substantially 100% identical to that of SEQ ID NO: 7; the heavy chain CDR2 sequence has the amino acid sequence that is 95%, 96%, 97%, 98%, 99%, 99.5%, 99.9% or substantially 100% identical to that of SEQ ID NO: 8; and the heavy chain CDR3 sequence has the amino acid sequence that is 95%, 96%, 97%, 98%, 99%, 99.5%, 99.9% or substantially 100% identical to that of SEQ ID NO: 9; or variants of any of the foregoing.

In some embodiments, the antibody, or antigen binding fragment thereof, or protein is provided that comprises a peptide having a sequence as set forth in any of SEQ ID NOs: 1, 2, 3, 4, 5, 6, 7, 8, 9, 10, or 11.

In some embodiments, the antibody, or antigen binding fragment thereof, comprises a sequence of, or a variant of any of the foregoing.

Pharmaceutical Compositions

In some embodiments, to prepare pharmaceutical or sterile compositions of the anti-IGF-1R antibodies or other proteins provided herein, the antibody or antigen binding fragment thereof or other proteins provided herein are admixed with a pharmaceutically acceptable carrier or excipient. See, e.g., *Remington's Pharmaceutical Sciences and U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY). In some embodiments, the antibodies are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In some embodiments, a composition of the invention is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In some embodiments, the antibody or antigen binding fragment thereof can be administered by an invasive route such as by injection. In some embodiments, the antibodies or antigen binding fragment thereof, or pharmaceutical composition thereof, is administered intravenously, subcutaneously, intramuscularly, intraarterially, intra-articularly (e.g. in arthritis joints), or by inhalation, aerosol delivery. Administration by non-invasive routes (e.g., orally; for example, in a pill, capsule or tablet) is also within the scope of the present embodiments.

In some embodiments, the anti-IGF-1R antibody, or antigen binding fragment thereof, is administered in combination with at least one additional therapeutic agent, such as, but not limited to any therapeutic used to treat thyroid eye disease. For example, in some embodiments, the anti-IGF-1R antibody, or antigen binding fragment thereof, is administered in combination with at least one additional therapeutic agent, such as, but not limited to a therapeutic used to treat thyroid eye disease or a condition related to the same. Examples of such treatments and therapeutics include, but are not limited to anti-thyroid medications, diabetes medications, beta-blockers, propylthiouracil, methimazole, propranolol, atenolol, metoprolol, nadolol, corticosteroids, metformin, sulfonylureas, meglitinides, thiazolidinediones, DPP-4 inhibitors, GLP-1 receptor agonists, SGLT2 inhibitors, regular insulin, insulin aspart, insulin glulisine, insulin lispro, insulin isophane, insulin degludec, insulin detemir, insulin glargine, acerbose, miglitol, acebutolol, atenolol, betaxolol, bisoprolol, cartelol, carvedilol, esmolol, labetalol, metoprolol, nadolol, nebivolol, penbutolol, pindolol, propranolol, sotalol, timolol, tomolol ophthalmic solution, sitagliptin, saxagliptin, linagliptin, alogliptin, dulaglutide, exenatide, semaglutide, liraglutide, lixisenatide, canagliflozin, dapagliflozin, empagliflozin, or any combination thereof.

Compositions can be administered with medical devices known in the art. For example, a pharmaceutical composition of the invention can be administered by injection with a hypodermic needle, including, e.g., a prefilled syringe or autoinjector.

The pharmaceutical compositions may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) New Engl. J. Med. 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable.

Antibodies or antigen binding fragments thereof can be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) New Engl. J. Med. 349:427-434; Herold, et al. (2002) New Engl. J. Med. 346:1692-1698; Liu, et al. (1999) J. Neurol. Neurosurg. Psych. 67:451-456; Portielji, et al. (20003) Cancer Immunol. Immunother. 52:133-144). Doses may also be provided to achieve a pre-determined target concentration of the antibody in the subject's serum, such as 0.1, 0.3, 1, 3, 10, 30, 100, 300 µg/ml or more. In other embodiments, a fully human antibody is administered subcutaneously or intravenously, on a weekly, biweekly, "every 4 weeks," monthly, bimonthly, or quarterly basis at 10, 20, 50, 80, 100, 200, 500, 1000 or 2500 mg/subject or as otherewise provided for herein.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the antibody, or antigen binding fragment thereof, that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. In some embodiments, an amount is a therapeutically effective amount if it is an amount that can be used to treat or ameliorate a condition as provided for herein.

The term "subject" as used throughout includes any organism, such as an animal, including a mammal (e.g., rat, mouse, dog, cat, rabbit) and, for example, a human. A subject can be also be referred to as a patient. In some embodiments, the subject is a subject in need thereof. A subject that is "in need thereof" refers to a subject that has been identified as requiring treatment for the condition that is to be treated and is treated with the specific intent of treating such condition. The conditions can be, for example, any of the conditions described herein.

Whereas, an isolated antibody binds an epitope on a IGF-1R protein, or other protein described herein, and displays in vitro and/or in vivo IGF-1R inhibiting or therapeutic activities, the antibodies or antigen binding fragments thereof, capable of inhibiting IGF-1R function, are suitable both as therapeutic agents for treating IGF-1R-associated conditions in humans and animals. These conditions include thyroid eye disease. Accordingly, methods of treating such conditions are also provided, wherein the method comprises administering an antibody, or antigen binding fragment thereof, to the subject with such a condition.

In some embodiments, the methods comprise administering a therapeutically or prophylactically effective amount of one or more monoclonal antibodies or antigen binding fragments of the antibodies described herein to a susceptible subject or to one exhibiting a condition in which IGF-1R is known or suspected to have caused the pathology observed. Any active form of the antibody can be administered, including, but not limited to scFV, Fab and F(ab')2 fragments and other forms of antibodies provided for herein.

As used herein, a IGF-1R associated pathology refers to conditions that are caused by the modulation of IGF-1R. These conditions include, but are not limited to, thyroid eye disease and other conditions provided for herein.

In some embodiments, the antibodies used are compatible with the recipient species such that the immune response to the MAbs does not result in an unacceptably short circulating half-life or induce an immune response to the MAbs in the subject.

Treatment of individuals may comprise the administration of a therapeutically effective amount of the antibodies described herein. The antibodies can be provided in a kit, such as those provided herein. The antibodies can be used or administered alone or in admixture with another therapeutic, analgesic, or diagnostic agent, such as provided for herein. In providing a patient with an antibody, or fragment thereof, capable of binding to IGF-1R, or an antibody capable of protecting against IGF-1R, pathology in a recipient patient, the dosage of administered agent will vary depending upon such factors as the patient's age, weight, height, sex, general medical condition, previous medical history, etc.

An antibody, capable treating a condition associated with IGF-1R activity or use to treat a IGF-1R related pathology, is intended to be provided to subjects in an amount sufficient to affect a reduction, resolution, or amelioration in the IGF-1R related symptom or pathology. Such a pathology includes thyroid eye disease and the like.

Accordingly, in some embodiments, methods of treating a subject with a IGF-1R mediated disorder are provided. In some embodiments, the method comprises administering a pharmaceutical composition comprising an antibody, or antigen binding fragment thereof, as provided herein. In some embodiments, the disorder is thyroid eye disease. As provided for herein, the antibodies, or antigen binding fragments thereof, can be administered with other therapeutics. These can be administered simultaneously or sequentially.

In some embodiments, the antibodies, or antigen binding fragments thereof, may be used to treat thyroid eye disease. In some embodiments, the antibodies, or antigen binding fragments thereof, may be used to treating or reduce the severity of, thyroid-associated ophthalmopathy (TAO), or a symptom thereof.

In some embodiments, methods or uses are provided to reduce proptosis in an eye in a subject with thyroid-associated ophthalmopathy (TAO).

In some embodiments, the subject is a subject how has previously been treated with a different antibody than those provided herein.

In some embodiments, methods or uses are provided to Clinical Activity Score (CAS) in subject who has or is suspected of having thyroid-associated ophthalmopathy (TAO).

In some embodiments, methods or uses are provided to reduce proptosis by at least 2 mm. In some embodiments, methods or uses are provided to reduce proptosis by at least 3 mm. In some embodiments, methods or uses are provided to reduce proptosis by at least 2-3 mm or 2-4 mm. In some embodiments, the proptosis is reduced by at least 2, 3, or 4 mm. In some embodiments, the reduction in proptosis is seen within 3 weeks of the first dose administration. In some embodiments, the reduction in proptosis is seen within 6 weeks of the first dose administration.

In some embodiments, the subject has a reduced the clinical activity score (CAS) in a subject with thyroid-associated ophthalmopathy (TAO).

As used herein, the term Clinical Activity Score (CAS) refers to the protocol described and scored according to Table 2. According to this protocol, one point is given for the presence of each of the parameters assessed in the Table below. The sum of all points defines clinical activity and provides the CAS, where 0 or 1 constitutes inactive disease and 7 severe active ophthalmopathy.

TABLE 2

Parameters for calculating Clinical Activity Score

| Item No. | Parameter |
| --- | --- |
| 1 | Spontaneous retrobulbar pain |
| 2 | Pain on attempted eye movements (upward, side to side, and downward gazes; sometimes termed gaze evoked orbital pain |
| 3 | Eyelid swelling |
| 4 | Eyelid erythema (redness) |
| 5 | Conjunctival redness |
| 6 | Chemosis (swelling/edema of the conjunctiva) |
| 7 | Swelling of caruncle or pila |

As provided in Table 2, the CAS consists of seven components: spontaneous retrobulbar pain, pain on attempted eye movements (upward, side-to-side, and downward gazes), conjunctival redness, redness of the eyelids, chemosis, swelling of the caruncle/plica, and swelling of the eyelids. Each component is scored as present (1 point) or absent (0 points). The score at each efficacy assessment is the sum of all items present; giving a range of 0-7, where 0 or 1 constitutes inactive disease and 7 severe active ophthalmopathy. A change of >2 points is considered clinically meaningful. In some embodiments, the subject's score improves by at least 2, 3, or 4 points. In some embodiments, the subject's score improves within 3 weeks of the first dose. In some embodiments, the subject's score improves within 6 weeks of the first dose.

Item 1, spontaneous orbital pain could be a painful, or oppressive feeling on, or behind, the globe. This pain may be caused by the rise in intraorbital pressure, when the orbital tissues volume increases through excess synthesis of extracellular matrix, fluid accumulation, and cellular infiltration and expansion. Item 2, gaze evoked orbital pain, could be pain in the eyes when looking, or attempting to look, up, down or sideways, i.e., pain with upward, downward, or lateral eye movement, or when attempting eye movement. This kind of pain could arise from the stretching of the inflamed muscle(s), especially on attempted upgaze. The 'stretching pain' cannot be provoked by digital pressing on the eyeball, as would be expected if it were a manifestation of the raised intraorbital pressure. Both kinds of pain can be reduced after anti-inflammatory treatment. These kinds of pain are therefore considered to be directly related to autoimmune inflammation in the orbit and thus useful in assessing TAO activity.

Swelling in TAO is seen as chemosis (edema of the conjunctiva), item no. 6 in Table 1, and swelling of the caruncle and/or *Plica semilunaris*. Both are signs of TAO activity. Swollen eyelids can be caused by edema, fat prolapse through the orbital septum, or fibrotic degeneration. In addition to swelling, other symptoms indicative of active TAO include redness and/or pain of the conjunctiva, eyelid, caruncle and/or *Plica semilunaris*.

In some embodiments, the subject who is treated has the proptosis is reduced by at least 2 mm. In some embodiments, the subject who is treated has the proptosis is reduced by at least 3 mm. In some embodiments, the subject who is treated has the proptosis is reduced by at least 4 mm.

In some embodiments, in the subjects who are treated the clinical activity score (CAS) of the subject is reduced by at least 2 points. In some embodiments, the clinical activity score (CAS) of the subject is reduced to one (1). In some embodiments, the clinical activity score (CAS) of the subject is reduced to zero (0).

In some embodiments, methods off treating or reducing the severity of thyroid-associated ophthalmopathy (TAO) in a subject are provided, wherein the treatment with said antibody (i) reduces proptosis by at least 2 mm in an eye; (ii) is not accompanied by a deterioration of 2 mm or more in the other (or fellow eye); and (iii) reduces the CAS in said subject to either one (1) or zero (0).

In some embodiments, methods of improving the quality of life in a subject with thyroid-associated ophthalmopathy (TAO, also called Graves' Ophthalmopathy/Graves' Orbitopathy) are provided. In some embodiments, the quality of life is measured by the Graves' Ophthalmopathy Quality of Life (GO-QoL) assessment, or either the Visual Functioning or Appearance subscale thereof. In some embodiments, the treatment results in an improvement of greater than or equal to 8 points on the GO-QoL. In some embodiments, the treatment results in an improvement on the Functioning subscale of the GO-QoL. In some embodiments, the treatment results in an improvement on the Appearance subscale of the GO-QoL.

In some embodiments, methods of treating or reducing the severity of diplopia in a subject with thyroid-associated ophthalmopathy (TAO) are provided. In some embodiments, the diplopia is constant diplopia. In some embodiments, the diplopia is inconstant diplopia. In some embodiments, the diplopia is intermittent diplopia. In some embodiments, the improvement in or reduction in severity of diplopia is sustained at least 20 weeks after discontinuation of antibody administration. In some embodiments, the improvement in or reduction in severity of diplopia is sustained at least 50 weeks after discontinuation of antibody administration. In some embodiments, the diplopia is improved in the subject within 3 weeks or within 6 weeks of the first dose.

The severity of the disease can be measured in the following non-limiting embodiments. For example, for lid aperture, the distance between the lid margins are measured (in mm) with the patient looking in the primary position, sitting relaxed, and with distant fixation. For swelling of the eyelids, the measure/evaluation is either "absent/equivocal," "moderate," or "severe." Redness of the eyelids is either absent or present. Redness of the conjunctivae is either absent or present. In some embodiments, conjunctival edema is either absent or present. In some embodiments, inflammation of the caruncle or plica is either absent or present. Exophthalmos is measured in millimeter using the same Hertel exophthalmometer and same intercanthal distance for an individual patient. Subjective diplopia is scored from 0 to 3 (0=no diplopia; 1=intermittent, i.e., diplopia in primary position of gaze, when tired or when first awakening; 2=inconstant, i.e., diplopia at extremes of gaze; 3=constant, i.e., continuous diplopia in primary or reading position). For eye muscle involvement, the ductions are measured in degrees. Corneal involvement is either absent/ punctate or keratopathy/ulcer. For optic nerve involvement, i.e., best-corrected visual acuity, color vision, optic disc, relative afferent pupillary defect, the condition is either absent or present. In addition, visual fields are checked if optic nerve compression is suspected. In some embodiments, the patient can be classified according to the following severity classification. For example, sight-Threatening Thyroid Eye Disease: Patients with dysthyroid optic neuropathy (DON) and/or corneal breakdown. This category warrants immediate intervention. Moderate-to-Severe Thyroid Eye Disease: Patients without sight-threatening disease whose eye disease have sufficient impact on daily life to justify the risks of immunosuppression (if active) or surgical intervention (if inactive). Patients with moderate-to-severe thyroid eye disease usually have any one or more of the following: lid retraction greater than or equal to 2 mm, moderate or severe soft tissue involvement, exophthalmos greater than or equal to 3 mm above normal for race and gender, inconstant or constant diplopia. Mild Thyroid Eye Disease: Patients whose features of thyroid eye disease have only a minor impact on daily life insufficient to justify immunosuppressive or surgical treatment. They usually have only one or more of the following: minor lid retraction (<2 mm), mild soft tissue involvement, exophthalmos <3 mm above normal for race and gender, transient or no diplopia, and corneal exposure responsive to lubricants.

In some embodiments, a patient can be characterized by Graves Ophthalmopathy Quality of Life (GO-QoL) score. In addition to proptosis (or exophthalmos) and CAS, quality of life is also evaluated with the use of the GO quality of life (GO-QOL) questionnaire. This questionnaire is designed to determine the improved quality of life after treatment with a method disclosed herein. In some embodiments, questionnaire may determine the decreased or lack of side effects after being treated with an antibody, or an antigen binding fragment thereof, according to a method disclosed herein as compared to treatment with glucocorticoids. The GO-QoL is a 16-item self-administered questionnaire divided into 2 subsets and used to assess the perceived effects of TED by the subjects on (i) their daily physical activity as it relates to visual function, and (ii) psychosocial functioning. quality of life is evaluated with the use of the GO QOL questionnaire. The GO-QOL questionnaire [C. B. Terwee et al, 1998] is completed on Day 1 and Weeks 6, 12, and 24 (or PW) during the Treatment Period, and at Months 7 and 12 (or PW) during the Follow-Up Period. The GO-QoL is a 16-item self-administered questionnaire divided into two self-assessment subscales; one covering impact of visual function on daily activities, the other assesses the impact of self-perceived appearance. The visual function subscale covers activities such as driving, walking outdoors, reading, watching television. The appearance subscale asks the subject questions such as whether ophthalmopathy has altered the subject's appearance, caused other people to have a negative reaction to the subject, caused social isolation, and caused the subject to try to mask his or her appearance. Each subscale has 8 questions which are answered with: yes— very much so; yes—a little; or no—not at all. Each question is scored 0-2, respectively, and the total raw score is then mathematically transformed to a 0-100 scale, where 0 represents the most negative impact on quality of life, and 100 represents no impact. A change of > or greater than equal to 8 points on the 0-100 scale has been shown to be clinically meaningful. The combined score takes raw scores from both subscales and again transforms them to a single 0-100 scale. The questionnaire has two self-assessment subscales. Each subscale has 8 questions which are answered with: (i) yes—very much so; (ii) yes—a little; or (iii) no—not at all. Each question is scored 0-2, respectively, and the total raw score is then mathematically transformed to a 0-100 scale, where 0 represents the most negative impact on quality of life, and 100 represents no impact. A change of >8 points on the 0-100 scale is considered to be clinically meaningful. The combined score takes raw scores from both subscales and again transforms them to a single 0-100 scale.

Patients can also be assessed by the presence of absence of Gorman Grading of Diplopia. The Gorman assessment of subjective diplopia includes four categories: no diplopia (absent), diplopia when the patient is tired or awakening (intermittent), diplopia at extremes of gaze (inconstant), and continuous diplopia in the primary or reading position (constant). Patients are scored according to which grade of diplopia they are experiencing. An improvement of greater than equal or to 1 grade is considered clinically meaningful.

In some embodiments, the methods comprise administering an antibody, such as those provided herein. In some embodiments, the antibody is administered at a dosage of about 1 mg/kg to about 5 mg/kg antibody as a first dose. In some embodiments, the antibody is administered at a dosage of about 5 mg/kg to about 10 mg/kg antibody as a first dose. In some embodiments, the antibody is administered at a dosage of about 5 mg/kg to about 20 mg/kg antibody in subsequent doses. In some embodiments, the antibody is administered in the following amounts: about 10 mg/kg antibody as a first dose; and about 20 mg/kg antibody in subsequent doses. In some embodiments, the subsequent doses are administered every three weeks for at least 21 weeks.

In some embodiments, the antibody is administered in a pharmaceutical composition, such as those provided herein. In some embodiments, the pharmaceutical composition further comprises one or more pharmaceutically active compounds for the treatment of TAO. In some embodiments, the pharmaceutical composition further comprises corticosteroids; rituximab or other anti-CD20 antibodies; tocilizumab or other anti-IL-6 antibodies; or selenium, infliximab or other anti-TNFalpha antibodies or a thyroid-stimulating hormone receptor (TSHR) inhibitor.

In some embodiments, the method provided herein comprise administering to a subject an antibody, or an antigen binding fragment thereof, that specifically binds to and inhibits IGF-1R. In some embodiments, the antibody is as provided herein.

Kits are also provided which are useful for carrying out embodiments described herein. The present kits comprise a first container containing or packaged in association with the above-described antibodies. The kit may also comprise another container containing or packaged in association solutions necessary or convenient for carrying out the embodiments. The containers can be made of glass, plastic or foil and can be a vial, bottle, pouch, tube, bag, etc. The kit may also contain written information, such as procedures for carrying out the embodiments or analytical information, such as the amount of reagent contained in the first container means. The container may be in another container apparatus, e.g. a box or a bag, along with the written information.

Yet another aspect provided for herein is a kit for detecting IGF-1R protein in a biological sample. The kit includes a container holding one or more antibodies which binds an epitope of IGF-1R protein and instructions for using the antibody for the purpose of binding to IGF-1R protein to form an immunological complex and detecting the formation of the immunological complex such that the presence or absence of the immunological complex correlates with presence or absence of IGF-1R protein in the sample. Examples of containers include multiwell plates which allow simultaneous detection of IGF-1R protein in multiple samples.

In some embodiments, antibodies that bind to a IGF-1R protein are provided. In some embodiments, the antibody is isolated. In some embodiments, the antibody binds specifically. In some embodiments, the antibody binds to a IGF-1R protein that is properly folded. In some embodiments, the antibody is specific for a specific IGF-1R conformational state (open or closed). In some embodiments, the antibody binds to a IGF-1R protein in a cell membrane. In some embodiments, the antibody binds to a IGF-1R protein that is in a cell membrane in an intact cell. In some embodiments, the antibody inhibits or neutralizes the function of a IGF-1R protein. As used herein, the term "neutralize" means that the activity or function of the protein is inhibited. The inhibition can be complete or partial. In some embodiments, the activity or function of the protein is inhibited at least 10, 20, 30, 40, 50, 60, 70, 80, 90, 95, or 99%. The percent inhibition can be based upon the function or activity of the protein in the absence of the antibody. In some embodiments, the antibody inhibits the glucose transport facilitated by IGF-IR. In some embodiments, the antibody inhibits the internalization of the IGF-1R protein.

In some embodiments, the antibody comprises a sequence as provided for herein or antigen binding fragment thereof. In some embodiments, the antibody comprises a heavy chain CDR or an antigen binding fragment thereof described herein. The heavy chain may be one or more of the heavy chains described herein. In some embodiments, the antibody comprises a light chain, or an antigen binding fragment thereof as described herein In some embodiments, methods of treating, inhibiting or ameliorating a IGF-1R, associated pathology are provided. In some embodiments, the methods comprise administering an antibody described herein or a pharmaceutical composition described herein to a subject to treat, inhibit or ameliorate a IGF-1R associated pathology. In some embodiments, the pathology is as described herein.

In some embodiments, methods of detecting the presence or absence of a IGF-1R in a sample are provided, the method comprising contacting a sample with one or more antibodies described herein detecting the binding to a IGF-1R antigen by the antibody. In some embodiments, the detection of the binding indicates the presence IGF-1R antigen; or the absence of the detection of the binding to the IGF-1R antigen indicates the absence of the IGF-1R antigen. The detecting can be done with any known method, such as using a biosensor, ELISA, sandwich assay, and the like. However, in some embodiments, the method comprises detecting the presence of the protein in non-denaturing conditions. The non-denaturing conditions can be used so that the protein of interest is detected in its native, or properly folded form.

In some embodiments, methods of identifying a test antibody that binds to an epitope on IGF-1R protein, are provided, the method comprising contacting a test antibody with the epitope on IGF-1R protein and determining whether the test antibody binds to the epitope. In some embodiments, the determining comprises determining whether the test antibody binds to the protein and is competitively inhibited by an antibody comprising a sequence as provided herein. In some embodiments, the determining comprises mutating one or more residues of epitope or protein and determining binding of the test antibody to the mutated epitope, wherein if the mutation reduces binding of the test antibody as compared to the non-mutated epitope, the test antibody is deemed to bind to that epitope.

In some embodiments, methods of monitoring internalization of IGF-1R from the surface of a cell are provided. In some embodiments, the method comprising contacting the cell with an anti-IGF-1R antibody as provided herein and detecting the presence of IGF-1R in the cell or on the surface of the cell. The differences in cell surface expression can be measured and the internalization can be monitored and measured. This can be used, for example, to measure the effect of another molecule, such as a test agent, to modulate internalization of IGF-1R protein. Thus, the antibodies provided for herein can be used to identify test agents that modulate (increase or decrease) the internalization of IGF-1R protein. Test molecules that increase the internalization, which would be measured as a decrease in binding of an anti-IGF-1R antibody to IGF-1R protein on the cell surface, can be identified according to the methods provided herein. Test molecules that decrease the internalization, which would be measured as an increase in binding of an anti-IGF-1R antibody to IGF-1R protein on the cell surface, can be identified according to the methods provided herein. The surface expression can be measured by fluorescence, which can be done through a secondary antibody that recognized the IGF-1R antibodies or by labelling the anti-IGF-1R antibodies provided for herein.

In some embodiments, methods of treating thyroid associated ophthalmopathy in a subject in need thereof are provided. In some embodiments, the method comprises intravenously administering a dose of 10 mg/kg of an anti-IGF-1R antibody to the subject at a regular interval for a period sufficient to reduce one or more symptoms associated with thyroid associated ophthalmopathy, wherein the anti-IGF-1R antibody comprises a heavy chain comprising a HCDR1 of SEQ ID NO: 7, a HCDR2 of SEQ ID NO: 8, and a HCDR3 of SEQ ID NO: 9 and a light chain comprising a LCDR1 of SEQ ID NO: 4, a LCDR2 of SEQ ID NO: 5 and a LCDR3 of SEQ ID NO: 6. In some embodiments, the anti-IGF-1R antibody comprises a light chain and a heavy chain, wherein the light chain comprises a variable region having the amino acid sequence of SEQ ID NO: 2 and the heavy chain comprises a variable region having the amino acid sequence of SEQ ID NO: 3. In some embodiments, the light chain comprises an amino acid sequence of SEQ ID NO: 11. In some embodiments, the heavy chain comprises an amino acid sequence of SEQ ID NO: 10. In some embodiments, the heavy chain comprises an amino acid sequence of SEQ ID NO: 10 and the light chain comprises an amino acid sequence of SEQ ID NO: 11. In some embodiments, the anti-IGF-1R antibody is administered by intravenous infusion. In some embodiments, the anti-IGF-1R antibody is administered every 3 weeks. In some embodiments, the anti-IGF-1R antibody is administered for a period sufficient for 5 doses. In some embodiments, the anti-IGF-1R antibody is administered for a period sufficient for 8 doses. In some embodiments, the anti-IGF-1R antibody is administered for a period selected from 3 weeks, 6 weeks, 9 weeks, 12 weeks, 15 weeks, 18 weeks, 21 weeks, 24 weeks or longer.

In some embodiments, an antibody for use in the treatment of thyroid associated ophthalmopathy in a subject in need thereof, is provided. In some embodiments, an anti-IGF-1R antibody for use in the treatment of thyroid associated ophthalmopathy in a subject in need thereof, is provided.

In some embodiments, embodiments provided herein also include, but are not limited to:

1. A method of treating thyroid associated ophthalmopathy in a subject in need thereof, comprising:
   intravenously or subcutaneously administering a first dose, wherein the first dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg, of an antibody to the subject, and
   intravenously or subcutaneously administering one or more subsequent doses, wherein each subsequent dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg of the antibody to the subject,
   wherein the antibody comprises a heavy chain and a light chain, wherein the heavy chain comprises a HCDR1 of SEQ ID NO: 7, a HCDR2 of SEQ ID NO: 8, and a HCDR3 of SEQ ID NO: 9 and the light chain comprises a LCDR1 of SEQ ID NO: 4, a LCDR2 of SEQ ID NO: 5 and a LCDR3 of SEQ ID NO: 6; or
   wherein the antibody comprises a light chain comprising a variable region having the amino acid sequence of SEQ ID NO: 2 and a heavy chain comprises a variable region sequence having the amino acid sequence of of SEQ ID NO: 3; or
   wherein the antibody comprises a light chain comprising an amino acid sequence of SEQ ID NO: 11 and a heavy chain comprising an amino acid sequence of SEQ ID NO: 10.

2. The method of claim 1, wherein the first dose is about 2 mg/kg.
3. The method of claim 1, wherein the first dose is about 3 mg/kg.
4. The method of claim 1, wherein the first dose is about 2.5 mg/kg.
5. The method of claim 1, wherein the first dose is about 5 mg/kg.
6. The method of claim 1, wherein the first dose is about 7.5 mg/kg.
7. The method of claim 1, wherein first dose is about 10 mg/kg.
8. The method of claim 1, wherein first dose is about 15 mg/kg.
9. The method of claim 1, wherein the first dose is about 20 mg/kg.
10. The method of any one of claims 2-9, wherein the one or more subsequent dose amounts is the same as the first dose amount.
11. The method of any one of claims 2-9, wherein the one or more subsequent dose amounts is different from the first dose amount.
12. The method of any one of claims 2-11, wherein at least one subsequent dose of the one or more subsequent doses is about 2 mg/kg.
13. The method of any one of claims 2-11, wherein at least one subsequent dose of the one or more subsequent doses is about 3 mg/kg.
14. The method of any one of claims 2-11, wherein at least one subsequent dose of the one or more subsequent doses is about 5 mg/kg.
15. The method of any one of claims 2-11, wherein at least one subsequent dose of the one or more subsequent doses is about 7.5 mg/kg.
16. The method of any one of claims 2-11, wherein at least one subsequent dose of the one or more subsequent doses is about 10 mg/kg.
17. The method of any one of claims 2-11, wherein at least one subsequent dose of the one or more subsequent doses is about 15 mg/kg.
18. The method of any one of claims 2-11, wherein at least one subsequent dose of the one or more subsequent doses is about 20 mg/kg.
19. The method of any one of claims 1-18, wherein at least one subsequent dose of the one or more subsequent doses is administered one, two, three, four, five, six, or eight weeks after the first dose.

20. The method of any one of claims 1-19, wherein only one, two, three, four, five, six or seven subsequent doses are administered to the subject.

21. The method of any one of claims 1-20, comprising administering a total of two, three, four, five, six, seven or eight doses to the subject.

22. The method of any one of claims 1-21, wherein after two or three doses of the antibody, the clinical activity score of the subject is reduced.

23. The method of any one of claims 1-22 wherein each subsequent dose is administered one, two, three, four, five, six, seven, or eight weeks after a previous dose.

24. The method of any one of claims 1-23, comprising administering at least one dose by intravenous infusion over 45 minutes to about 90 minutes, or over 60 minutes to about 90 minutes.

25. The method of any one of claims 1-24, comprising administering at least one dose by subcutaneous administration.

26. The method of claim 25, wherein the subcutaneous administering is self-administering.

27. The method of any one of claims 1-26, further comprising administering one or more loading doses of the antibody to the subject before administering the first dose.

28. The method of any one of claims 1-26, further comprising administering a first loading dose of the antibody to the subject, before administering the first dose, wherein the first loading dose is selected from the group consisting of about 5 mg/kg to about 7.5 mg/kg, about 7.5 mg/kg to about 10 mg/kg, about 10 mg/kg to about 12.5 mg/kg, or about 12.5 mg/kg to about 15 mg/kg.

29. The method of claim 27 or 28, wherein a second loading dose of the antibody is administered to the subject after the first loading dose, and wherein the first and second loading doses are administered before the first dose.

30. The method of claim 29, wherein the first loading dose and the second loading doses are the same dose amount.

31. The method of claim 29, wherein the first loading dose and the second loading dose are different dose amounts.

32. The method of any one of claims 27-31, wherein the first loading dose is about 5 mg/kg.

33. The method of any one of claims 27-31, wherein the first loading dose is about 7.5 mg/kg.

34. The method of any one of claims 27-31, wherein the first loading dose is about 10 mg/kg.

35. The method of any one of claims 27-31, wherein the first loading dose is about 12.5 mg/kg.

36. The method of any one of claims 27-31, wherein the first loading dose is about 15 mg/kg.

37. The method of any one of claims 27-36, wherein the second loading dose is about 5 mg/kg.

38. The method of any one of claims 27-36, wherein the second loading dose is about 7.5 mg/kg.

39. The method of any one of claims 27-36, wherein the second loading dose is about 10 mg/kg.

40. The method of any one of claims 27-36, wherein the second loading dose is about 12.5 mg/kg.

41. The method of any one of claims 27-36, wherein the second loading dose is about 15 mg/kg.

42. The method of any one of claims 27-41, wherein the first loading dose is administered to the subject one, two, three, or four weeks before the first dose is administered.

43. The method of any one of claims 1-42, wherein the antibody is administered as part of a pharmaceutically acceptable composition comprising the antibody and at least one pharmaceutically acceptable excipient, wherein the antibody has at least about 150 mg/ml solubility in the pharmaceutically acceptable composition.

44. The method of any one of claims 1-43, wherein the subject has had an unsatisfactory response to a prior therapeutic for the thyroid associated ophthalmopathy.

45. The method of claim 44, wherein the unsatisfactory response is one or more of: failure to reduce proptosis by 2 mm or more; failure to reduce CAS on one or more components or by 2 or more points; deterioration of 2 mm or more in the other eye; failure to reduce diplopia; failure to continue to improve diplopia for a period of time; failure to improve a score on Graves' Ophthalmopathy Quality of Life (GO-QoL) assessment by 8 or more points; and combinations thereof.

46. A method of treating thyroid associated ophthalmopathy in a subject in need thereof comprising:
intravenously or subcutaneously administering a first dose, wherein the first dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg, of an antibody to the subject, and
intravenously or subcutaneously administering one or more subsequent doses, wherein each subsequent dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg of the antibody to the subject, wherein the antibody is as provided herein, including, but not limited to:
wherein the antibody comprises a heavy chain and a light chain, wherein the heavy chain comprises a HCDR1 of SEQ ID NO: 7, a HCDR2 of SEQ ID NO: 8, and a HCDR3 of SEQ ID NO: 9 and the light chain comprises a LCDR1 of SEQ ID NO: 4, a LCDR2 of SEQ ID NO: 5 and a LCDR3 of SEQ ID NO: 6; or
wherein the antibody comprises a light chain comprising a variable region having the amino acid sequence of SEQ ID NO: 2 and a heavy chain comprises a variable region sequence having the amino acid sequence of of SEQ ID NO: 3; or
wherein the antibody comprises a light chain comprising an amino acid sequence of SEQ ID NO: 11 and a heavy chain comprising an amino acid sequence of SEQ ID NO: 10,
wherein the one or more subsequent doses is administered when the subject does not have an adequate response to one or more prior doses, as determined by measurement of clinical activity score and/or proptosis.

47. A method of improving a treatment of thyroid associated ophthalmopathy in a subject previously administered one or more treatments comprising:

intravenously or subcutaneously administering at least one dose consisting of about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg, of an antibody to the subject, wherein the antibody is represented by as antibody as provided herein, such as, wherein the antibody comprises a heavy chain and a light chain, wherein the heavy chain comprises a HCDR1 of SEQ ID NO: 7, a HCDR2 of SEQ ID NO: 8, and a HCDR3 of SEQ ID NO: 9 and the light chain comprises a LCDR1 of SEQ ID NO: 4, a LCDR2 of SEQ ID NO: 5 and a LCDR3 of SEQ ID NO: 6; or wherein the antibody comprises a light chain comprising a variable region having the amino acid sequence of SEQ ID NO: 2 and a heavy chain comprises a variable region sequence having the amino acid sequence of of SEQ ID NO: 3; or wherein the antibody comprises a light chain comprising an amino acid sequence of SEQ ID NO: 11 and a heavy chain comprising an amino acid sequence of SEQ ID NO: 10, wherein the at least one dose results in an improvement on one or more measurements relative to one or more measurements prior to the at least one dose.

48. The method of claim 47, wherein the one or more measurements is selected from proptosis, CAS, level of deterioration in the other eye, Score on GO-QOL, and combinations thereof.

49. The method of claim 47 or 48, wherein if the subject does not have a satisfactory response after the at least one dose, the subject is administered one or more subsequent doses each selected from the group consisting of about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg of the antibody to the subject.

50. The method of claim 49, wherein the one or more subsequent doses improves one or of proptosis, CAS, level of deterioration in the other eye, Score on GO-QOL, and combinations thereof, as compared to prior to the one or more subsequent doses.

51. A method of treating thyroid associated ophthalmopathy in a subject in need thereof, comprising:
intravenously or subcutaneously administering a first dose, wherein the first dose is selected from the group consisting of: about 250 mg, about 300 mg, about 350 mg, or about 400 mg of an antibody to the subject, and
intravenously or subcutaneously administering one or more subsequent doses, wherein each subsequent dose is selected from the group consisting of: about 250 mg, about 300 mg, about 350 mg, or about 400 mg of the antibody to the subject, wherein the antibody is represented by SEQ ID NO: 1.

52. The method of claim 51, wherein the first dose is about 250 mg.

53. The method of claim 52, wherein the first dose is about 300 mg.

54. The method of claim 52, wherein the first dose is about 350 mg.

55. The method of claim 52, wherein the first dose is about 400 mg.

56. The method of any one of claims 51-55, wherein the first dose amount and the one or more subsequent dose amounts are the same dose amounts.

57. The method of any one of claims 51-55, wherein the first dose amount and the one or more subsequent dose amounts are different dose amounts.

58. The method of any one of claims 51-57, wherein at least one subsequent dose of the one or more subsequent doses is about 250 mg.

59. The method of any one of claims 51-57, wherein at least one subsequent dose of the one or more subsequent doses is about 300 mg.

60. The method of any one of claims 51-57, wherein at least one subsequent dose of the one or more subsequent doses is about 350 mg.

61. The method of any one of claims 51-57, wherein at least one subsequent dose of the one or more subsequent doses is about 400 mg.

62. The method of any one of claims 51-61, wherein at least one subsequent dose of the one or more subsequent doses is administered one, two, three, four, five, six, or eight weeks after the first dose.

63. The method of any one of claims 51-62, wherein only one, two, three, four, five, six or seven subsequent doses are administered to the subject.

64. The method of any one of claims 51-63, comprising administering a total of two, three, four, five, six, seven or eight doses to the subject.

65. The method of any one of claims 51-64, wherein after two or three doses of the antibody, the clinical activity score of the subject is reduced.

66. The method of any one of claims 51-65 wherein each subsequent dose is administered one, two, three, four, five, six, seven, or eight weeks after a previous dose.

67. The method of any one of claims 51-66, comprising administering at least one dose by intravenous infusion over 45 minutes to about 90 minutes, or over 60 minutes to about 90 minutes.

68. The method of any one of claims 51-67, comprising administering at least one dose by subcutaneous administration.

69. The method of claim 68, wherein the subcutaneous administering is self-administering.

70. The method of any one of claims 51-69, further comprising administering one or more loading doses of the antibody to the subject before administering the first dose.

71. The method of any one of claims 51-69, further comprising administering a first loading dose of the antibody to the subject, before administering the first dose, wherein the first loading dose is selected from the group consisting of about 250 mg, about 300 mg, about 350 mg, or about 400 mg.

72. The method of claim 70 or 71, wherein a second loading dose of the antibody is administered to the subject after the first loading dose, and wherein the first and second loading doses are administered before the first dose.

73. The method of claim 72, wherein the first loading dose and the second loading doses are the same dose amount.

74. The method of claim 73, wherein the first loading dose and the second loading dose are different dose amounts.

75. The method of any one of claims 70-73, wherein the first loading dose is about 250 mg.

76. The method of any one of claims 70-73, wherein the first loading dose is about 300 mg.

77. The method of any one of claims 70-73, wherein the first loading dose is about 350 mg.
78. The method of any one of claims 70-73, wherein the first loading dose is about 400 mg.
79. The method of any one of claims 70-78, wherein the second loading dose is about 250 mg. 80. The method of any one of claims 70-78, wherein the second loading dose is about 300 mg.
81. The method of any one of claims 70-78, wherein the second loading dose is about 350 mg.
82. The method of any one of claims 70-78, wherein the second loading dose is about 400 mg.
83. The method of any one of claims 70-78, wherein the first loading dose is administered to the subject one, two, three, or four weeks before the first dose is administered.
84. The method of any one of claims 51-83, wherein the antibody is administered as part of a pharmaceutically acceptable composition comprising the antibody and at least one pharmaceutically acceptable excipient, wherein the antibody has at least about 150 mg/ml solubility in the pharmaceutically acceptable composition.
85. The method of any one of claims 51-84, wherein the subject has had an unsatisfactory response to a prior therapeutic for the thyroid associated ophthalmopathy.
86. The method of claim 85, wherein the unsatisfactory response is selected from failure to reduce proptosis by 2 mm or more; failure to reduce CAS on one or more components or by 2 or more points; deterioration of 2 mm or more in the other eye; failure to reduce diplopia; failure to continue to improve diplopia for a period of time; failure to improve a score on Graves' Ophthalmopathy Quality of Life (GO-QoL) assessment by 8 or more points; and combinations thereof.
87. The method of any one of claim 27-45 or 70-86, wherein the first loading dose and the second loading dose are administered between about one, about two, or about three weeks apart.
88. The method of claim 87, wherein the second loading dose is administered about one, about two, or about three weeks before the first dose.
89. A method of treating thyroid associated ophthalmopathy in a subject in need thereof, comprising:
intravenously or subcutaneously administering a first dose, wherein the first dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg, of an antibody to the subject; and
intravenously or subcutaneously administering one or more subsequent doses, wherein each subsequent dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg of the antibody to the subject,
wherein the antibody comprises a heavy chain and a light chain, wherein the heavy chain comprises a HCDR1 of SEQ ID NO: 7, a HCDR2 of SEQ ID NO: 8, and a HCDR3 of SEQ ID NO: 9 and the light chain comprises a LCDR1 of SEQ ID NO: 4, a LCDR2 of SEQ ID NO: 5 and a LCDR3 of SEQ ID NO: 6.

90. The method of embodiment 89, wherein the light chain comprises a variable region having the amino acid sequence of SEQ ID NO: 2 and the heavy chain comprises a variable region sequence having the amino acid sequence of of SEQ ID NO: 3.
91. The method of embodiments 89 or 90, wherein the light chain comprises an amino acid sequence of SEQ ID NO: 11.
92. The method of any one of embodiments 89-91, wherein the heavy chain comprises an amino acid sequence of SEQ ID NO: 10.
93. The method of embodiment 89, wherein the first dose is about 10 mg/kg.
94. The method of embodiment 93, wherein the one or more subsequent doses is about 10 mg/kg.
95. The method of any one of embodiments 89-93, wherein the one or more subsequent dose amounts is the same as the first dose amount.
96. The method of any one of embodiments 89-94, wherein the one or more subsequent dose amounts is different from the first dose amount.
97. The method of any one of embodiments 89-96, wherein at least one subsequent dose of the one or more subsequent doses is administered one, two, three, four, five, six, or eight weeks after the first dose.
98. The method of embodiment 94, wherein the one or more subsequent doses of the one or more subsequent doses is administered three weeks after the first dose.
99. The method of embodiment 94, wherein the subsequent dose is administered every three weeks after the first dose for 4, 5, 6, 7, or 8 cycles.
100. The method of embodiment 94, wherein the subsequent dose is administered every three weeks after the first dose for 5 or 8 cycles.
101. The method of embodiment 94, wherein the method comprises administering a total of five, six, seven or eight doses to the subject.
102. The method of any one of embodiments 89-101, wherein after first dose of the antibody, the clinical activity score of the subject is reduced.
103. The method of any one of embodiments 89-102, wherein after two doses of the antibody, the clinical activity score of the subject is reduced.
104. The method of embodiments 89-103, wherein after the one or more subsequence dose, the clinical activity score of the subject is reduced within 6 weeks of the first dose.
105. The method of embodiments 89-103, wherein after the one or more subsequence dose, the clinical activity score of the subject is reduced within 3 weeks of an initial one or more subsequent doses.
106. The method of any one of embodiments 89-105, wherein the antibody is administered by intravenous infusion over 45 minutes to about 90 minutes, or over 60 minutes to about 90 minutes.
107. The method of embodiment 89, wherein the first dose is about 10 mg/kg and the one or more subsequent doses is about 10 mg/kg.
108. The method of any one of embodiments 89-106, wherein the antibody is administered as part of a pharmaceutically acceptable composition comprising the antibody and at least one pharmaceutically acceptable excipient, wherein the pharmaceutical composition composition comprises the antibody at a concentration of 20 mg/mL to about 30 mg/mL.

109. The method of embodiment 108, wherein the pharmaceutical composition comprises the antibody at a concentration of about 25 mg/mL.
110. The method of any one of embodiments 89-109, wherein the treated subject's proptosis is reduced by at least, or about, 1-4 mm.
111. The method of embodiment 110, wherein the proptosis is reduced by at least, or about 2-3 mm.
112. The method of embodiments 110 or 111, wherein the proptosis is reduced within 3 weeks of the first dose.
113. The method of embodiments 110 or 111, wherein the proptosis is reduced within 6 weeks of the first dose.
114. The method of any one of embodiments 89-113, wherein the treated subject has reduced diplopia.
115. The method of embodiment 114, wherein the diplopia is reduced within 3 weeks or 6 weeks of the first dose.
116. The method of any one of embodiments 89-115, wherein the subject has an improvement in Clinical Activity Score (CAS) within 3 weeks or 6 weeks.
117. The method of embodiment 37, wherein the CAS score has an improvement of at least −2, −3, or −4.
118. The method of any one of embodiments 89-117, wherein the subject has a reduction in proptosis and an improvement in CAS score within 3 weeks or within 6 weeks of the first dose.
119. A method of treating thyroid associated ophthalmopathy in a subject in need thereof, comprising:
intravenously administering a first dose of 10 mg/kg of an antibody to the subject,
wherein the antibody comprises a heavy chain and a light chain, wherein the heavy chain comprises a HCDR1 of SEQ ID NO: 7, a HCDR2 of SEQ ID NO: 8, and a HCDR3 of SEQ ID NO: 9 and the light chain comprises a LCDR1 of SEQ ID NO: 4, a LCDR2 of SEQ ID NO: 5 and a LCDR3 of SEQ ID NO: 6.
120. The method of embodiment 119, wherein the light chain comprises a variable region having the amino acid sequence of SEQ ID NO: 2 and the heavy chain comprises a variable region sequence having the amino acid sequence of of SEQ ID NO: 3.
121. The method of embodiment 119, wherein the light chain comprises an amino acid sequence of SEQ ID NO: 11.
122. The method of embodiment 119, wherein the heavy chain comprises an amino acid sequence of SEQ ID NO: 10.
123. The method of embodiment 119, wherein the heavy chain comprises an amino acid sequence of SEQ ID NO: 10 and the light chain comprises an amino acid sequence of SEQ ID NO: 11.
124. The method of any one of embodiments 119-123, wherein the method further comprises administering a subsequent dose of about 10 mg/kg.
125. The method of embodiment 124, wherein the subsequent dose is administered about 3 weeks after the first dose.
126. The method of any one of embodiments 119-125, wherein the method further comprises administering a subsequent dose of about 10 mg/kg every 3 weeks after the first dose.
127. The method of embodiment 126, wherein the subsequent dose is administered every 3 weeks for a total of 4 subsequent doses.
128. The method of embodiment 126, wherein the subsequent dose is administered every 3 weeks for a total of 7 subsequent doses.
129. The method of any one of embodiments 119-128, wherein the subject's proptosis is reduced by at least, or about, 1-4 mm.
130. The method of embodiment 129, wherein the proptosis is reduced by at least, or about 2-3 mm.
131. The method of embodiments 129 or 130, wherein the proptosis is reduced within 3 weeks of the first dose.
132. The method of embodiments 129 or 130, wherein the proptosis is reduced within 6 weeks of the first dose.
133. The method of any one of embodiments 119-132, wherein the treated subject has reduced diplopia.
134. The method of embodiment 133, wherein the diplopia is reduced within 3 weeks or 6 weeks of the first dose.
135. The method of any one of embodiments 119-134, wherein the subject has an improvement in Clinical Activity Score (CAS) within 3 weeks or 6 weeks.
136. The method of embodiment 135, wherein the CAS score has an improvement of at least −2, −3, or −4.
137. The method of any one of embodiments 119-136, wherein the subject has a reduction in proptosis and an improvement in CAS score within 3 weeks or within 6 weeks of the first dose.
138. A method of treating thyroid associated ophthalmopathy in a subject in need thereof, comprising:
intravenously administering a dose of 10 mg/kg of an anti-IGF-1R antibody to the subject at a regular interval for a period sufficient to reduce one or more symptoms associated with thyroid associated ophthalmopathy,
wherein the anti-IGF-1R antibody comprises a heavy chain comprising a HCDR1 of SEQ ID NO: 7, a HCDR2 of SEQ ID NO: 8, and a HCDR3 of SEQ ID NO: 9 and a light chain comprising a LCDR1 of SEQ ID NO: 4, a LCDR2 of SEQ ID NO: 5 and a LCDR3 of SEQ ID NO: 6.
139. The method of embodiment 138, wherein the anti-IGF-1R antibody comprises a light chain and a heavy chain, wherein the light chain comprises a variable region having the amino acid sequence of SEQ ID NO: 2 and the heavy chain comprises a variable region having the amino acid sequence of SEQ ID NO: 3.
140. The method of embodiment 138, wherein the light chain comprises an amino acid sequence of SEQ ID NO: 11.
141. The method of embodiment 138, wherein the heavy chain comprises an amino acid sequence of SEQ ID NO: 10.
142. The method of embodiment 138, wherein the heavy chain comprises an amino acid sequence of SEQ ID NO: 10 and the light chain comprises an amino acid sequence of SEQ ID NO: 11.
143. The method of any one of embodiments 138-142, wherein the anti-IGF-1R antibody is administered by intravenous infusion.
144. The method of any one of embodiments 138-143, wherein the anti-IGF-1R antibody is administered every 3 weeks.
145. The method of any one of embodiments 138-144, wherein the anti-IGF-1R antibody is administered for a period sufficient for 5 doses.
146. The method of any one of embodiments 138-144, wherein the anti-IGF-1R antibody is administered for a period sufficient for 8 doses.
147. The method of any one of embodiments 138-144, wherein the anti-IGF-1R antibody is administered for a period selected from 3 weeks, 6 weeks, 9 weeks, 12 weeks, 15 weeks, 18 weeks, 21 weeks, 24 weeks or longer.

148. The method of any one of embodiments 138-147, wherein the subject's proptosis is reduced by at least, or about, 1-4 mm.

149. The method of embodiment 148, wherein the proptosis is reduced by at least, or about 2-3 mm.

150. The method of embodiments 148 or 149, wherein the proptosis is reduced within 3 weeks of the first dose.

151. The method of embodiment 148 or 149, wherein the proptosis is reduced within 6 weeks of the first dose.

152. The method of any one of embodiments 148-151, wherein the treated subject has reduced diplopia.

153. The method of embodiment 152, wherein the diplopia is reduced within 3 weeks or 6 weeks of the first dose.

154. The method of any one of embodiments 138-153, wherein the subject has an improvement in Clinical Activity Score (CAS) within 3 weeks or 6 weeks.

155. The method of embodiment 154, wherein the CAS score has an improvement of at least −2, −3, or −4.

156. The method of any one of embodiments 138-155, wherein the subject has a reduction in proptosis and an improvement in CAS score within 3 weeks or within 6 weeks of the first dose. 157. An antibody for use in the treatment of thyroid associated ophthalmopathy in a subject in need thereof, the antibody comprising a heavy chain and a light chain, wherein the heavy chain comprises a HCDR1 of SEQ ID NO: 7, a HCDR2 of SEQ ID NO: 8, and a HCDR3 of SEQ ID NO: 9 and the light chain comprises a LCDR1 of SEQ ID NO: 4, a LCDR2 of SEQ ID NO: 5 and a LCDR3 of SEQ ID NO: 6, wherein the antibody is administered intravenously or subcutaneously as a first dose, wherein the first dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg, of the antibody to the subject; and the antibody is administered intravenously or subcutaneously as one or more subsequent doses, wherein each subsequent dose is selected from the group consisting of: about 1 mg/kg to about 2 mg/kg, about 2 mg/kg to about 5 mg/kg, about 3 mg/kg to about 5 mg/kg, about 5 mg/kg to about 7.5 mg/kg, about 7.5 mg/kg to about 10 mg/kg, about 10 mg/kg to about 15 mg/kg, or about 15 mg/kg to about 20 mg/kg of the antibody to the subject.

158. The antibody of embodiment 157, wherein the light chain comprises a variable region having the amino acid sequence of SEQ ID NO: 2 and the heavy chain comprises a variable region sequence having the amino acid sequence of SEQ ID NO: 3.

159. The antibody of embodiments 157 or 158, wherein the light chain comprises an amino acid sequence of SEQ ID NO: 11.

160. The antibody of any one of embodiments 157-159, wherein the heavy chain comprises an amino acid sequence of SEQ ID NO: 10.

161. The antibody of embodiment 157, wherein the first dose is about 10 mg/kg.

162. The antibody of embodiment 161, wherein the one or more subsequent doses is about 10 mg/kg.

163. The antibody of any one of embodiments 157-161, wherein the one or more subsequent dose amounts is the same as the first dose amount.

164. The antibody of any one of embodiments 157-161, wherein the one or more subsequent dose amounts is different from the first dose amount.

165. The antibody of any one of embodiments 157-164, wherein at least one subsequent dose of the one or more subsequent doses is administered one, two, three, four, five, six, or eight weeks after the first dose.

166. The antibody of embodiment 165, wherein the one or more subsequent doses of the one or more subsequent doses is administered three weeks after the first dose.

167. The antibody of embodiment 165, wherein the subsequent dose is administered every three weeks after the first dose for 4, 5, 6, 7, or 8 cycles.

168. The antibody of embodiment 165, wherein the subsequent dose is administered every three weeks after the first dose for 5 or 8 cycles.

169. The antibody of embodiment 165, wherein the treatment comprises administering a total of five, six, seven or eight doses to the subject.

170. The antibody of any one of embodiments 157-169, wherein after first dose of the antibody, the clinical activity score of the subject is reduced.

171. The antibody of any one of embodiments 157-170, wherein after two doses of the antibody, the clinical activity score of the subject is reduced.

172. The antibody of embodiments 157-171, wherein after the one or more subsequence dose, the clinical activity score of the subject is reduced within 6 weeks of the first dose.

173. The antibody of embodiments 1-171, wherein after the one or more subsequence dose, the clinical activity score of the subject is reduced within 3 weeks of an initial one or more subsequent doses.

174. The antibody of any one of embodiments 1-173, wherein the antibody is administered by intravenous infusion over 45 minutes to about 90 minutes, or over 60 minutes to about 90 minutes.

175. The antibody of embodiment 157, wherein the first dose is about 10 mg/kg and the one or more subsequent doses is about 10 mg/kg.

176. The antibody of any one of embodiments 157-19, wherein the antibody is administered as part of a pharmaceutically acceptable composition comprising the antibody and at least one pharmaceutically acceptable excipient, wherein the pharmaceutical composition comprises the antibody at a concentration of 20 mg/mL to about 30 mg/mL.

177. The antibody of embodiment 176, wherein the pharmaceutical composition comprises the antibody at a concentration of about 25 mg/mL.

178. The antibody of any one of embodiments 157-177, wherein the treated subject's proptosis is reduced by at least, or about, 1-4 mm.

179. The antibody of embodiment 178, wherein the proptosis is reduced by at least, or about 2-3 mm.

180. The antibody of embodiments 178 or 179, wherein the proptosis is reduced within 3 weeks of the first dose.

181. The antibody of embodiments 178 or 179, wherein the proptosis is reduced within 6 weeks of the first dose.

182. The antibody of any one of embodiments 157-181, wherein the treated subject has reduced diplopia.

183. The antibody of embodiment 182, wherein the diplopia is reduced within 3 weeks or 6 weeks of the first dose.

184. The antibody of any one of embodiments 157-183, wherein the subject has an improvement in Clinical Activity Score (CAS) within 3 weeks or 6 weeks.
185. The antibody of embodiment 184, wherein the CAS score has an improvement of at least −2, −3, or −4.
186. The antibody of any one of embodiments 157-185, wherein the subject has a reduction in proptosis and an improvement in CAS score within 3 weeks or within 6 weeks of the first dose.
187. An anti-IGF-1R antibody for use in the treatment of treating thyroid associated ophthalmopathy in a subject in need thereof, the anti-IGF-1R antibody comprising a heavy chain com a HCDR1 of SEQ ID NO: 7, a HCDR2 of SEQ ID NO: 8, and a HCDR3 of SEQ ID NO: 9 and a light chain comprising a LCDR1 of SEQ ID NO: 4, a LCDR2 of SEQ ID NO: 5 and a LCDR3 of SEQ ID NO: 6, and wherein
the anti-IGF-1R antibody is administered intravenously as a dose of 10 mg/kg of the anti-IGF-1R antibody to the subject at a regular interval for a period sufficient to reduce one or more symptoms associated with thyroid associated ophthalmopathy.
188. The antibody of embodiment 187, wherein the anti-IGF-1R antibody comprises a light chain and a heavy chain, wherein the light chain comprises a variable region having the amino acid sequence of SEQ ID NO: 2 and the heavy chain comprises a variable region having the amino acid sequence of SEQ ID NO: 3.
189. The antibody of embodiment 187, wherein the light chain comprises an amino acid sequence of SEQ ID NO: 11.
190. The antibody of embodiment 187, wherein the heavy chain comprises an amino acid sequence of SEQ ID NO: 10.
191. The antibody of embodiment 187, wherein the heavy chain comprises an amino acid sequence of SEQ ID NO: 10 and the light chain comprises an amino acid sequence of SEQ ID NO: 11.
192. The antibody of any one of embodiments 187-191, wherein the anti-IGF-1R antibody is administered by intravenous infusion.
193. The antibody of any one of embodiments 187-192, wherein the anti-IGF-1R antibody is administered every 3 weeks.
194. The antibody of any one of embodiments 187-193, wherein the anti-IGF-1R antibody is administered for a period sufficient for 5 doses.
195. The antibody of any one of embodiments 187-193, wherein the anti-IGF-1R antibody is administered for a period sufficient for 8 doses.
196. The antibody of any one of embodiments 187-195, wherein the anti-IGF-1R antibody is administered for a period selected from 3 weeks, 6 weeks, 9 weeks, 12 weeks, 15 weeks, 18 weeks, 21 weeks, 24 weeks or longer.
197. The antibody of any one of embodiments 187-196, wherein the subject's proptosis is reduced by at least, or about, 1-4 mm.
198. The antibody of embodiment 197, wherein the proptosis is reduced by at least, or about 2-3 mm.
199. The antibody of embodiments 197 or 198, wherein the proptosis is reduced within 3 weeks of the first dose.
200. The antibody of embodiments 197 or 198, wherein the proptosis is reduced within 6 weeks of the first dose.
201. The antibody of any one of embodiments 187-200, wherein the treated subject has reduced diplopia.
202. The antibody of embodiment 201, wherein the diplopia is reduced within 3 weeks or 6 weeks of the first dose.
203. The antibody of any one of embodiments 187-202, wherein the subject has an improvement in Clinical Activity Score (CAS) within 3 weeks or 6 weeks.
204. The antibody of embodiment 203, wherein the CAS score has an improvement of at least −2, −3, or −4.
205. The antibody of any one of embodiments 187-204, wherein the subject has a reduction in proptosis and an improvement in CAS score within 3 weeks or within 6 weeks of the first dose.

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1: VRDN-5000 Binds Better and Shows Increased Antagonism as Compared to Teprotumumab In vitro cell-based assays were performed in two different IFG1R-expressing cell lines: A549 cells (FIGS. 1A and 1B) and Human Ocular Choroid Fibroblasts (HOCF) cells (FIGS. 1C and 1D).

In cell-based antibody binding assays, VRDN-5000, which can also be referred to as VRDN-001, consistently showed increased binding levels as concentrations of antibody increased (as measured by mean fluorescence intensity) as compared to teprotumumab or an IgG control in both A549 (FIG. 1A; solid circles: VRDN-001; triangles: teprotumumab; hollow circles: IgG) and HOCF (FIG. 1C; solid circles=VRDN; triangles: teprotumumab; hollow circles: IgG) cells.

Figure 1B:
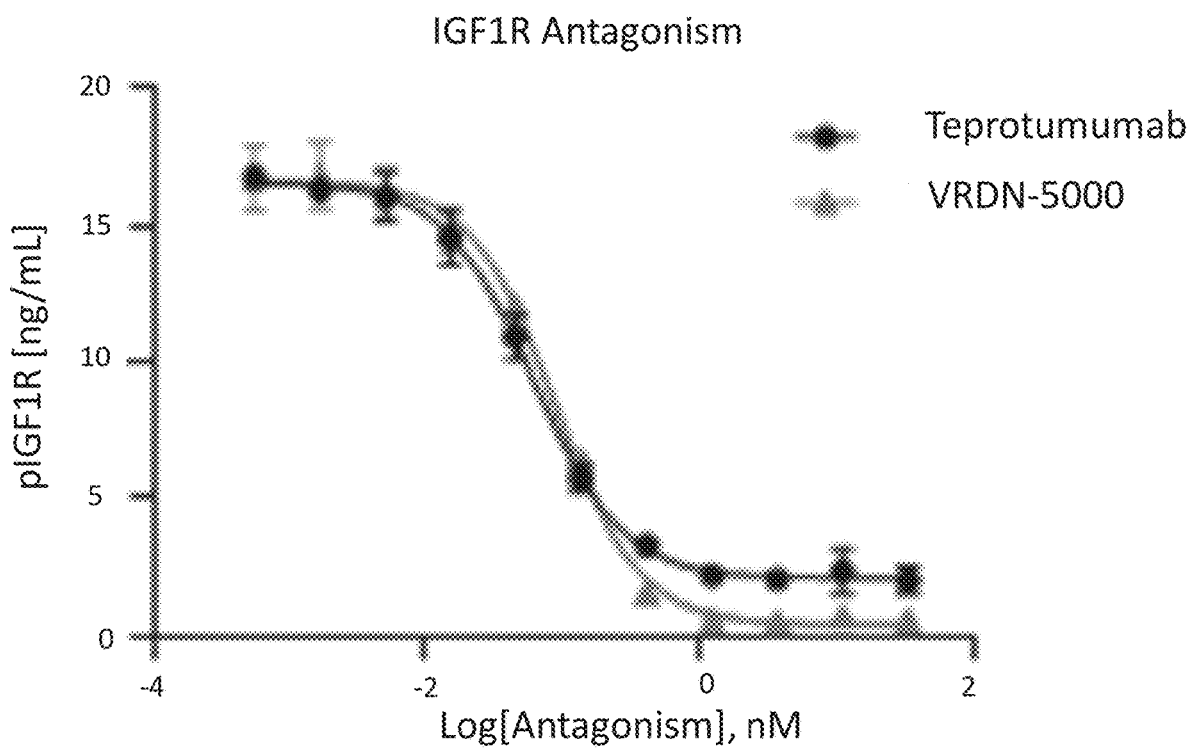
Figure 1C:
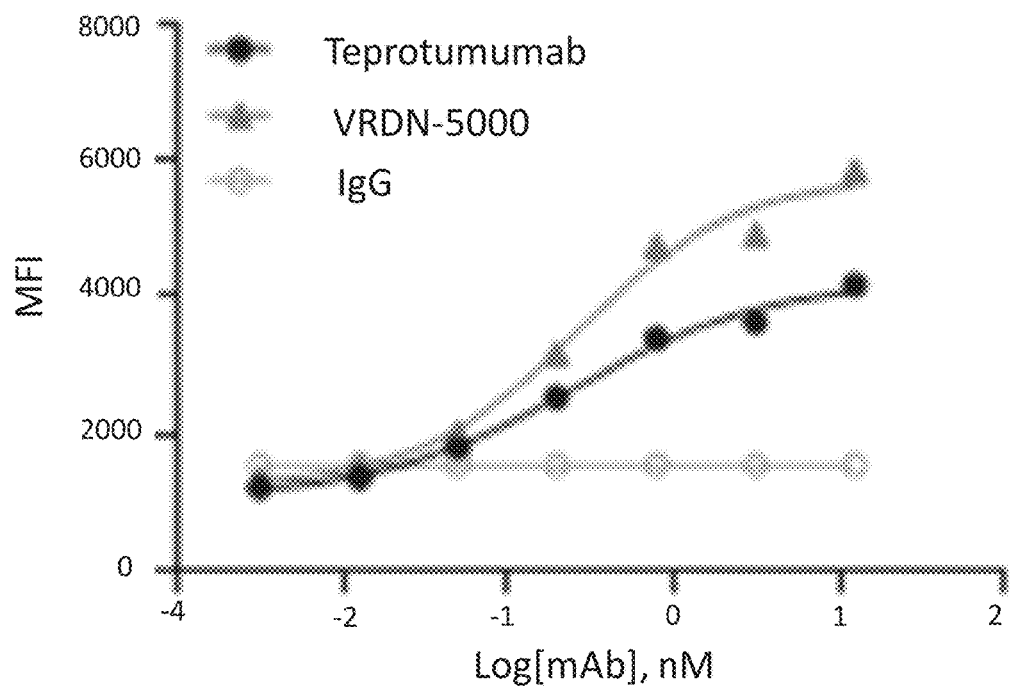
Figure 1D:
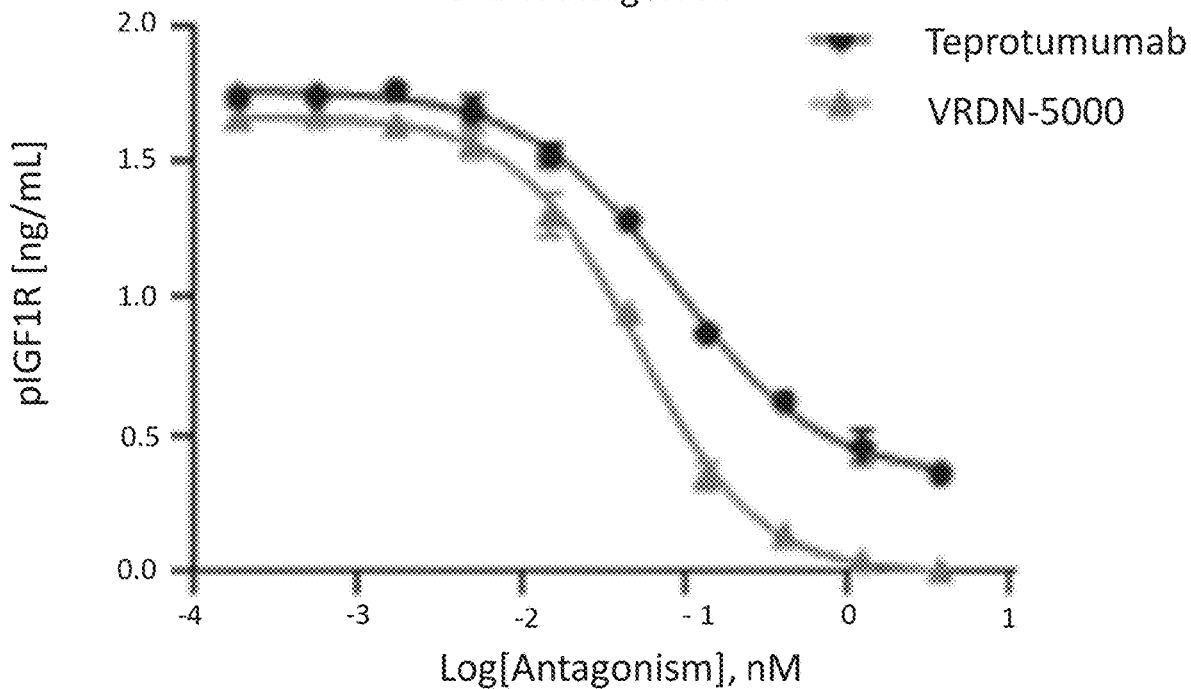

Similarly, VRDN-5000 consistently showed increased antagonism at increasing concentrations of antibody (as measured by mean fluorescence intensity) as compared to teprotumumab in both A549 (FIG. 1B; solid circles: VRDN-001; triangles: teprotumumab) and HOCF (FIG. 1D; solid circles=VRDN; triangles: teprotumumab) cells.

VRDN-5000 binds to IGFR1 more strongly and exerts stronger antagonistic effects than teprotumumab at antibody concentrations picomolar and nanomolar concentrations of antibody.

Example 2: Treatment of Patients with Thyroid Eye Disease and Clinical Assessment of IGF-1R Antibodies on Thyroid Eye Disease Infusions of VRDN-5000 as disclosed herein, are provided to the subjects. The number of infusions is individualized for each subject and is based on the investigator's clinical judgment. The Day 1 Visit occurs within 14 days after the final visit of the prior trial. Visit windows are ±1 day for Weeks 1 and 4, ±3 days for Weeks 3, 6, 9, 12, 15, 18, 21, and 24. The Follow-up period is meant for subjects who were proptosis non-responders in the prior trial only; subjects who relapsed in the prior trial did not participate in the Follow-Up Period. Visit windows during the Follow-up period are ±7 days.

Treatment Period is 24 weeks (6 months), during which 8 infusions of teprotumumab are administered.

Subjects who are proptosis non-responders are scheduled to participate in a 6-month Follow-Up Period in this extension study; subjects who relapsed in the lead-in study and are retreated in this extension study will not participate in the Follow-Up Period.

Efficacy assessments are performed for both eyes at each assessment time point. The "study eye" (i.e., the more severely affected eye) will remain the same as that identified at the Baseline (Day 1) Visit of the prior study. Both eyes are assessed for efficacy but the study eye is used to assess the primary outcome measure.

Efficacy is assessed by proptosis (measured as exophthalmos evaluation of the Clinical Measures of Severity using a Hertel instrument for consistency in measurement), CAS (7-item scale), diplopia (measured as part of the Clinical Measures of Severity) and Clinical Measures of Severity (including motility restriction assessments).

Quality of life is assessed using the GO-QoL questionnaire.

Safety is assessed via AE and concomitant medication use monitoring, immunogenicity testing, physical and ophthalmic examinations, vital signs, clinical safety laboratory evaluations (complete blood count, chemistry (including thyroid panel and HbA1C), and urinalysis), pregnancy testing (if applicable), and electrocardiograms (ECG). The study is also monitored by a Data Safety Monitoring Board (DSMB).

Proptosis assessments is performed using a Hertel exophthalmometer for consistency in measurement, and (except when strictly unavoidable) the same Hertel instrument and same observer is used at each evaluation for the full duration of the study. Additionally, the same intercanthal distance (ICD) is used on each occasion.

Proptosis is measured for each eye on Day 1 and Weeks 6, 12, 18, and 24 (or premature withdrawal (PW)) during the Treatment Period, and at Months 7, 9, and 12 (or PW) during the Follow-Up Period. Measurements is recorded on the Clinical Measures of Severity eCRF under exophthalmos.

The antibodies are found to be effective in treating thyroid eye disease and also improving quality of life as provided for herein.

Example 3: Multiple Ascending Dose Safety and Efficacy Studies of Anti-IGF-1R in Normal Healthy Volunteers and Subjects with Thyroid Eye Disease (Ph1/2 Study)

Normal healthy volunteers (NHVs) and subjects with thyroid eye disease (TED subjects) are treated with VRDN-5000 to study safety, tolerability, preliminary efficacy, pharmacokinetic (PK) and pharmacodynamic (PD) profiles.

NHVs and subjects with TED are screened for eligibility prior to treatment commencement using inclusion and exclusion criteria for NHV and TED subjects. Intravenous infusions of VRDN-5000 (SEQ ID NO: 71) are provided to NHV and TED subjects. Each subject receives two infusions, at 3 mg/kg, 10 mg/kg or 20 mg/kg doses with each infusion separated by three weeks. Each infusion is administered over a 90 minute period. For a given subject the first dose and the second dose amounts are the same (e.g., a subject receives a first 3 mg/kg and a second dose of 3 mg/kg separated by 3 weeks, etc.). NHV subjects are monitored for six weeks following the first dose and TED subjects are monitored for 6 months following the first dose.

VRDN-5000 is provided as a solution of 25 mg/mL antibody in a 5.1 mL fill volume in a 6 mL clear single-dose glass vial with a rubber septum and aluminum seal and plastic cap. Storage is at 2-8° C. or frozen at −20° C.

VRDN-5000 is dosed in a range of 3 mg/kg to 20 mg/kg. All subjects (NHVs and subjects with TED) are monitored for safety, efficacy, and other endpoints.

Safety endpoints include Adverse Events (AEs), Serious Adverse Events (SAEs) and Laboratory Assessments, which are monitored and recorded throughout the duration of the study.

The Primary efficacy endpoint includes Proptosis Responder Rate (i.e., reduction of proptosis of ≥2 mm [Hertel] from baseline within the "study" [more proptotic] eye) at 6 and 12 weeks.

Other endpoints include VRDN-001, IGF-1 and ADA blood levels at various timepoints pre- and post-infusions and changes from baseline versus in volume of orbital fat as determined by magnetic resonance imaging (MRI); volume of extraocular muscles as determined by MRI; Clinical Activity Score (CAS); change in Subjective Diplopia Score; change in objective assessment of ocular motility as measured in the five cardinal positions of gaze via prism deviation; and change in Graves' Orbitopathy-Quality of Life (GO-QoL) score.

Dosing occurs at 21 day intervals. Up to 48 subjects participate in the multiple ascending dose trial (12-16 NHVs and 16-32 subjects with TED in multiple ascending dose studies).

Single dose PK measurements are determined following the first of the two infusions and repeat dose PK is determined following the second dose. PK and PD determinations are conducted in NHV subjects in order to minimize number of study visits required of TED subjects. Preliminary efficacy data are collected from TED subjects at 6, 12 and 24 weeks after the first of two infusions. Safety and tolerability data are collected from both NHV and TED subjects following treatment with VRDN-001. All measurements for NHV and TED subjects are performed as described herein.

The study is a randomized, double-masked (excluding sponsor), and placebo-controlled. Subjects and site personnel are masked to treatment. The pharmacist preparing the infusion bags is unmasked to treatment and issues 250 mL bags of saline with or without VRDN-5000 added, according to the Interactive Web Response System (IWRS). The 250 mL bags are infused over a 90-minute period.

Three dose levels are evaluated: 3 mg/kg ("low"), 10 mg/kg ("middle"), and 20 mg/kg ("high"). Each subject receives two doses, three weeks apart, with each dose administered by intravenous infusion. The dose amount given to each subject dose not differ between administrations (e.g., a subject receives a first 3 mg/kg dose and a second 3 mg/kg dose separated by 3 weeks, etc.)

The low dose cohort includes 4 NHVs randomized 3:1 (VRDN-5000 to placebo). middle and high dose cohorts include 4 NHVs and 8 TED subjects with each group randomized 3:1 (VRDN-5000 to placebo).

Two NHV subjects in the low dose cohort are treated and followed through 1 week after their first infusion before the second remaining 2 subjects of that cohort are treated. Dose limiting toxicity (DLT) is a drug-related safety event, the severity of which requires discontinuation of treatment and/or prevents dose escalation of VRDN-001. If a subject experiences a DLT, then an additional 4 NHV subjects are enrolled and escalation to the next dose occurs only if no further subjects experience a DLT.

One week after the fourth NHV subject of the low dose cohort receives their second infusion, escalation to the middle dose level commences after review of the safety data by the Data Safety Monitoring Board (DSMB). Two NHV subjects are then enrolled into the middle dose cohort and followed through 1 week after their first infusion before further NHV and TED subjects are enrolled at that dose level.

Escalation to the high dose level occurs once the fourth NHV subject at the middle dose cohort is followed for 1 week after their second infusion and providing that no more than 1 subject at that dose level has experienced a DLT. This occurs following review of the safety data by the DSMB. If both the middle and high dose cohorts exhibit similar evidence of clinical activity in terms of proptosis response rate, 8 TED subjects are enrolled at the low dose (3.0 mg/kg) and a further cohort of 12 subjects (4 NHVs and 8 TED subjects) are enrolled at an intermediate dose (5.0 mg/kg) in order to establish a dose response curve for clinical activity.

Study procedures for NHVs are as follows: All NHV subjects are screened within 28 days prior to treatment and have complete physical examinations and ECG to exclude any abnormalities that would preclude participation in the study. Subjects are admitted to the clinical pharmacology unit 24 hours prior to each infusion and remain for 7 days after each of the two infusions for PK sample collection. Subjects' vital signs and ECG (telemetry) are monitored continuously during the infusions and the cutaneous infusion site is examined periodically for local tolerance. Subjects return to the unit at specified time points for further blood sampling and assessments as outlined below. A web based supervised audiometry test is performed before and 3 weeks after each infusion.

Blood samples for PK analyses and measurement of IGF-1 levels are taken by an indwelling venous cannula inserted in the opposite forearm to the infusion arm. PK samples are collected before starting each infusion, at 5 minutes before the end of the infusion and at 2, 4, 8, and 12 hours post-infusion, and further samples collected at 1, 3, 7, 14, and 21 days following each infusion; a final sample is collected 28 days after the second infusion. Blood samples for IGF-1 levels are collected before each infusion and on 1, 2, 3, 7, 14, and 21 days after each infusion. Additional blood samples are collected for measurement of anti-drug antibodies (ADAs) prior to each infusion of VRDN-001, and again 21 days after each infusion. Fasting blood and urine samples are drawn for hematology, chemistry and coagulation parameters and standard urinalysis at screening, immediately before each infusion and 7 days after each infusion. NHVs have a full physical exam and ECG at their Week 7 visit.

Study procedures for TED subjects are as follows: TED subjects are screened for eligibility, history and duration of TED during a 28-day period prior to study entry. On the day before each infusion, subjects undergo proptosis measurement, CAS assessment, Diplopia Score assessment, prism measurement of ocular ductions in 5 positions of gaze, complete a GO-QoL questionnaire, fundoscopy, biomicroscopy, intraocular pressure (IOP) and audiometry. These assessments are repeated at the Day 43 and 85 (Weeks 6 and 12) follow-up visits. Subjects undergo a full physical examination and have an ECG recorded at screening and repeated at the Week 6 follow-up visit. An orbital MRI is performed within 3 days prior to both infusions and repeated within (+) 3 days either side of the visits at Weeks 6 and 12. Facial photography is performed at Screening and the Week 12 and 24 visits. Infusions are given to TED subjects at infusion clinics and subjects' vital signs and ECG are monitored continuously during the infusions. The cutaneous infusion site is examined periodically for local tolerance. Study site personnel telephone TED subjects the day after each infusion to ensure the subject's well-being and to inquire whether any AEs have occurred since their discharge from the infusion clinic the day before. Subjects are told to call the study site if they have any health concerns and additional study visits are arranged at the request of either the PI or the subjects. All ocular assessments are performed on both eyes. These assessments are performed immediately prior to each infusion on Days 1 and 21, and again 3 weeks after the second infusion. Follow-up visits for assessment of proptosis occur at 12 and 24 weeks after the first infusion. The web based supervised audiometry test is performed before and 3 weeks after each infusion.

Blood samples for PK and IGF-1 levels are taken by an indwelling venous cannula inserted in the opposite forearm to the infusion arm before starting the first infusion, at 5 minutes before the end of the infusion and at 2- and 4-hours post-infusion and repeated at same timepoints for the second infusion. A further sample is taken on each of the Day 43 and 50 visits. Additional blood samples are taken for measurement of ADAs prior to each infusion and again 3 weeks after the second infusion. Fasting blood and urine samples are drawn for hematology, chemistry and coagulation parameters, and standard urinalysis at screening and 3 weeks after the first infusion (the day before the second infusion) and 3 weeks after the second infusion.

The antibodies are found to be safe in NHVs and both safe and effective in treating thyroid eye disease and also improving quality of life as provided for herein in subjects with TED.

Example 4: Extension Studies of Anti-IGF-1R in and Subjects with Thyroid Eye Disease Subjects with thyroid eye disease (TED subjects) are treated with VRDN-5000 in an extension study following completion of a prior study on safety, tolerability, preliminary efficacy, pharmacokinetic (PK) and pharmacodynamic (PD) profiles.

Intravenous infusions of VRDN-5000 are provided to TED subjects. Each subject receives two infusions, at 3 mg/kg, 10 mg/kg or 20 mg/kg doses with each infusion separated by three weeks. Each infusion is administered over a 90 minute period. For a given subject the first dose and the second dose are the same (e.g., first and second doses of 3 mg/kg; first and second doses of 10 mg/kg; or first and second doses of 20 mg/kg). TED subjects are monitored for 6 months following the first dose.

VRDN-5000 is provided as a solution of 25 mg/mL antibody in a 5.1 mL fill volume in a 6 mL clear single-dose glass vial with a rubber septum and aluminum seal and plastic cap. Storage is at 2-8° C. or frozen at −20° C.

VRDN-5000 is dosed in a range of 3 mg/kg to 20 mg/kg. All subjects are monitored for safety, efficacy, and other endpoints.

Safety endpoints include Adverse Events (AEs), Serious Adverse Events (SAEs) and Laboratory Assessments, which are monitored and recorded throughout the duration of the study.

The Primary efficacy endpoint includes Proptosis Responder Rate (i.e., reduction of proptosis of ≥2 mm [Hertel] from baseline within the "study" [more proptotic] eye) at 24 weeks.

Other endpoints include VRDN-001, IGF-1 and ADA blood levels at various timepoints pre- and post-infusions and changes from baseline versus in volume of orbital fat as determined by magnetic resonance imaging (MRI); volume of extraocular muscles as determined by MRI; Clinical Activity Score (CAS); change in Subjective Diplopia Score; change in objective assessment of ocular motility as measured in the five cardinal positions of gaze via prism deviation; and change in Graves' Orbitopathy-Quality of Life (GO-QoL) score.

Dosing occurs at 21 day intervals. Up to 48 subjects participate the extension study. Total number of subject depends upon results from the multiple ascending dose study in Example 3. If all 48 subjects are included, the extension study includes 3 randomized (1:1:1; 16 per cohort/arm) in a double-masked (including sponsor) placebo-controlled design, comparing two active treatment arms (4 versus 8 infusions) to placebo arm.

The extension study has 80% power to test each dose regimens versus placebo assuming a difference in reduction in proptosis of 50% for each active arm versus placebo. To this end, the 1-sided type-I error level of 0.025 is split evenly over both comparisons (Bonferonni correction), resulting in a pairwise type-I error level of 0.0125.

The extension study commences following completion of the multiple ascending dose study described in Example 3. This study continues investigation of clinical activity of VRDN-5000 at the lowest dose demonstrating a clinically meaningful efficacy signal in multiple ascending dose study of Example 3 and a dose response exploration is pursued.

Specific parameters for dose and regimen in extension cohorts is driven by data from the multiple ascending dose study in Example 3, including PK data determined therein. If tested doses in the multiple ascending dose study in Example 3 show equivalent efficacy signal, an additional lower dose cohort is explored. If not, one extension cohort compares 4 infusions to another extension cohort receiving 8 infusions at the selected dose; defined treatment durations in all extension cohorts are fully supported by toxicology data available at the time of first infusions.

Subjects in all three cohorts receive the same number of infusions to maintain masking. Ocular assessments are performed on both eyes and subjects have the following assessments performed: proptosis measurement, CAS assessment, Diplopia Score assessment, prism measurement of ocular ductions in 5 positions of gaze, complete a GO-QOL questionnaire, fundoscopy, biomicroscopy and IOP. These assessments are performed the day before each infusion and repeated at the Week 24 and 52 visits. A web based supervised audiometry test is performed 1 day before each infusion and again at the week 24 visit. An orbital MRI is performed within 3 days prior to the first infusion and repeated within (±) 3 days of the Week 12, 24, and 52 visits. Facial photography is performed at Screening, and the Week 24 and 52 visits. The infusions are given to the TED subjects at infusion clinics and subjects' vital signs and ECG are monitored continuously during the infusions. The cutaneous infusion site is examined periodically for local tolerance.

Blood samples for PK and IGF-1 levels are taken by an indwelling venous cannula inserted in the opposite forearm to the infusion arm before starting the first infusion, at 5 minutes before the end of the infusion and at 2- and 4-hours post-infusion, and further samples are taken on 1, 3, 7, 14 and 21 days after the infusion. These sampling times are repeated immediately before and after the fourth infusion. Single samples are taken before each infusion at Weeks 3, 6, 12, 15, 18 and 21. Further samples are taken at weeks 24, 25 and 52. Subjects are offered an option to have the blood samples drawn by a phlebotomist/nurse at the subject's home or place of work if visits to the investigational site prove to be inconvenient because of other commitments. Additional blood samples are taken for measurement of ADAs prior to each infusion and again at the visits at weeks 24, 25 and 52.

Fasting blood and urine samples are drawn for hematology, chemistry and coagulation parameters, and standard urinalysis at screening and again 3 weeks after the fourth (the visit the day before the Week 12 infusion) and eighth infusions (Week 24). Study site personnel telephone TED subjects the day after each infusion to ensure the subject's well-being and to inquire whether any AEs have occurred since their discharge from the infusion clinic the day before. Subjects are assessed for any AEs at all study visits and are told to call the study site at any time during the study if they have any health concerns whatsoever. Additional study visits are arranged at the request of either the PI or the subjects. The DSMB reviews safety and laboratory data at 6-month intervals during the study.

The antibodies are found to be effective in treating thyroid eye disease and also improving quality of life as provided for herein in subjects with TED.

Example 5

VRDN-5000 is an antagonist antibody to insulin-like growth factor-1 receptor (IGF-1R) under development for treatment of Thyroid Eye Disease (TED). TED is driven by Thyroid Stimulating Hormone Receptor (TSHR) agonistic autoantibodies and crosstalk between TSHR and IGF-1R. TED is characterized by recruitment of fibrocytes that express IGF-1R and TSHR in orbital tissues, where they mediate deposition of hyaluronan and expansion of orbital muscle and fat1. IGF-1R antagonism has been found to reverse this orbital tissue expansion and robustly relieve symptoms in TED patients2.

VRDN-5000 is a humanized monoclonal antibody targeting IGF-1R. The IGF-1R binding and antagonist characteristics of VRDN-5000 was analyzed.

Methods

Surface plasmon resonance (SPR): Antibodies were captured by immobilized anti-Fc, and recombinant IGF-1R extracellular domain (ECD) was flowed as analyte. Association and dissociation rate constants (ka and kd, respectively), and equilibrium dissociation constant KD were derived by global fit of data to single site model.

Epitope binning: VRDN-5000 was immobilized on a chip surface by amine coupling and used to capture IGF-1R-ECD, after which teprotumumab was flowed over the chip.

Cell binding: A549 human lung adenocarcinoma cells or primary human ocular choroid fibroblasts (HOCF) were incubated with varying concentrations of VRDN-5000 or teprotumumab. A single dose 50 nM IgG1 isotype control was used as negative control. Unbound antibody was removed by washing, and the cells were incubated with an Alexa Fluor 488-goat anti-human antibody and a cell impermeable dye to gate live cells. The median fluorescence intensity (MFI) of viable cells was measured by flow cytometry and the data were analyzed using FlowJo software. Dose curves were fitted using a non-linear regression model; log (agonist) vs response-variable slope (four parameters).

Internalization: Cells were incubated with various concentrations of antibodies of interest at 4° C. and 37° C. for 60 minutes. Cells were then washed 3× and incubated with FITC-labeled goat anti-human Fc secondary antibody for 30 minutes at 4° C. The MFI of viable cells was measured by flow cytometry and the data were analyzed using FlowJo software.

Cell surface marker expression: HOCF cells were incubated with directly labeled antibodies or IgG isotype control at 10 μg/mL. The median fluorescence intensity (MFI) was measured by flow cytometry and the data were analyzed using FlowJo software.

Antagonism: Serum starved A549 or HOCF cells were preincubated with varying concentrations of test antibody for one hour at 37° C., then stimulated by addition of 100 ng/ml (A549s) or 200 ng/mL (HOCFs) IGF-1 for 7 minutes at 37° C. Phosphorylated IGF-1R (pIGF1R) of biological duplicates was measured using the R&D Systems pIGF-1R ELISA according to the manufacturer's protocol and pIGF-1R concentrations were normalized to the lowest test antibody concentration. Dose curves were fit using a non-linear regression model; log (inhibitor) vs response-variable slope (four parameters)).

Results

Figure 2A:
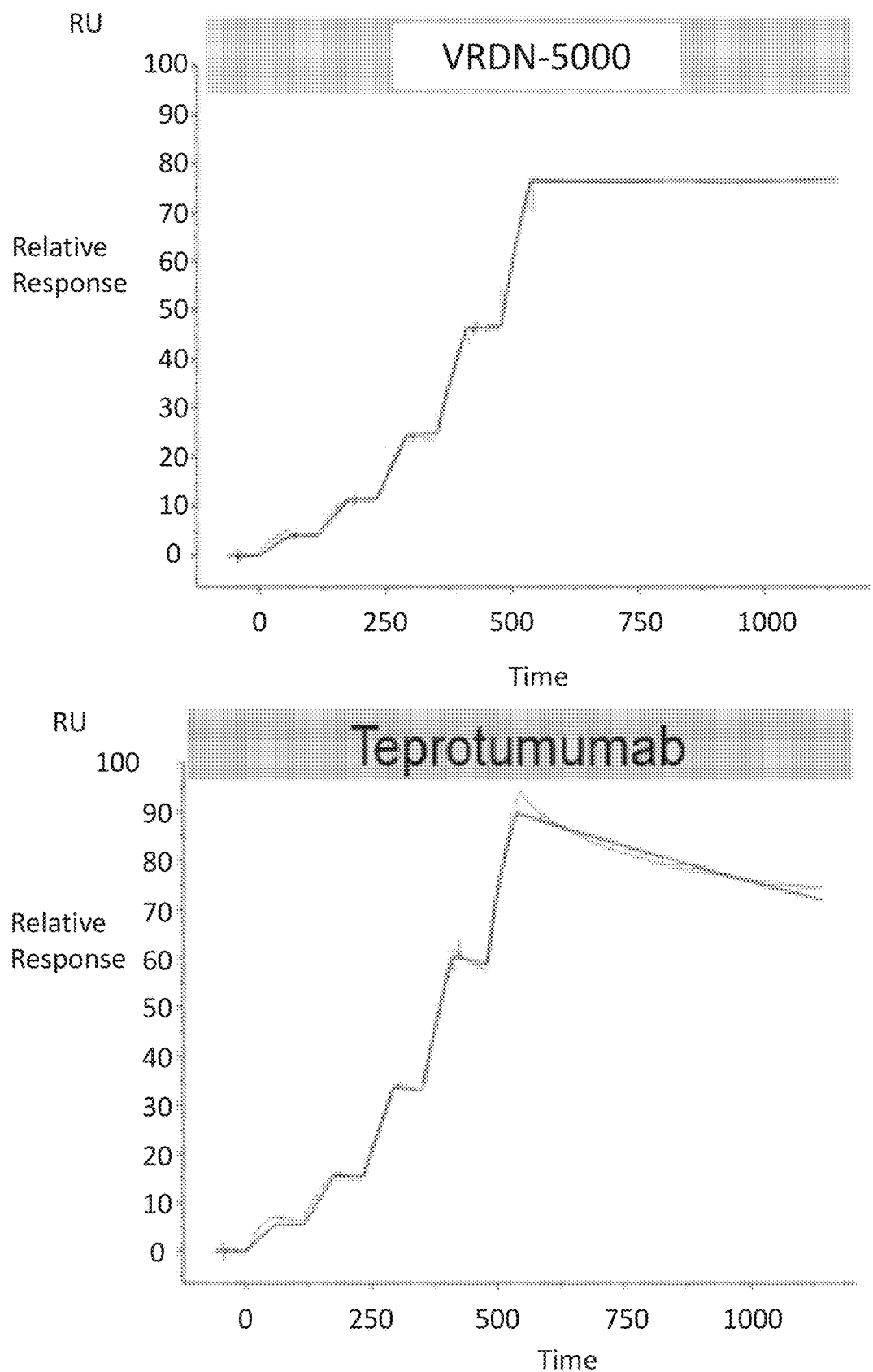
FIG. 2A-B illustrates various embodiments as provided for herein.
Figure 2B:
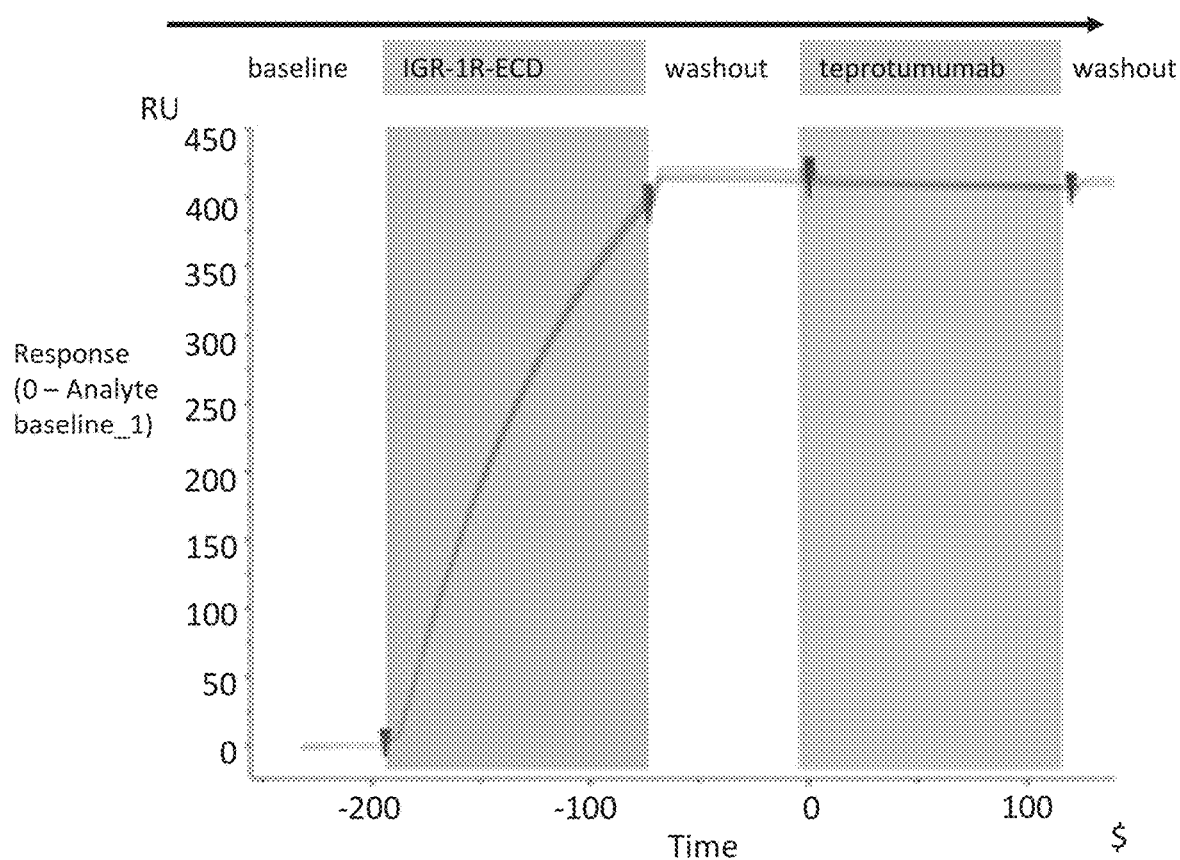

VRDN-5000 Binds IGF-1R With Sub-Nanomolar Affinity. FIG. 2A the figure below illustrates that increasing concentrations of IGF-1R-ECD bound to anti-FC captured VRDN-5000 or teprotumumab reveal a stepwise increase in SPR signal, enabling a global fit to a binding model. Following IGF-1R washout, VRDN-5000 shows a more sustained binding interaction. FIG. 2B illustrates IGF-1R-ECD bound robustly to immobilized VRDN-5000. Teprotumumab showed no binding to the IGF-1R: VRDN-5000 complex, suggesting that teprotumumab and VRDN-5000 have overlapping epitopes.

Figure 3A:
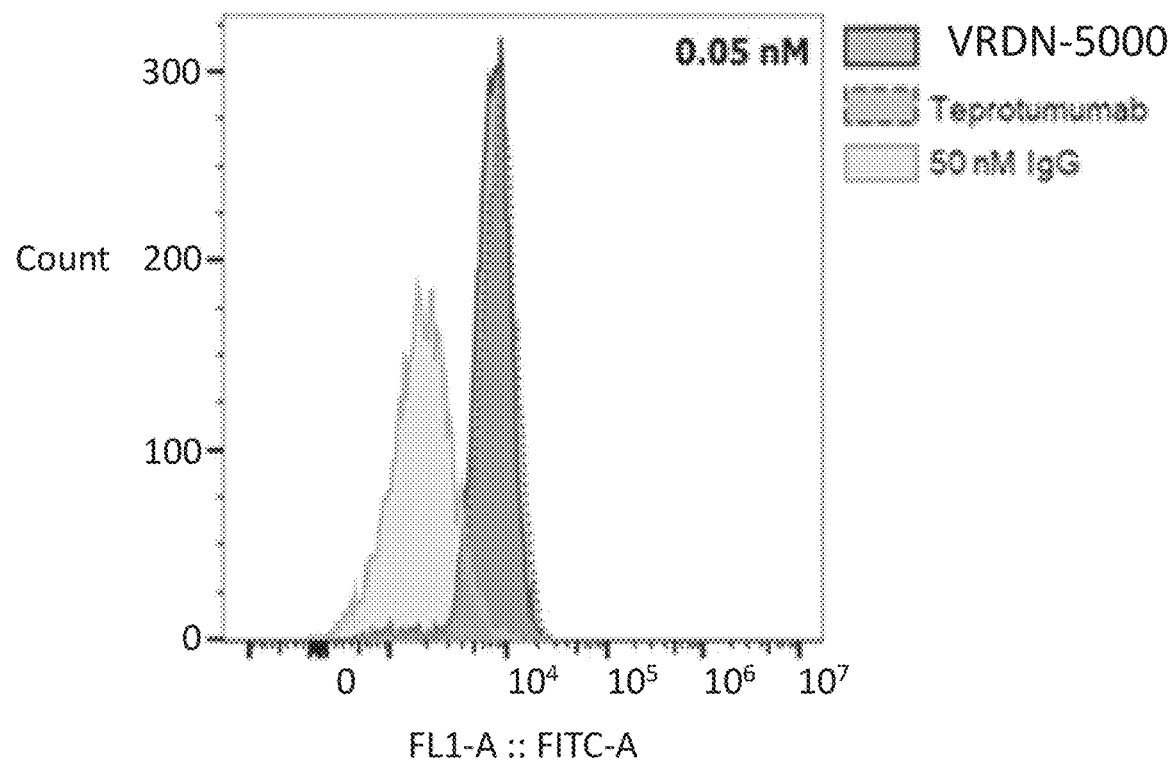
FIG. 3A-F illustrates various embodiments as provided for herein.
Figure 3B:
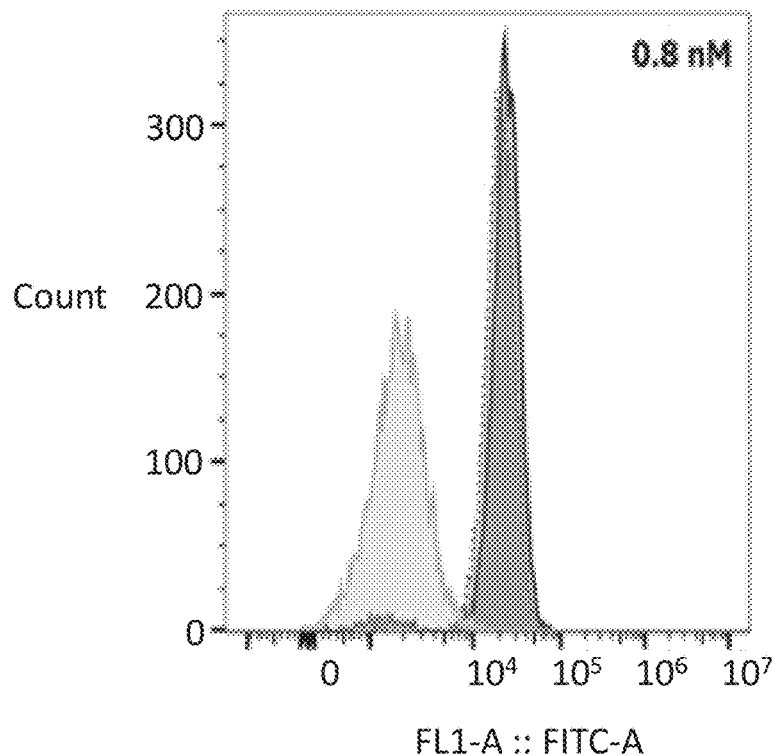
Figure 3C:
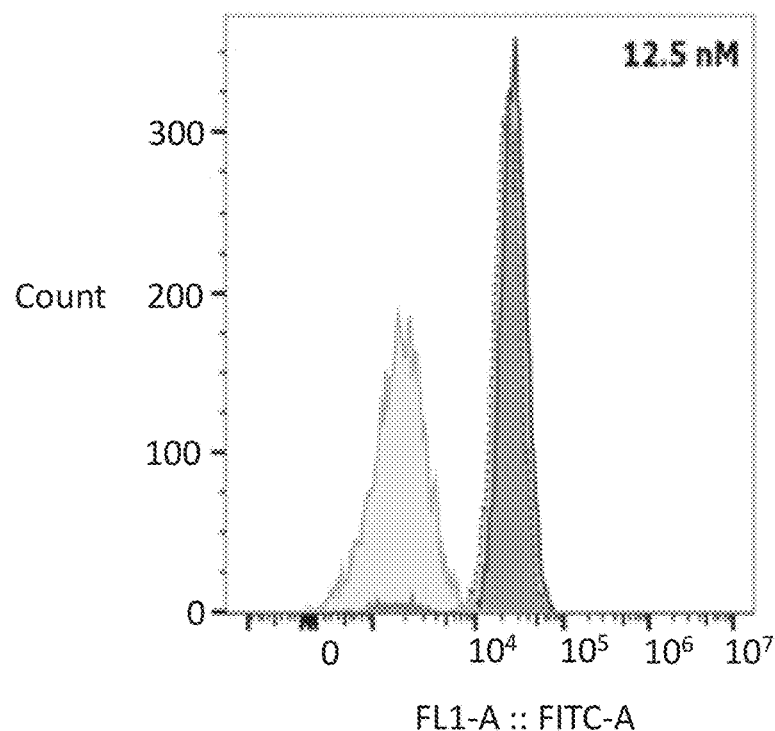
Figure 3D:
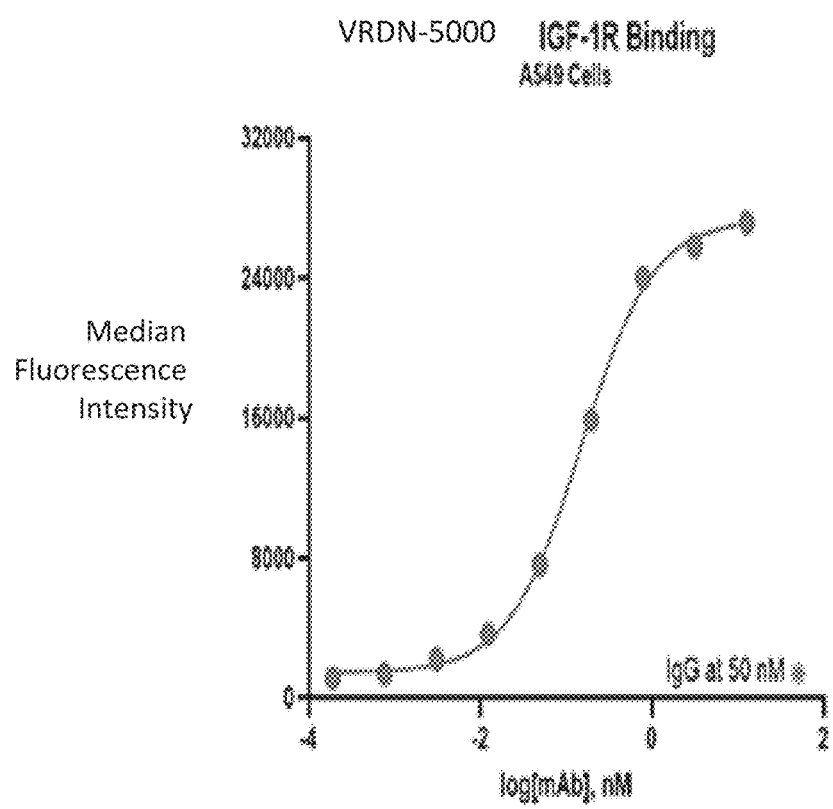
Figure 3E:
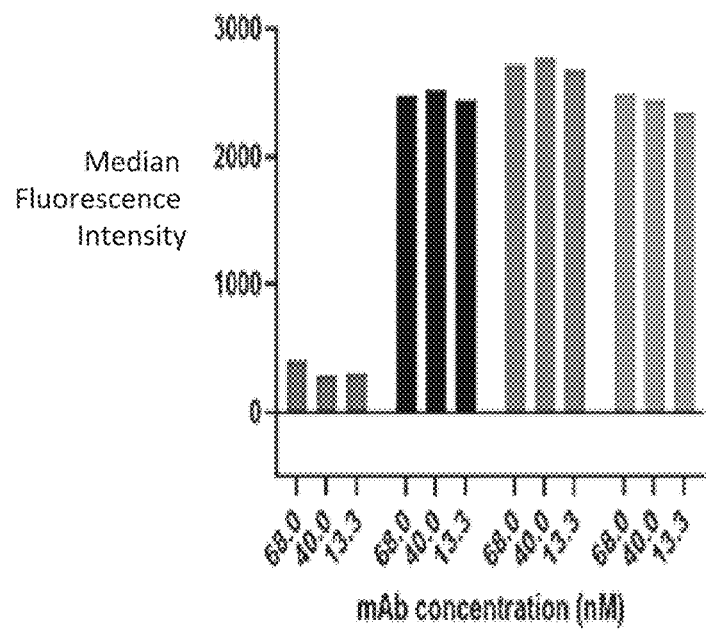
Figure 3F:
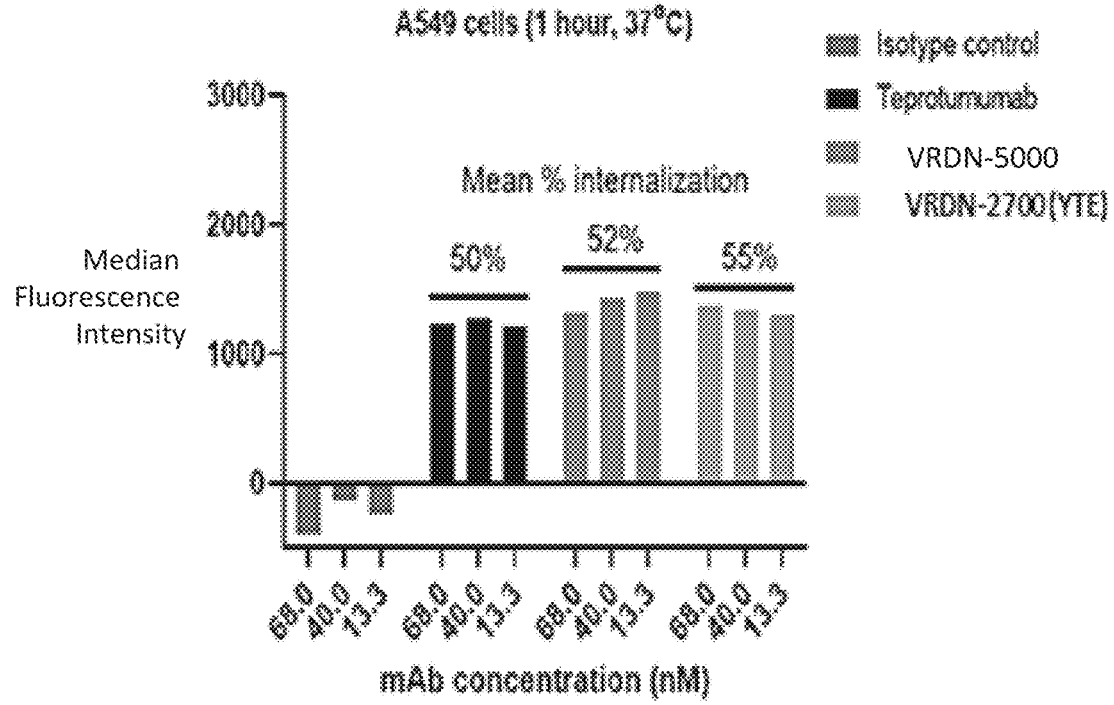

VRDN-5000 Binds With High Affinity To IGF-1R On A549 Cells. As illustrated in FIG. 3A-C, VRDN-5000 binding to A549 cells was assessed by flow cytometry and found to have similar binding distribution as teprotumumab at three different concentrations. As illustrated FIG. 3D the binding dose response curve demonstrated VRDN-5000 EC50=0.1 nM. As illustrated in FIG. 3E VRDN-5000, VRDN-2700 (VRDN-5000 with M252Y, S254T, and T256E mutation in the Fc domain), and teprotumumab show comparable binding at temperatures that block IGF-1R receptor internalization. FIG. 3F illustrates that VRDN-5000, VRDN-2700 with a M252Y, S254T, and T256E mutation in the Fc domain, and teprotumumab cause comparable levels of internalization (~50%) measured by reduction in membrane IGF-1R receptor levels at 37° C. vs 4° C.

HOCFs as an In Vitro Model for TED Pathology.

Figure 4A:
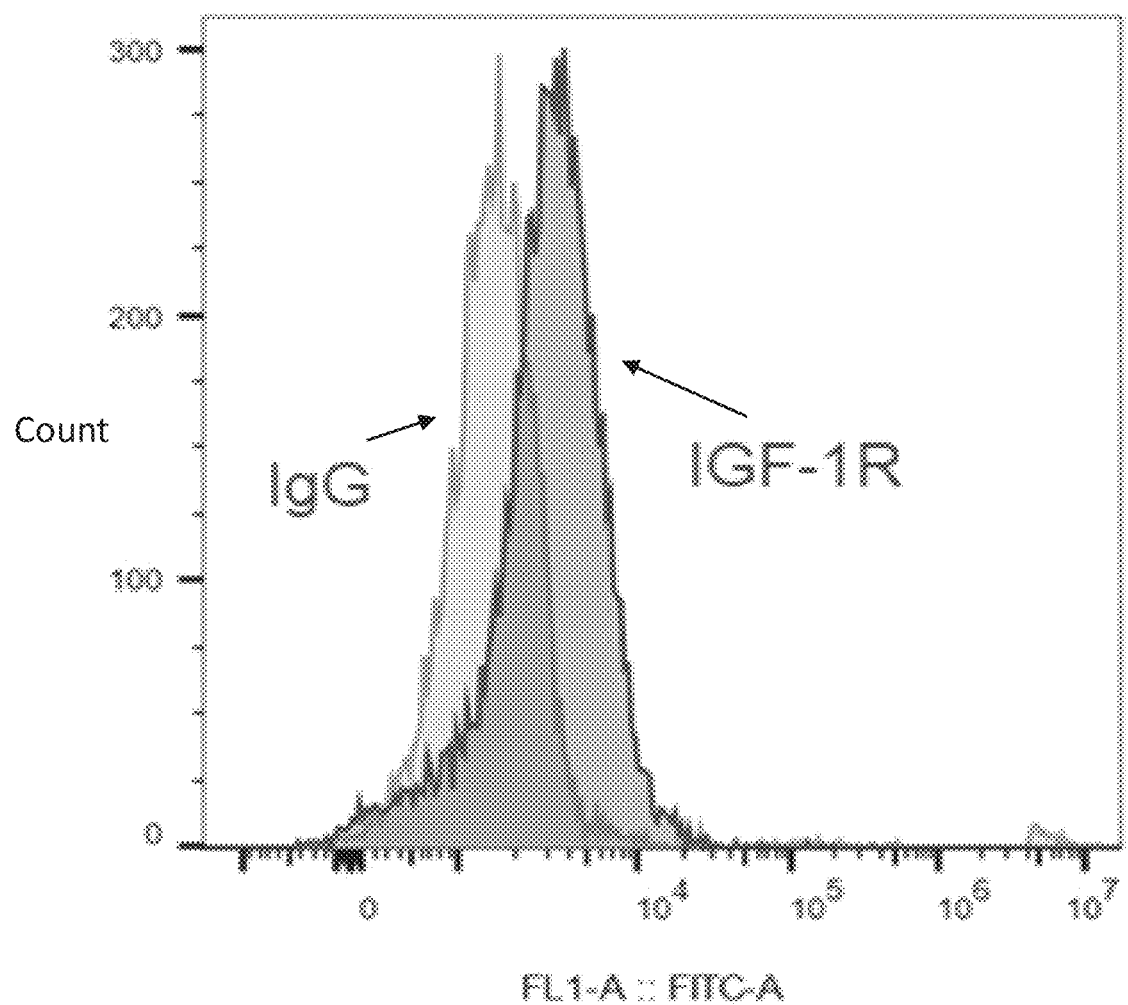
FIG. 4A-C illustrates various embodiments as provided for herein.
Figure 4B:
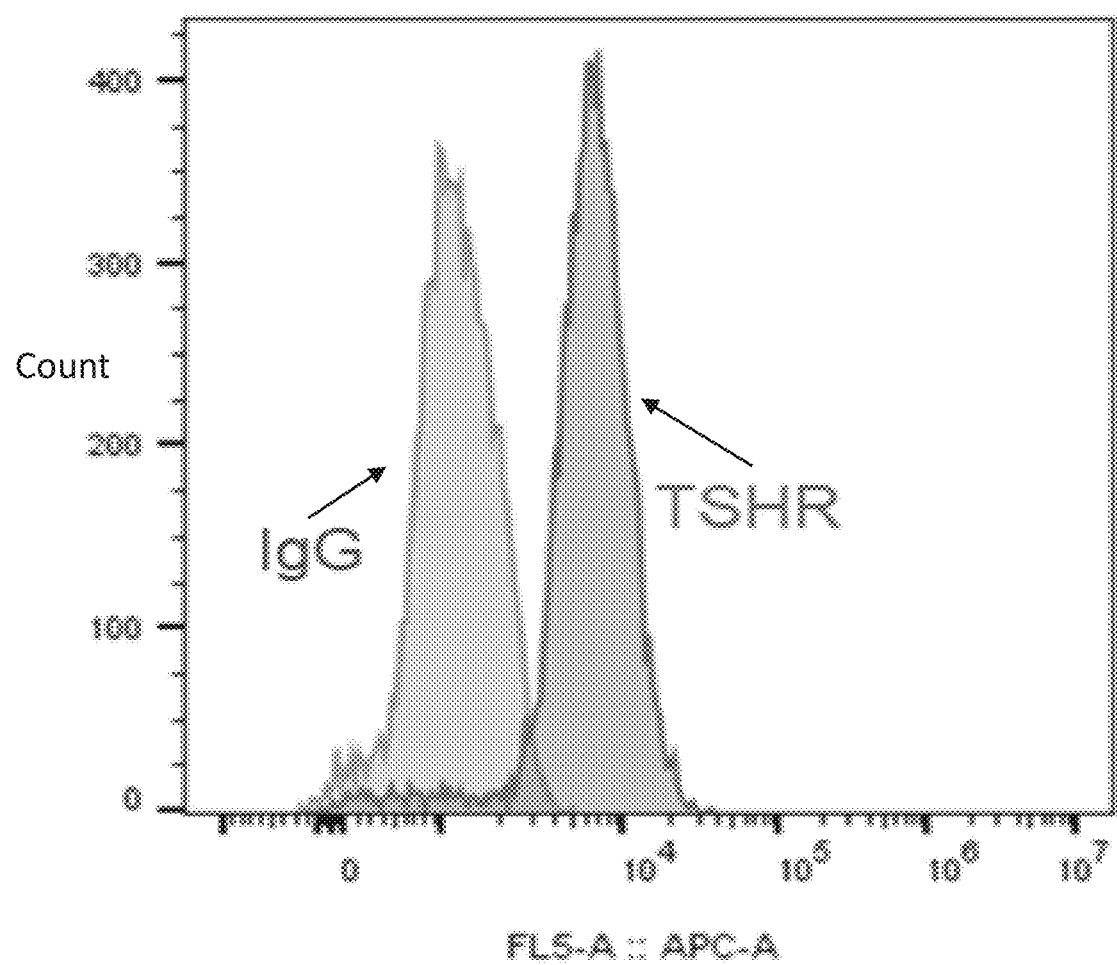
Figure 4C:
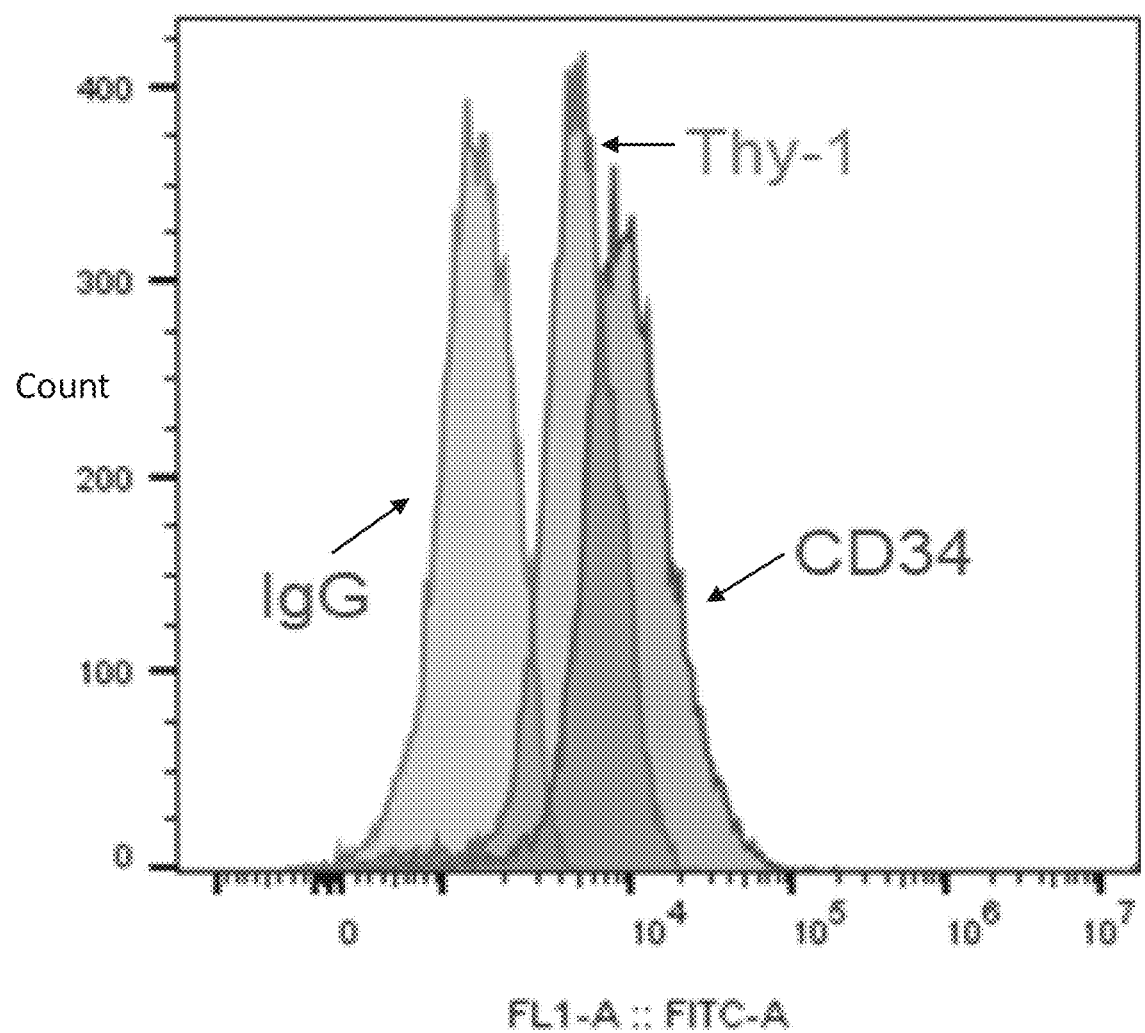

CD34+, Thy-1+ orbital fibroblasts are implicated in extracellular matrix deposition and pathogenic fibrosis in TED5. Here, HOFCs were shown to express (A) IGF-1R and (B) TSHR, as well as (C) CD34 and Thy-1, which demonstrates their ability to be used as an in vitro model system for IGF-1R function in TED. The data is illustrated in FIG. 4A-C.

VRDN-5000 Binds with High Affinity to IGF-1R on HOCF Cells.

Figure 5A:
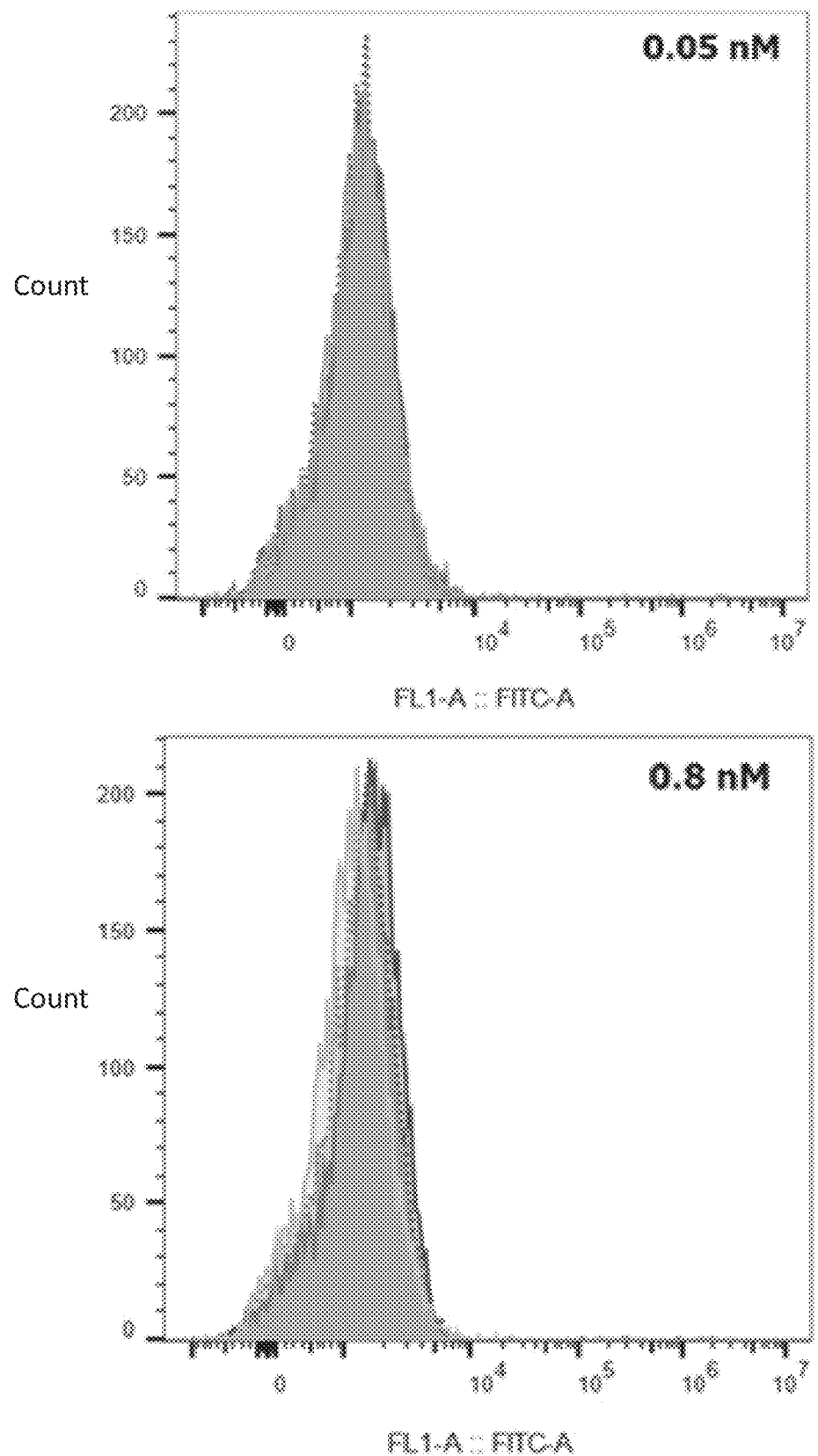
FIG. 5A-B illustrates various embodiments as provided for herein.
Figure 5B:
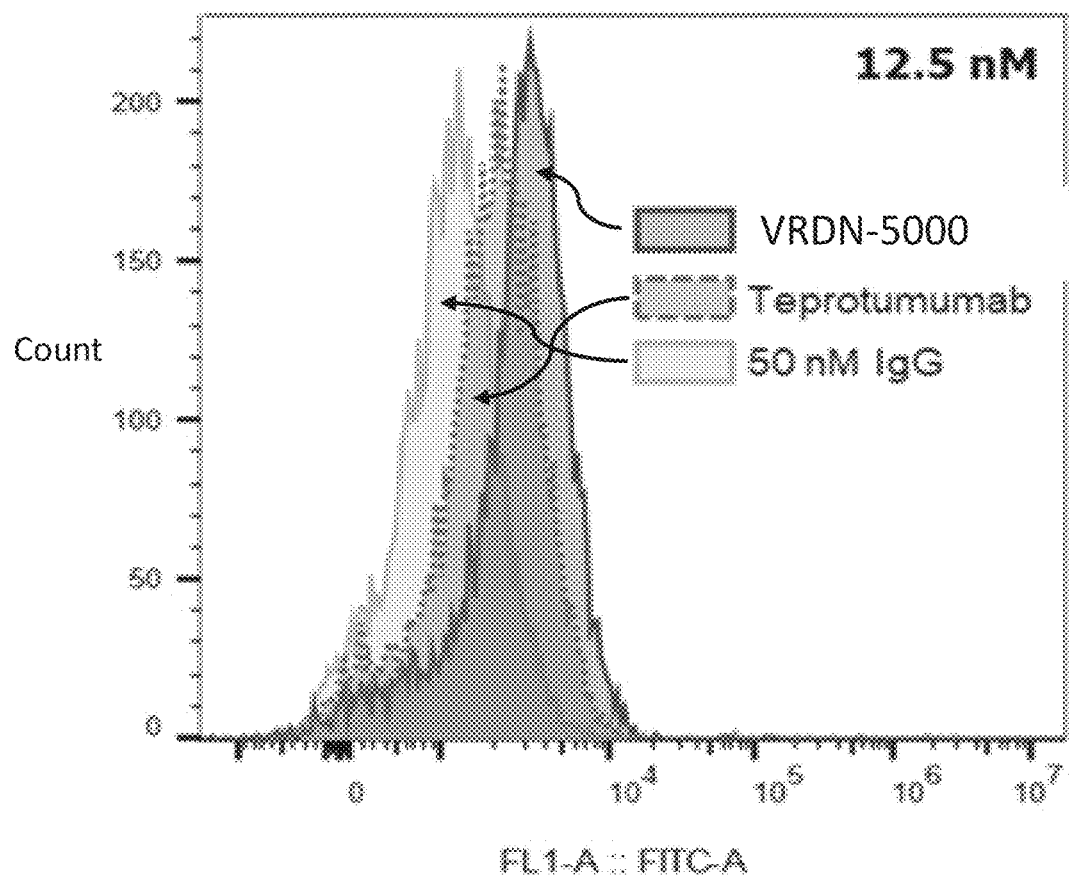
Figure 5B:
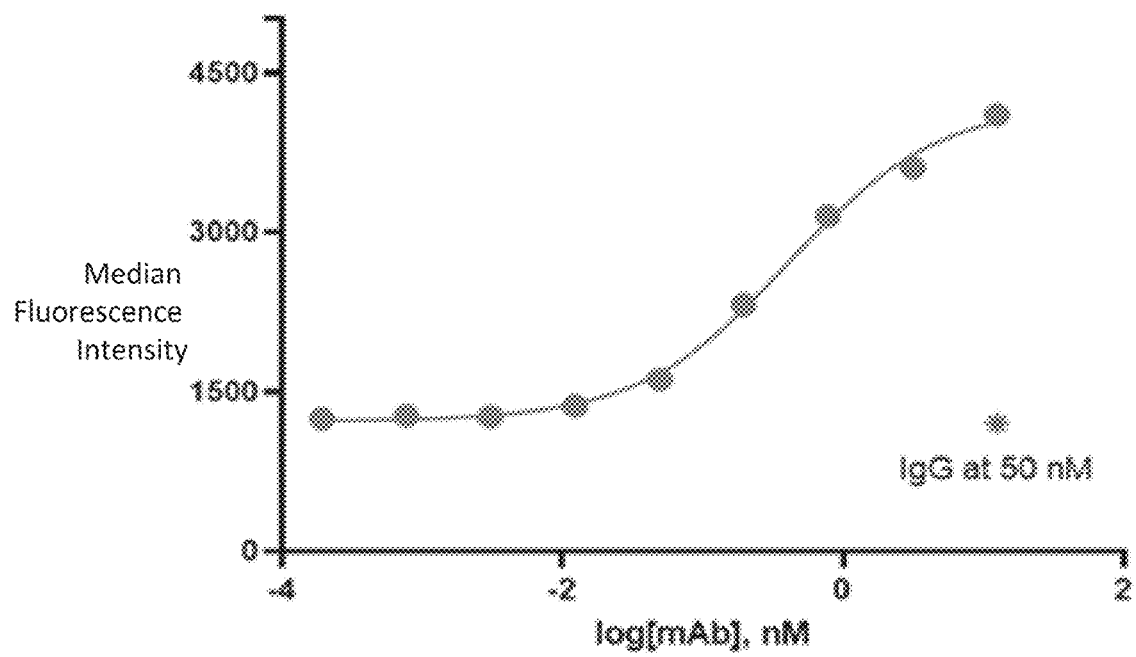

FIG. 5A-B illustrate VRDN-5000 binding to HOCF cells, which was assessed by flow cytometry and found to have largely similar binding as teprotumumab at three different concentrations. Panel D illustrates a binding dose response curvE, which demonstrated VRDN-5000 having an EC50=0.4 nM.

Figure 6A:
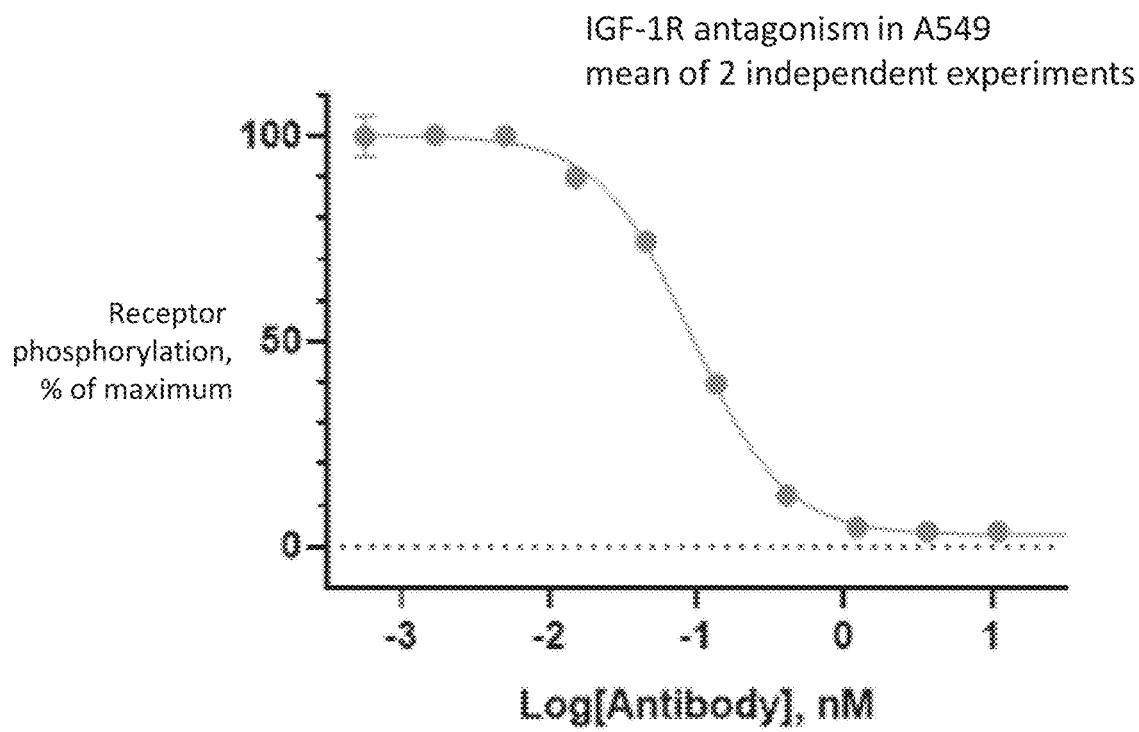
FIG. 6A-B illustrates various embodiments as provided for herein.
Figure 6B:
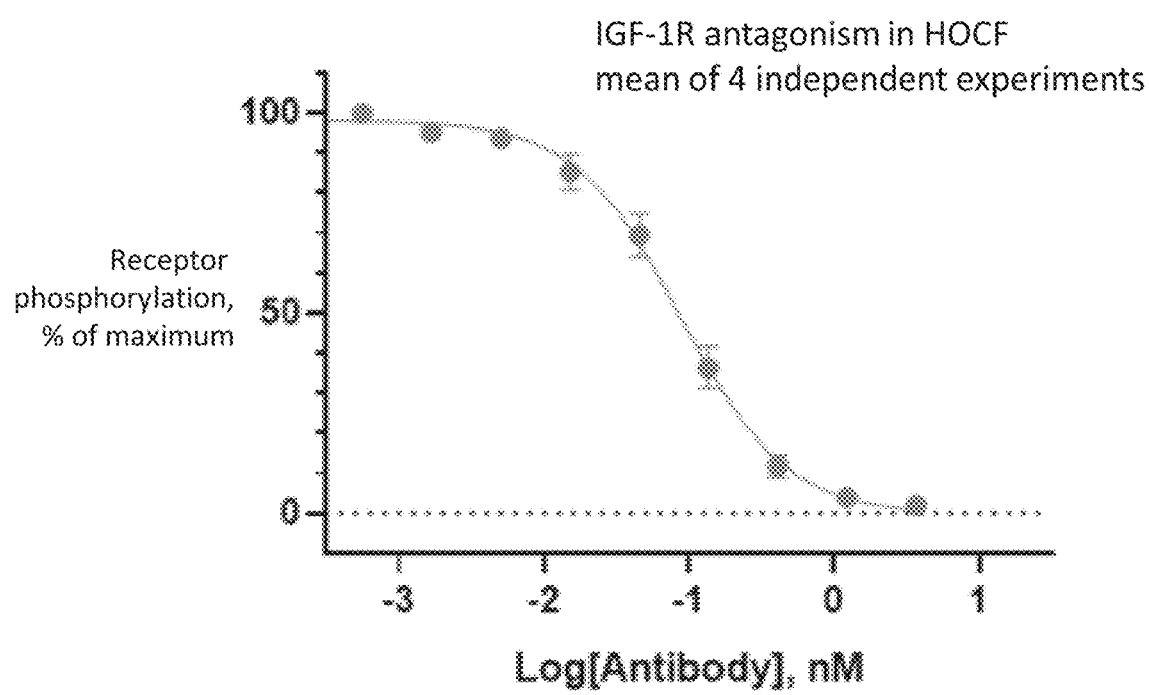

VRDN-5000 Is A Sub-Nanomolar IGF-1R Antagonist. VRDN-5000 potently inhibits IGF-1 stimulated receptor phosphorylation on A549 cells (IC50=0.09 nM) and HOCF cells (IC50=0.09 nM), which is illustrated in FIG. 6A-B.

Example 6

VRDN-5000 Is A More Potent Inhibitor Of IGF-1 Binding To IGF1R As Compared To Teprotumumab.

Figure 7:
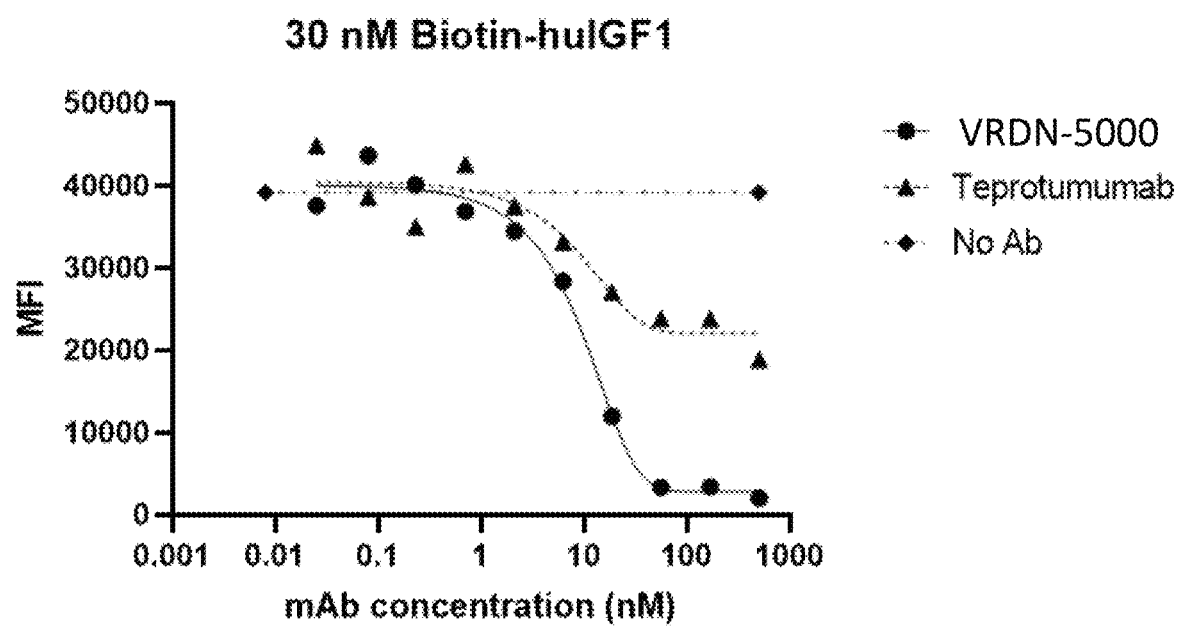
FIG. 7 illustrates various embodiments as provided for herein.

IGF-1 binding to IGF-1R present on the surface of a cell was determined. Briefly, labeled IGF1 was incubated with the cells in the presence of VRDN-5000, teprotumumab, or no antibody (negative control). Cells were washed and then IGF-1 bound to the cells was determined by detecting the presence of the IGF1 label As illustrated in FIG. 7, VRDN-5000 was found to be a more potent inhibitor. The maximal inhibition was found to be 94% for VRDN-5000 and 48% for teprotumumab.

Figure 8:
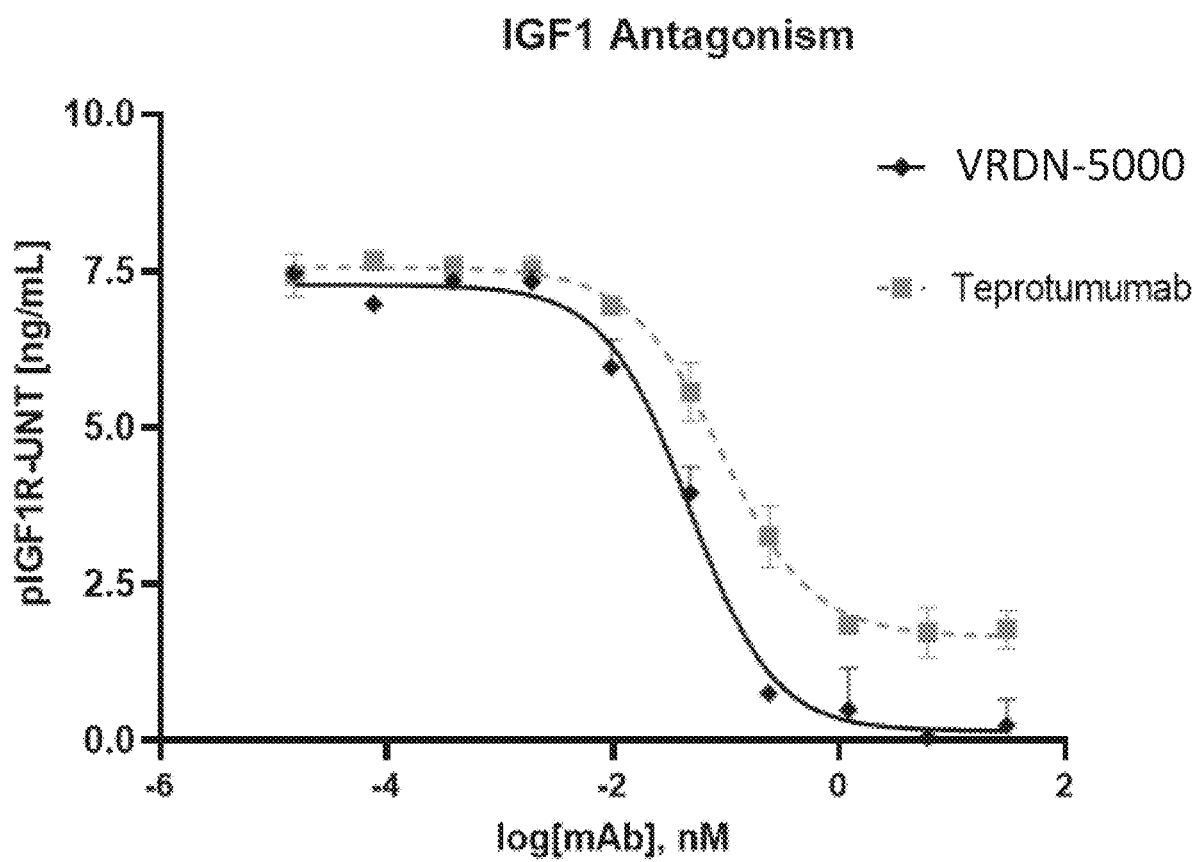
FIG. 8 illustrates various embodiments as provided for herein.
Figure 9:
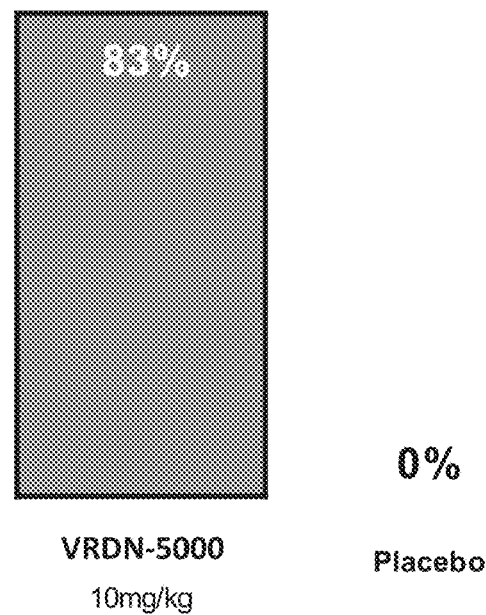
FIG. 9 illustrates various embodiments as provided for herein.
Figure 9:
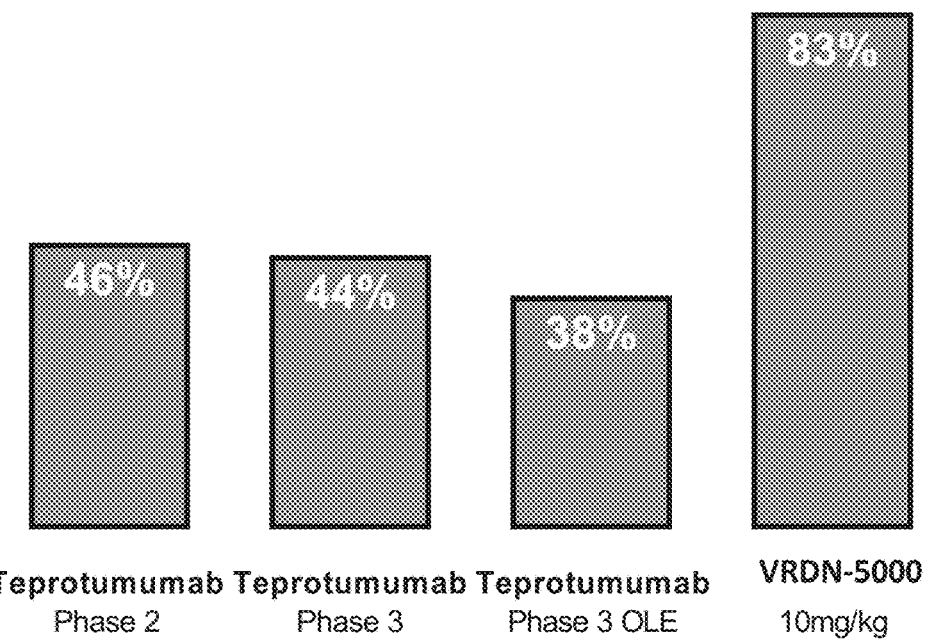
Figure 10A:
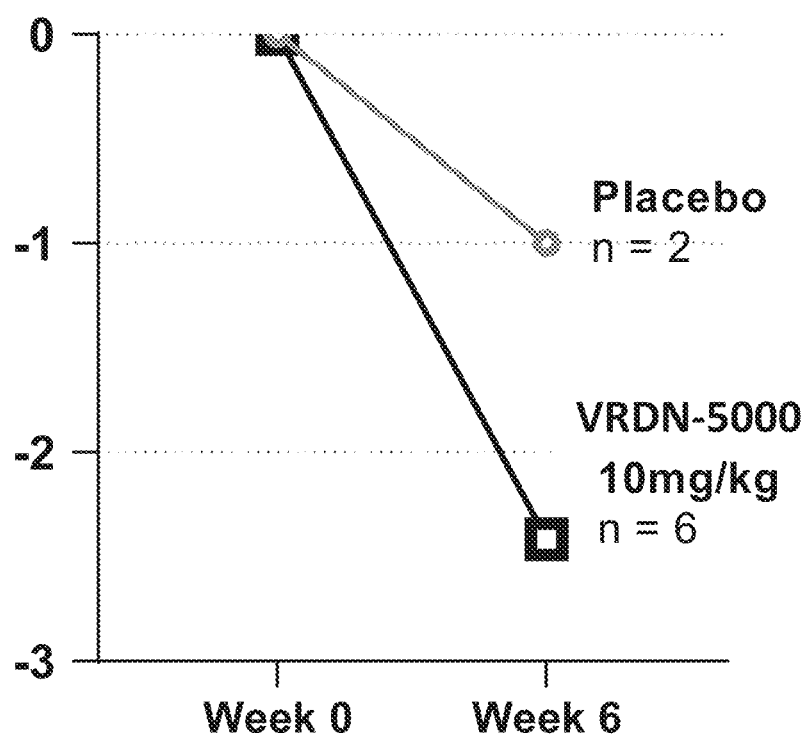
FIG. 10A-C illustrate various embodiments as provided for herein.
Figure 10B:
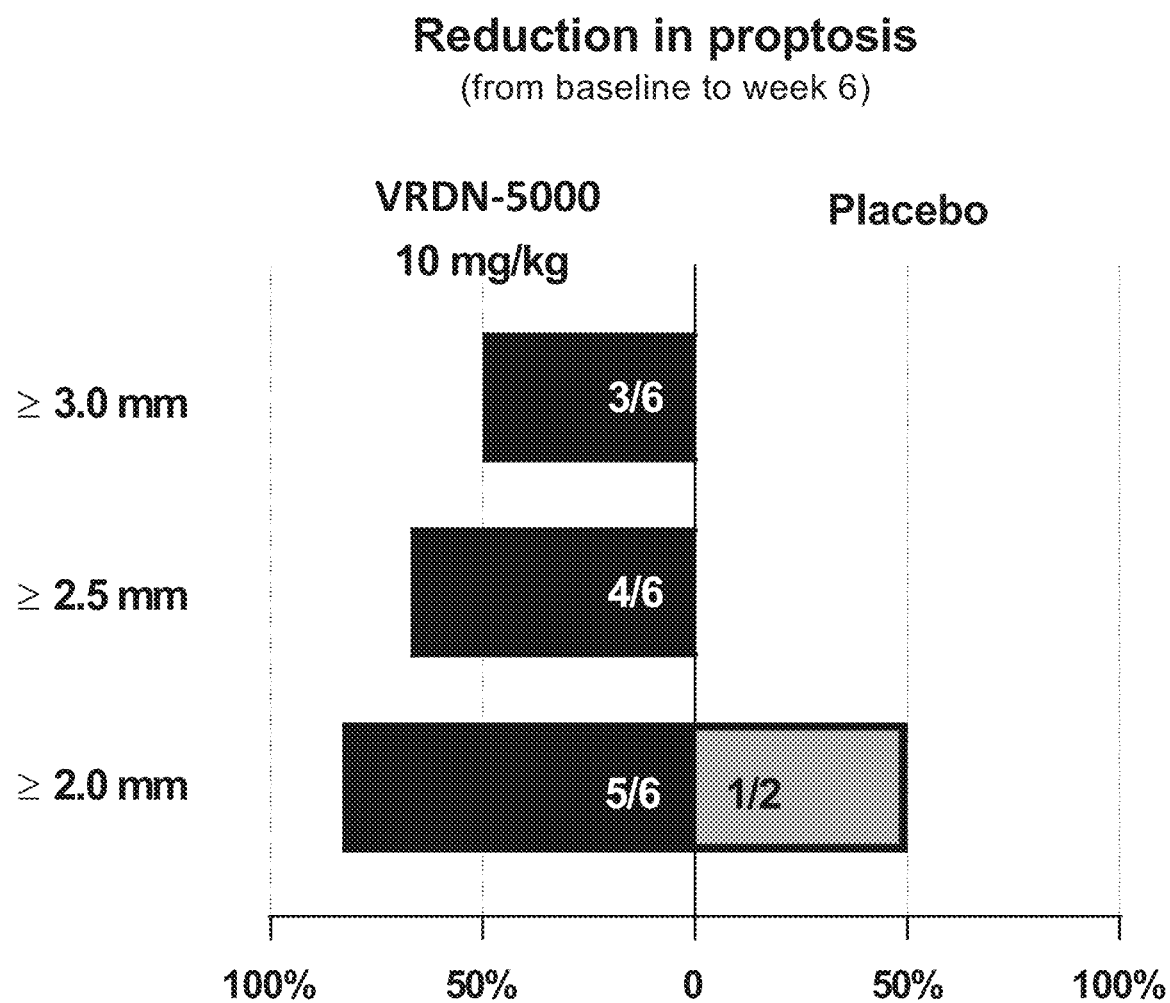
Figure 10C:
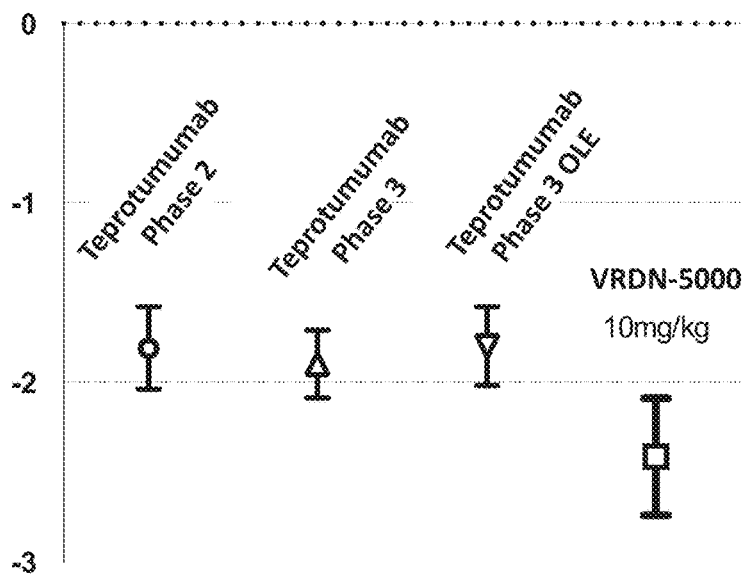
Figure 10C:
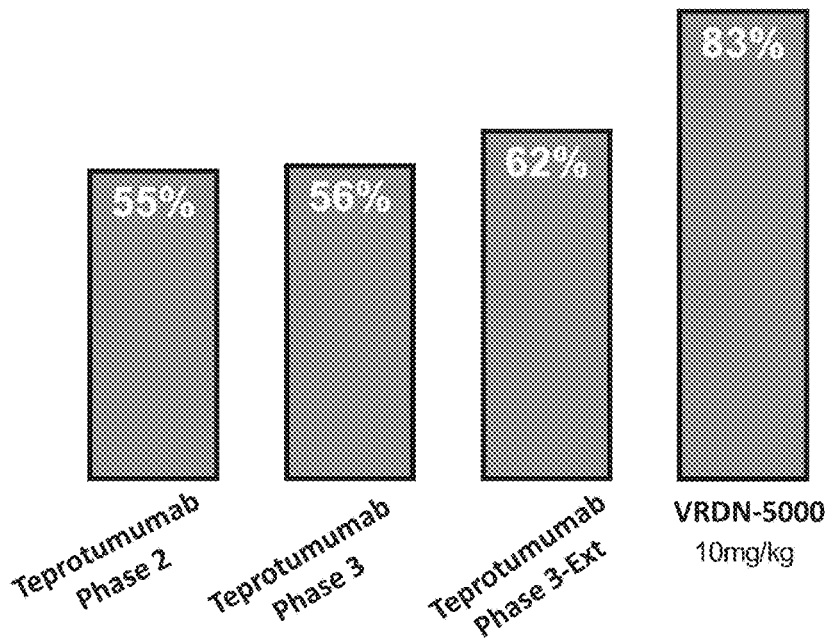
Figure 11:
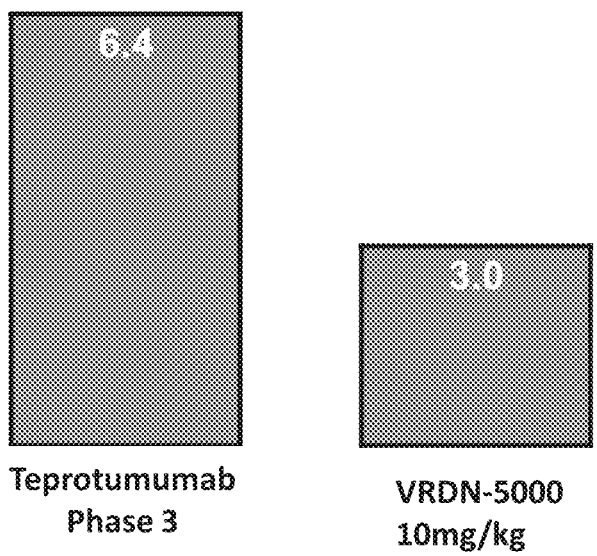
FIG. 11 illustrates various embodiments as provided for herein.
Figure 11:
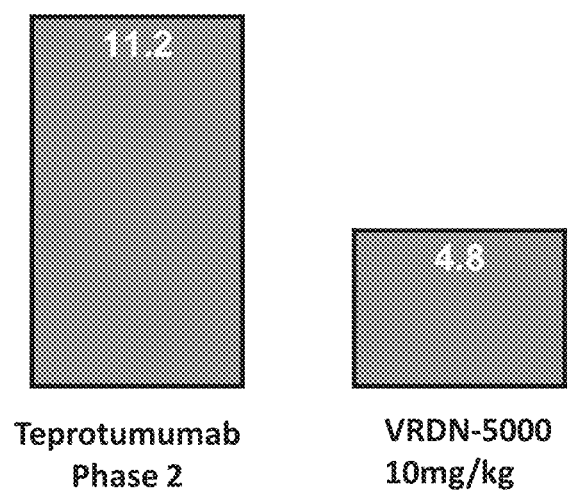
Figure 12A:
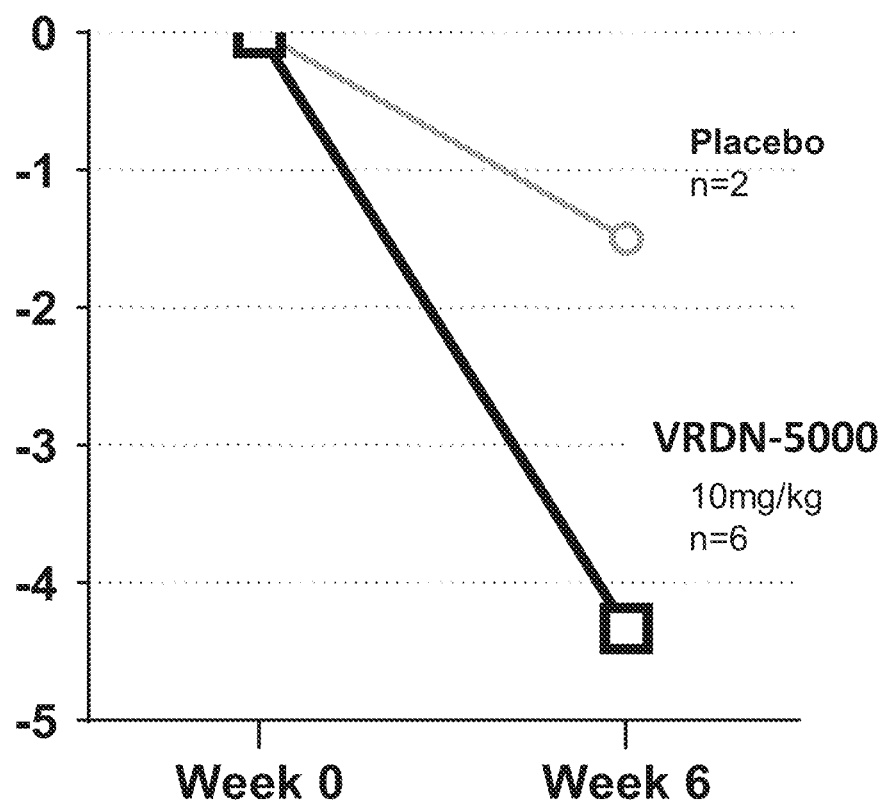
Figure 12B:
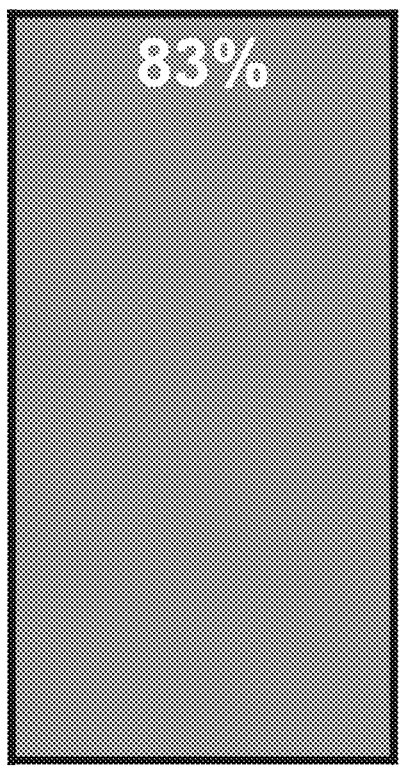
Figure 13B:
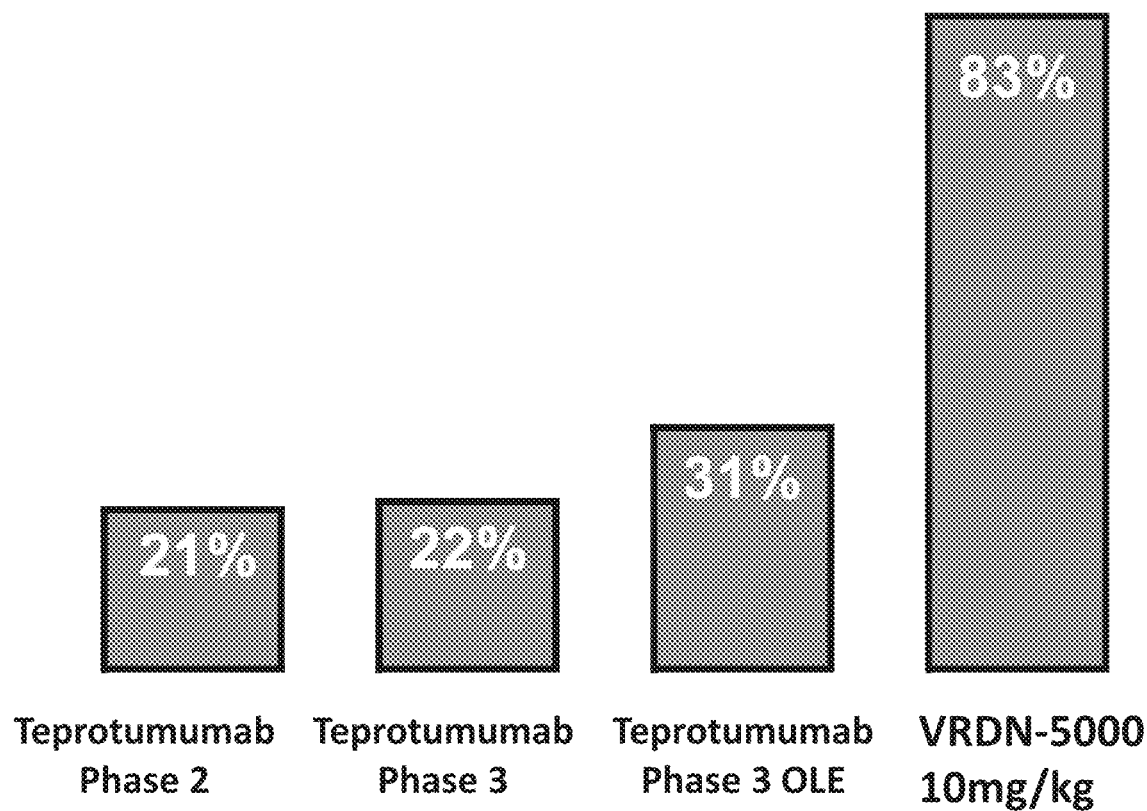
Figure 14A:
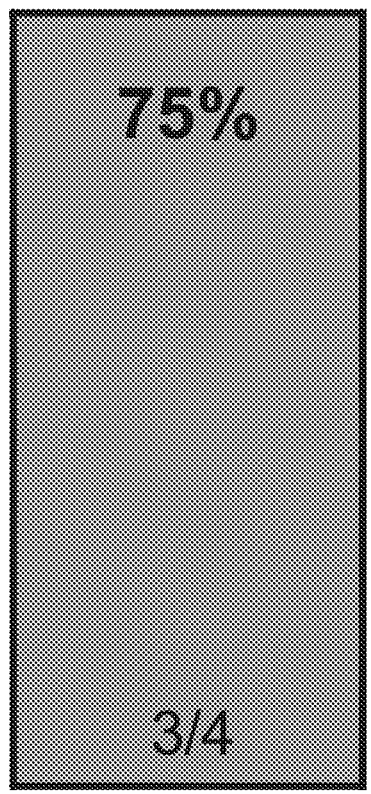
FIG. 14A-B illustrate various embodiments as provided for herein.
Figure 14B:
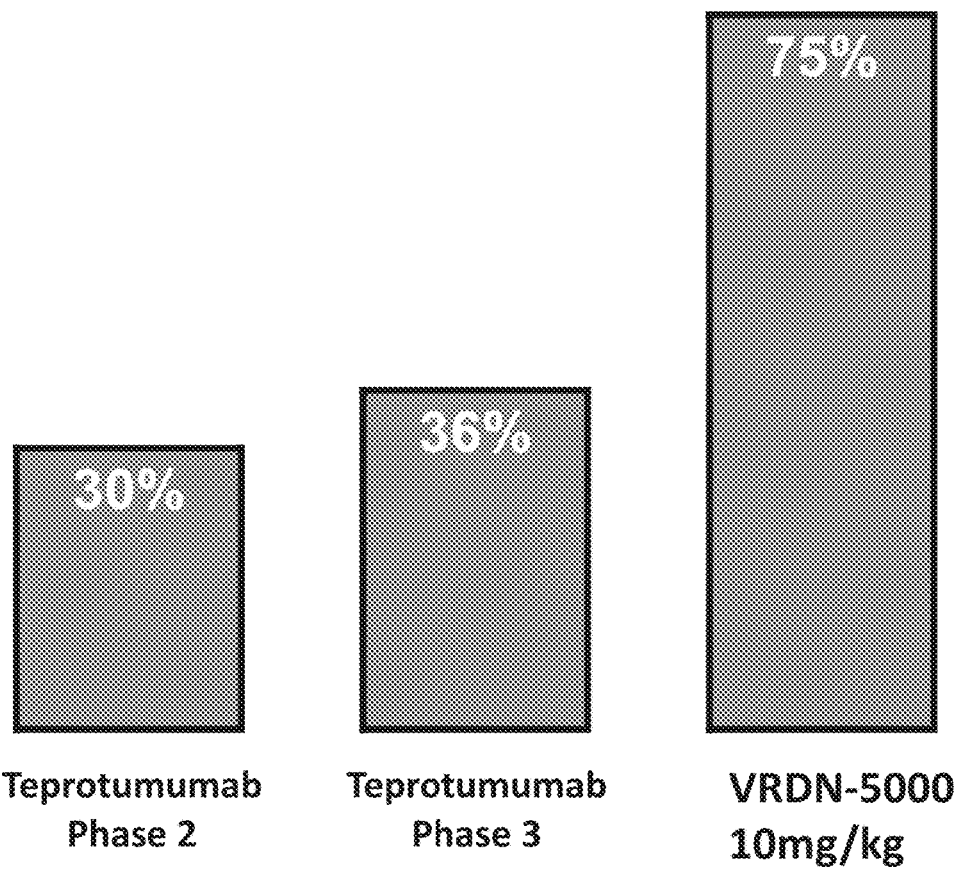

Inhibition was also evaluated in an IGF-1 induced IGF1-R phosphorylation. Cell cultures were preincubated with antibody (VRDN-5000 or teprotumumab) and IGF1 stimulation. Cells were lysed and pIGF1R was measured. VRDN-5000 was found to have a maximal inhibition of autophosphorylation of 96% whereas teprotumumab was found to have a maximal inhibition of autophosphorylation of 76%. These results are illustrated in FIG. 8.

VRDN-5000's more potent inhibition of IGF1 activity was also found in measuring Akt phosphorylation. Briefly, cell cultures were preincubated with antibody (VRDN-5000 or teprotumumab) and stimulated with IGF1. Cells were lysed and pAKT measured using a standard assay. VRDN-5000 was found to have a maximal inhibition of Akt phosphorylation of 93% whereas teprotumumab was found to have a maximal inhibition of Akt phosphorylation of 66%.

These results demonstrate that VRDN-5000 and teprotumumab epitopes on IGF-1R overlap, that VRDN-5000 binds to IGF-1R on cells with sub-nanomolar EC50, VRDN-5000 promotes IGF-1R internalization, and that VRDN-5000 inhibits IGF-1R phosphorylation with sub-nanomolar IC50. Accordingly, VRDN-5000 binds, antagonizes, and internalizes IGF-1R at sub-nanomolar concentrations, suggesting that VRDN-5000 should be a able to be used for the potential, potent inhibition of the pathophysiology driving TED.

Example 7

VRDN-5000 treats thyroid associated ophthalmopathy in a subject with a reduction in proptosis occurring within 3 weeks of a first dose. Two infusions of VRDN-5000 at a dose of 10 mg/kg three weeks apart resulted in rapid and significant improvements in proptosis, CAS, and diplopia at week 6. The results demonstrates that at week 6, patients treated with VRDN-5000 has a proptosis response: 5/6 patients (83%); median time to proptosis response: 3 weeks; CAS response: 6/6 (100%) CAS Score 0 or 1: 4/6 (67%); an Overall response: 5/6 patients (83%); and Diplopia resolution: 3/4 (75%). The observed mean reduction in proptosis and improvement in diplopia as soon as 6 weeks after the first infusion of VRDN-5000 is significantly faster than what has been published for teprotumumab (Smith et al., Teprotumumab for Thyroid-Associated Ophthalmopathy, N Engl J Med 2017; 376:1748-61; Douglas et al., Teprotumumab for the Treatment of Active Thyroid Eye Disease, N. Engl J Med 2020; 382:341-52; and Douglas et al., Teprotumumab Efficacy, Safety, and Durability in Longer-Duration Thyroid Eye Disease and Re-treatment, Ophthalmology 2022, vol 129, no. 4). The comparison data is illustrated in FIGS. 9-14B.

As the data demonstrates, the subjects on average, had a reduction or improvement in at least two of proptosis, diplopia, and CAS score, which was not observed in the placebo cohort. These data demonstrate the unexpected results of how quickly VRDN-5000 can achieve a therapeutic effect, which could not have been predicted.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57 (b) (1), to relate to each and every individual publication, database entry (e.g. Genbank sequences or GeneID entries), patent application, or patent, each of which is clearly identified in compliance with 37 C.F.R. § 1.57 (b) (2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications in addition to those described herein will become apparent to those skilled in the art from the foregoing description and the accompanying figures. Such modifications are intended to fall within the scope of the embodiments and any appended claims.

The present specification is considered to be sufficient to enable one skilled in the art to practice the embodiments. Various modifications in addition to those shown and described herein will become apparent to those skilled in the art from the foregoing description and fall within the scope of the present disclosure and any appended claims.

What is claimed is:

1. A method of treating active thyroid eye disease (TED) in a subject in need thereof, the method comprising:
administering a first dose of a pharmaceutical composition comprising an anti-IGF-IR antibody at 10 mg/kg, and
administering a subsequent dose of the pharmaceutical composition comprising the anti-IGF-1R antibody at 10 mg/kg three weeks after the first dose, such that the subject has a reduction in proptosis or an improvement in CAS score within 6 weeks of the first dose, wherein administration of the antibody is by intravenous infusion,
wherein the anti-IGF-1R antibody comprises a light chain and a heavy chain, and
wherein the heavy chain comprises a HCDR1 of SEQ ID NO: 7, a HCDR2 of SEQ ID NO: 8, and a HCDR3 of SEQ ID NO: 9 and the light chain comprises a LCDRI of SEQ ID NO: 4, a LCDR2 of SEQ ID NO: 5 and a LCDR3 of SEQ ID NO: 6.

2. The method of claim 1, wherein the light chain comprises a variable region having the amino acid sequence of SEQ ID NO: 2 and the heavy chain comprises a variable region sequence having the amino acid sequence of SEQ ID NO: 3.

3. The method of claim 2, wherein the light chain comprises an amino acid sequence of SEQ ID NO: 11, and the heavy chain comprises an amino acid sequence of SEQ ID NO: 10.

4. The method of claim 1, wherein the antibody is administered by intravenous infusion over 45 minutes to about 90 minutes.

5. The method of claim 1, wherein the CAS score has an improvement of at least −2.

6. The method of claim 1, wherein the antibody is administered by intravenous infusion over 60 minutes to about 90 minutes.

7. The method of claim 1, wherein the CAS score has an improvement of at least −3.

8. The method of claim 1, wherein the CAS score has an improvement of at least −4.

* * * * *